US011578052B2

(12) United States Patent
Downes et al.

(10) Patent No.: US 11,578,052 B2
(45) Date of Patent: *Feb. 14, 2023

(54) PPAR AGONISTS, COMPOUNDS, PHARMACEUTICAL COMPOSITIONS, AND METHODS OF USE THEREOF

(71) Applicants: Mitobridge, Inc., Cambridge, MA (US); The Salk Institute for Biological Studies, La Jolla, CA (US)

(72) Inventors: Michael Downes, La Jolla, CA (US); Ronald M. Evans, La Jolla, CA (US); Arthur Kluge, Lincoln, MA (US); Bharat Lagu, Acton, MA (US); Masanori Miura, Tsukuba (JP); Sunil Kumar Panigrahi, Hyderabad (IN); Michael Patane, Andover, MA (US); Susanta Samajdar, Hyderabad (IN); Ramesh Senaiar, Hyderabad (IN); Taisuke Takahashi, Tsukuba (JP)

(73) Assignees: Mitobridge, Inc., Cambridge, MA (US); The Salk Institute for Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/162,157

(22) Filed: Jan. 29, 2021

(65) Prior Publication Data
US 2021/0253549 A1 Aug. 19, 2021

Related U.S. Application Data

(63) Continuation of application No. 16/682,676, filed on Nov. 13, 2019, now Pat. No. 10,906,885, which is a continuation of application No. 16/510,976, filed on Jul. 15, 2019, now Pat. No. 10,479,775, which is a continuation of application No. 15/766,455, filed as application No. PCT/US2016/055521 on Oct. 5, 2016, now Pat. No. 10,399,958.

(60) Provisional application No. 62/352,348, filed on Jun. 20, 2016, provisional application No. 62/243,263, filed on Oct. 19, 2015, provisional application No. 62/238,629, filed on Oct. 7, 2015.

(51) Int. Cl.
| | | |
|---|---|---|
| *C07D 233/64* | (2006.01) | |
| *C07D 401/04* | (2006.01) | |
| *C07D 405/10* | (2006.01) | |
| *A61P 21/00* | (2006.01) | |
| *A61P 25/00* | (2006.01) | |

(52) U.S. Cl.
CPC ............ *C07D 401/04* (2013.01); *A61P 21/00* (2018.01); *A61P 25/00* (2018.01); *C07D 233/64* (2013.01); *C07D 405/10* (2013.01)

(58) Field of Classification Search
CPC ... C07D 233/64; C07D 401/04; C07D 405/10
See application file for complete search history.

(56) References Cited

U.S. PATENT DOCUMENTS

| | | |
|---|---|---|
| 4,228,281 A | 10/1980 | Kainmuller et al. |
| 5,519,138 A | 5/1996 | Ries et al. |
| 6,054,457 A | 4/2000 | Setoi et al. |
| 9,938,234 B2 | 4/2018 | Evans et al. |
| 10,035,819 B2 | 7/2018 | Evans et al. |
| 10,399,958 B2 | 9/2019 | Downes et al. |
| 10,479,775 B1 | 11/2019 | Downes et al. |
| 10,550,071 B2 | 2/2020 | Evans et al. |
| 10,906,885 B2 * | 2/2021 | Downes .................. A61P 25/00 |
| 10,927,094 B2 * | 2/2021 | Lagu ..................... C07D 233/60 |
| 2007/0054839 A1 | 3/2007 | Okamoto et al. |
| 2010/0063041 A1 | 3/2010 | Moon et al. |
| 2017/0305894 A1 | 10/2017 | Baiga et al. |
| 2018/0170857 A1 | 6/2018 | Evans et al. |
| 2018/0305403 A1 | 10/2018 | Evans et al. |
| 2020/0157074 A1 | 5/2020 | Downes et al. |
| 2020/0347037 A1 | 11/2020 | Lagu et al. |
| 2021/0171494 A1 * | 6/2021 | Lagu ..................... C07D 233/64 |
| 2021/0283116 A1 | 9/2021 | Lagu et al. |

FOREIGN PATENT DOCUMENTS

| | | |
|---|---|---|
| AU | 2007252020 A1 | 11/2007 |
| CN | 101085772 A | 12/2007 |
| EP | 1553075 A1 | 7/2005 |
| EP | 2014652 A1 | 1/2009 |
| EP | 2128138 A1 | 12/2009 |
| JP | 2008-285452 A | 11/2008 |
| JP | 2009-525340 A | 7/2009 |
| WO | 2000/50391 A1 | 8/2000 |
| WO | 2001/12612 A1 | 2/2001 |
| WO | 2002/014285 A1 | 2/2002 |

(Continued)

OTHER PUBLICATIONS

Arnold et al., Inflammatory monocytes recruited after skeletal muscle injury switch into antiinflammatory macrophages to support myogenesis. J Exp Med. May 14, 2007;204(5):1057-69.
Bräuer et al., Evolutionary chemistry approach toward finding novel inhibitors of the type 2 diabetes target glucose-6-phosphate translocase. J Comb Chem. Mar.-Apr. 2005;7(2):218-26.
Chemical Abstracts Plus, Accession No. 2000:737780, STN entry dated Oct. 19, 2000, and CAS Registry No. 312958-87-5.
Ciocoiu et al., Synthesis and dual PPARalpha/delta agonist effects of 1,4-disubstituted 1,2,3-triazole analogues of GW 501516. Eur J Med Chem. Jul. 2010;45(7):3047-55.
Ciocoiu et al., Synthesis, Biological Evaluation and Molecular Modeling of GW 501516 Analogues. Arch Pharm Chem Life Sci. 2010;10:612-624.
Ciocoiu et al., Synthesis, molecular modeling studies and biological evaluation of fluorine substituted analogs of GW 501516. Bioorg Med Chem. Dec. 1, 2011;19(23):6982-8.

(Continued)

*Primary Examiner* — Laura L Stockton

(74) *Attorney, Agent, or Firm* — McCarter & English, LLP; Steven G. Davis; Wei Song

(57) ABSTRACT

Provided herein are compounds and compositions useful in increasing PPARδ activity. The compounds and compositions provided herein are useful for the treatment of PPARδ related diseases (e.g., muscular diseases, vascular disease, demyelinating disease, and metabolic diseases).

16 Claims, 13 Drawing Sheets

(56) References Cited

FOREIGN PATENT DOCUMENTS

| | | | |
|---|---|---|---|
| WO | 2004/020409 A1 | 3/2004 | |
| WO | 2004/060367 A1 | 7/2004 | |
| WO | 2006/027135 A1 | 3/2006 | |
| WO | 2007/028424 A1 | 3/2007 | |
| WO | 2007/030567 A2 | 3/2007 | |
| WO | 2007089857 | 8/2007 | |
| WO | 2007/110237 A2 | 10/2007 | |
| WO | 2007/143951 A1 | 12/2007 | |
| WO | 2009/086526 A2 | 7/2009 | |
| WO | 2014/165827 A1 | 10/2014 | |
| WO | 2015/035171 A1 | 3/2015 | |
| WO | 2016/057322 A1 | 4/2016 | |
| WO | 2016/057658 A1 | 4/2016 | |
| WO | 2017/180818 A1 | 10/2017 | |

OTHER PUBLICATIONS

Jacintho et al., Discovery of potent and seletive PPARalpha/delta dual antagonists and initial biological studies. Bioorganic & Medicinal Chemistry Letters. 6 pages, prepublication version, (2018).

Jonker et al., A PPARgamma-FGF1 axis is required for adaptive adipose remodelling and metabolic homeostasis. Nature. May 17, 2012;485(7398):391-4.

Kim et al., Synthesis and evaluation of an orally available "Y"-shaped biaryl peroxisome proliferator-activated receptor d agonist. Bioorg Med Chem. 8 pages, prepublication version, (2018).

Lagu et al., Highly selective perixisome proliferator-activated receptor delta (PPARdelta) modulator demonstrates improved safety profile to GW501516. Bioorganic & Medicinal Chemistry Letters. 2018;28:533-536.

Lagu et al., Novel highly selective peroxisome proliferator-activated receptor d (PPARd) modulators with pharmacokinetic properties suitable for once-daily oral dosing. Bioorg Med Chem Lett. Dec. 1, 2017;27(23):5230-5234.

Lagu et al., Selective PPARd Modulators Improve Mitochondrial Function: Potential Treatment for Duchenne Muscular Dystrophy (DMD). ACS Med Chem Lett. Jul. 31, 2018;9(9):935-940.

Lee et al., PPARdelta regulates glucose metabolism and insulin sensitivity. Proc Natl Acad Sci U S A. Feb. 28, 2006;103(9):3444-9.

Luquet et al., Peroxisome proliferator-activated receptor delta controls muscle development and oxidative capability. FASEB J. Dec. 2003;17(15):2299-301.

Markert et al., Exercise and Duchenne muscular dystrophy: toward evidence-based exercise prescription. Muscle Nerve. Apr. 2011;43(4):464-78.

Menetrey et al., Growth factors improve muscle healing in vivo. J Bone Joint Surg Br. Jan. 2000;82(1):131-7.

Mitachi et al., Synthesis and structure-activity relationship of disubstituted benzamides as a novel class of antimalarial agents. Bioorg Med Chem Lett. Jul. 15, 2012;22(14):4536-9.

Miura et al., Pharmacological activation of PPARbeta/delta stimulates utrophin A expression in skeletal muscle fibers and restores sarcolemmal integrity in mature mdx mice. Hum Mol Genet. Dec. 1, 2009;18(23):4640-9.

Narkar et al., AMPK and PPARdelta agonists are exercise mimetics. Cell. Aug. 8, 2008;134(3):405-15.

Naruhn et al., High-affinity peroxisome proliferator-activated receptor ß/d-specific ligands with pure antagonistic or inverse agonistic properties. Mol Pharmacol. Nov. 2011;80(5):828-38.

Pettersson et al., Design of a partial PPARdelta agonist. Bioorg Med Chem Lett. Aug. 15, 2007;17(16):4625-9.

Schwarz et al., Monitoring Solution Structures of Peroxisome Proliferator-Activated Receptor beta/d upon Ligand Binding. PLoS One. Mar. 18, 2016;11(3):e0151412. 20 pages.

Shefer et al., Reduced satellite cell numbers and myogenic capacity in aging can be alleviated by endurance exercise. PLoS One. Oct. 12, 2010;5(10):e13307. 11 pages.

Sobolevsky et al., Detection of PPARd agonists GW1516 and GW0742 and their metabolites in human urine. Drug Test Anal. Oct. 2012;4(10):754-60.

Wang et al., Correction: Regulation of muscle fiber type and running endurance by PPARdelta. PLoS Biol. Jan. 2005;3(1):e61. 2 pages.

Wang et al., Peroxisome-proliferator-activated receptor delta activates fat metabolism to prevent obesity. Cell. Apr. 18, 2003;113(2):159-70.

Wang et al., Regulation of muscle fiber type and running endurance by PPARdelta. PLoS Biol. Oct. 2004;2(10):e294. 1532-1539.

Wu et al., Structural basis for specific ligation of the peroxisome proliferator-activated receptor d. Proc Natl Acad Sci U S A Mar. 28, 2017;114(13):E2563-E2570.

Zhang et al., Discovery and SAR of para-alkylthiophenoxyacetic acids as potent and selective PPARdelta agonists. Bioorg Med Chem Lett. Feb. 15, 2009;19(4):1101-4.

International Preliminary Report on Patentability for Application No. PCT/US2015/054475, dated Apr. 20, 2017. 12 pages.

International Search Report and Written Opinion for Application No. PCT/US2014/033088, dated Jul. 22, 2014. 15 pages.

International Search Report and Written Opinion for Application No. PCT/US2016/055521, dated Jan. 2, 2017. 11 page.

International Search Report for Application No. PCT/US2015/054475, dated Dec. 15, 2015. 7 pages.

Singapore Office Action and Written Opinion for Application No. 11201802302S, dated Jan. 29, 2019, 9 pages.

Altinoz et al., PPARdelta and its ligand erucic acid may act anti-tumoral, neuroprotective, and myelin protective in neuroblastoma, glioblastoma, and Parkinson's disease. Mol Aspects Med. Apr. 2021;78:100871, 10 pages.

Gura, Systems for identifying new drugs are often faulty. Science. Nov. 7, 1997;278(5340):1041-2.

Johnson et al., Relationships between drug activity in NCI preclinical in vitro and in vivo models and early clinical trials. Br J Cancer. May 18, 2001;84(10):1424-31.

Kadayat et al., Targeting Peroxisome Proliferator-Activated Receptor Delta (PPARd): A Medicinal Chemistry Perspective. J Med Chem. Sep. 24, 2020;63(18):10109-10134.

Liu et al., The Role of PPAR-delta in Metabolism, Inflammation, and Cancer: Many Characters of a Critical Transcription Factor. Int J Mol Sci. Oct. 26, 2018;19(11):3339, 14 pages.

Millar, Novel benefits of peroxisome proliferator-activated receptors on cardiovascular risk. Curr Opin Lipidol. Jun. 2013;24(3):233-8.

Pearce et al., Failure modes in anticancer drug discovery and development. Cancer Drug Design and Discovery. Academic Press, New York. Stephen Neidle (Ed.). Chapter 18, pp. 424-435, (2008).

Schnegg et al., Neuroprotective Mechanisms of PPARd: Modulation of Oxidative Stress and Inflammatory Processes. PPAR Res. 2011;2011:373560, 10 pages.

Simone, Introduction. Cecil Textbook of Medicine, vol. 1, 20th Edition. W.B. Saunders Company, Philadelphia. J. Claude Bennett (Ed.). pp. 1004-1010, (1996).

Takada et al., Peroxisome proliferator-activated receptor agonists and antagonists: a patent review (2014-present). Expert Opin Ther Pat. Jan. 2020;30(1):1-13.

\* cited by examiner

PPAR AGONISTS, COMPOUNDS, PHARMACEUTICAL COMPOSITIONS, AND METHODS OF USE THEREOF

REFERENCE TO RELATED APPLICATIONS

This application is a continuation application of U.S. application Ser. No. 16/682,676, filed Nov. 13, 2019 (now U.S. Pat. No. 10,906,885), which is a continuation application of U.S. application Ser. No. 16/510,976, filed Jul. 15, 2019 (now U.S. Pat. No. 10,479,775), which is a continuation application of U.S. application Ser. No. 15/766,455, filed Apr. 6, 2018 (now U.S. Pat. No. 10,399,958); which is a U.S. national stage filing, under 35 U.S.C. § 371(c), of International Application No. PCT/US2016/055521, filed Oct. 5, 2016, which claims the benefit of U.S. Provisional Application No. 62/238,629, filed Oct. 7, 2015; U.S. Provisional Application No. 62/243,263, filed Oct. 19, 2015; and U.S. Provisional Application No. 62/352,348, filed Jun. 20, 2016. The entire contents of these applications are incorporated herein by reference.

FIELD

This application concerns agonists of peroxisome proliferator-activated receptors (PPAR), particularly PPAR delta (PPARδ), and methods for their use, such as to treat or prevent one or more PPARδ-related diseases.

BACKGROUND

Peroxisome proliferator-activated receptor delta (PPARδ) is a nuclear receptor that is capable of regulating mitochondria biosynthesis. As shown in PCT/2014/033088, incorporated herein by reference, modulating the activity of PPAR is useful for the treatment of diseases, developmental delays, and symptoms related to mitochondrial dysfunction, such as Alpers Disease, MERRF-Myoclonic epilepsy and ragged-red fiber disease, Pearson Syndrome, and the like. Modulation PPAR activity is effective in the treatment of other conditions, such as muscular diseases, demyelinating diseases, vascular diseases, and metabolic diseases. Indeed, PPAR is an important biological target for compounds used to help treat and prevent mitochondrial diseases, muscle-related diseases and disorders, and other related conditions.

Accordingly, there remains a need in the art for novel compounds capable of effectively and reliably activating PPAR in vitro and in vivo. There is also a need for PPARδ activating compounds with improved pharmacokinetic properties and improved metabolic stability. The present invention addresses these and other such needs.

SUMMARY

Provided herein, inter alia, are compounds and compositions comprising such compounds that are useful for increasing PPARδ activity. In particular, disclosed herein are methods modulating the activity of PPARδ for the treatment of diseases, developmental delays, and symptoms related to mitochondrial dysfunction (see, e.g., Example 1). For example, the disclosed compounds and compositions are useful in the treatment of mitochondrial diseases, such as Alpers Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, and Pearson Syndrome. Alternatively, the disclosed compounds and compositions are useful in the treatment of other PPARδ-related diseases, such as renal diseases, muscular diseases, demyelinating diseases, vascular diseases, and metabolic diseases. For example, example 3 describes the use of Compound 2d to improve mitochondrial biogenesis and function in Duchenne Muscular Dystrophy (DMD) muscle cells. Example 4 describes the use of Compound 2d to increase capacity for endurance exercise in mouse model of Duchenne Muscular Dystrophy. Example 5 describes the use of Compound 2d to reduce dystrophic muscle phenotype in mouse model of Duchenne Muscular Dystrophy. Example 6 describes oral administration of Compounds 2a, 2d, and 2n to reduce ischemia-reperfusion induced kidney injury in rats.

In one embodiment, provided herein is a compound of Formula (I), (II), or (III):

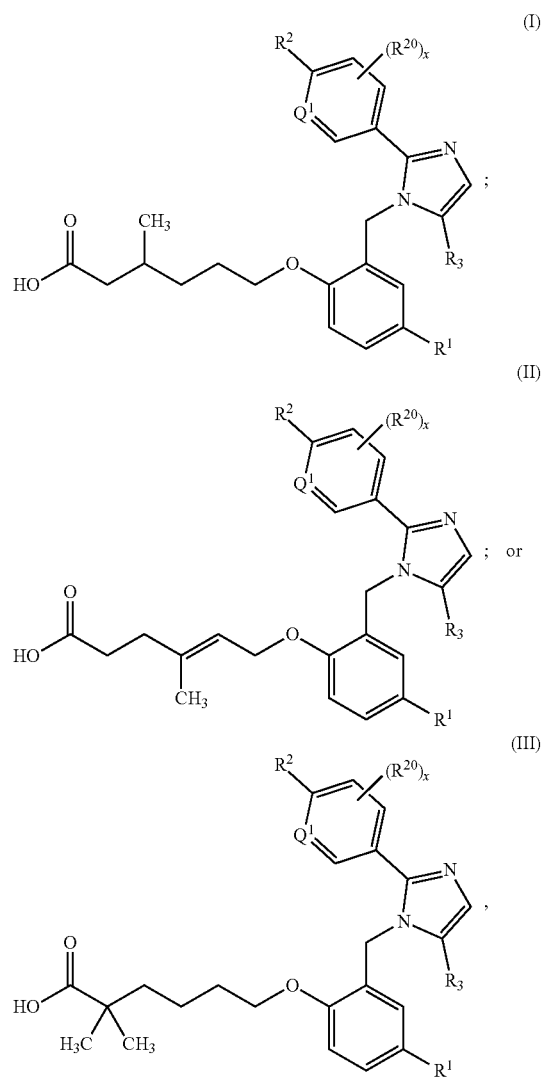

or a pharmaceutically acceptable salt thereof, wherein:

$R^1$ is hydrogen, halogen, —$C_1$-$C_4$-alkyl, —CN, $C_1$-$C_4$-alkoxy, —$C_1$-$C_4$-haloalkoxy, or —$C_3$-$C_6$-cycloalkyl;

$Q^1$ is CH or N;

$R^2$ is hydrogen, halogen, —CN, —$C_1$-$C_4$-alkyl, —$C_1$-$C_4$-haloalkyl, —$C_3$-$C_6$-cycloalkyl, —$C_1$-$C_4$-alkoxy, —$C_1$-$C_4$-haloalkoxy, —S($C_1$-$C_4$-alkyl), —$SO_2$($C_1$-$C_4$-alkyl), 5- or 6-membered heterocycle, aryl, 5-membered heteroaryl, —≡—$R^{2A}$, —O($CH_2$)$_m$$R^{2B}$, —N($C_1$-$C_4$-alkyl)$_2$, or —C(O)($C_1$-$C_4$-alkyl), wherein aryl and heteroaryl are optionally substituted with halogen, —OH, —CN, formyl, acetyl, acetoxy, or carboxy, and wherein m is an integer having value of 1, 2, or 3;

x is an integer having a value of 1 or 2;

$R^{2A}$ and $R^{2B}$ are each independently —$C_1$-$C_4$-alkyl, —$C_1$-$C_4$-haloalkyl, or —$C_3$-$C_6$-cycloalkyl;

each $R^{20}$ is independently hydrogen, halogen, —$C_1$-$C_4$-alkyl, —CN, or —$C_1$-$C_4$-alkoxy; and $R^3$ is —$CH_3$ or -$CD_3$.

Pharmaceutical compositions of compounds of Formula (I), (II), and (III) also are disclosed herein. Particular embodiments comprise a pharmaceutically acceptable carrier or excipient and one or more of the disclosed compounds, or a pharmaceutically acceptable salt thereof. The pharmaceutical compositions of the invention can be used in therapy, e.g., for treating a PPARδ-related disease or condition in a subject.

Another embodiment comprises treating a PPARδ-related disease or condition in a subject by administering to the subject a therapeutically effective amount of one or more disclosed compounds, or a pharmaceutically acceptable salt thereof, or a pharmaceutical composition comprising the compound(s).

Also provided herein is the use of one or more of the disclosed compounds, or a pharmaceutically acceptable salt thereof, or a pharmaceutical composition comprising one or more of the disclosed compounds, for the preparation of a medicament for the treatment of a PPARδ-related disease or condition.

In another embodiment, provided herein the disclosed compounds, or a pharmaceutically acceptable salt thereof, or a pharmaceutical composition comprising one or more of the disclosed compounds are for use in treating a PPARδ-related disease or condition.

DETAILED DESCRIPTION

Figure 1:
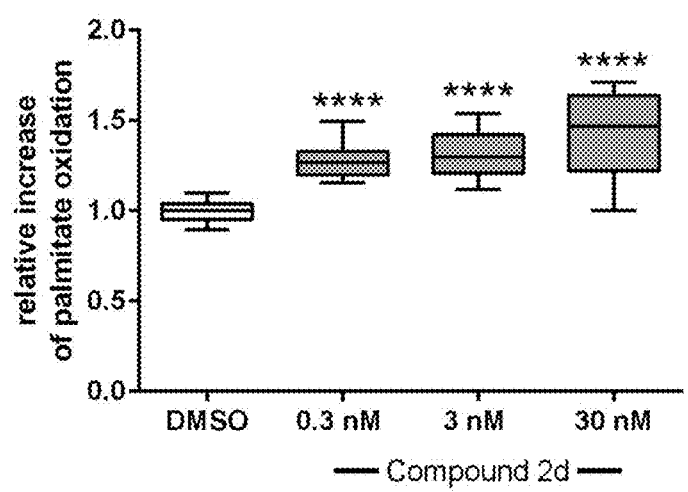
FIG. 1 is a graph showing fatty acid oxidation increases with Compound 2d administration in Duchenne Muscular Dystrophy (DMD) patient cells.

Peroxisome proliferator-activated receptor delta (PPAR-δ), also known as peroxisome proliferator-activated receptor beta (PPAR-β) or as NR1C2 (nuclear receptor subfamily 1, group C, member 2), refers to a nuclear receptor protein that function as a transcription factor regulating the expression of genes. Ligands of PPARδ can promote myoblast proliferation after injury, such as injury to skeletal muscle. PPARδ (OMIM 600409) sequences are publically available, for example from GenBank® sequence database (e.g., accession numbers NP_001165289.1 (human, protein) NP_035275 (mouse, protein), NM_001171818 (human, nucleic acid) and NM 011145 (mouse, nucleic acid)).

Herein, the phrase "PPARδ agonist" refers to substances that increase the activity of PPARδ. Substances can be tested for their PPARδ agonist activity by contacting the substance with cells expressing PPARδ, detecting their binding with PPARδ and then detecting signals that serve as the indicator of the activation of PPARδ.

Definitions

The term "alkyl" used alone or as part of a larger moiety, such as "alkoxy", "haloalkyl", "haloalkoxy", "cycloalkyl", and the like, means saturated aliphatic straight-chain or branched monovalent hydrocarbon radical. Unless otherwise specified, an alkyl group typically has 1 to 4 carbon atoms, i.e., $C_1$-$C_4$-alkyl. As used herein, a "$C_1$-$C_4$-alkyl" group means a radical having from 1 to 4 carbon atoms in a linear or branched arrangement, and includes methyl, ethyl, propyl, isopropyl, butyl, isobutyl, sec-butyl and tert-butyl.

"Alkoxy" means an alkyl radical attached through an oxygen linking atom, represented by —O-alkyl. For example, "$C_1$-$C_4$-alkoxy" includes methoxy, ethoxy, propoxy, isopropoxy and butoxy.

The terms "haloalkyl" and "haloalkoxy" mean alkyl or alkoxy, as the case may be, substituted with one or more halogen atoms. For example, "$C_1$-$C_4$-haloalkyl" includes fluoromethyl, difluoromethyl, trifluoromethyl, chloromethyl, dichloromethyl, bromomethyl, fluoroethyl, difluoroethyl, dichloroethyl and chloropropyl, and "$C_1$-$C_4$-haloalkoxy" includes fluoromethoxy, difluoromethoxy, trifluoromethoxy, chloromethoxy, dichloromethoxy, bromomethoxy, fluoroethoxy, difluoroethoxy, dichloroethoxy and chloropropoxy.

The term "halogen" means fluorine or fluoro (F), chlorine or chloro (Cl), bromine or bromo (Br), or iodine or iodo (I).

Examples of "aryl" include phenyl, naphthyl, anthracenyl, 1,2-dihydronaphthyl, 1,2,3,4-tetrahydronaphthyl, fluorenyl, indanyl and indenyl.

"Cycloalkyl" means a 3-12 membered saturated aliphatic cyclic hydrocarbon radical. It can be monocyclic, bicyclic (e.g., a bridged or fused bicyclic ring), or tricyclic. For example, monocyclic $C_3$-$C_6$-cycloalkyl means a radical having from 3 to 6 carbon atoms arranged in a monocyclic ring. For example, "$C_3$-$C_6$-cycloalkyl" includes, but is not limited to, cyclopropyl, cyclobutyl, cyclopentyl, and cyclohexyl.

"5- or 6-membered heterocycle" means a radical having from 5 or 6 ring atoms (including 1 to 3 ring heteroatoms) arranged in a monocyclic ring. Examples of "5- or 6-membered heterocycle" include, but are not limited to, morpholinyl, thiomorpholinyl, pyrrolidinonyl, pyrrolidinyl, piperidinyl, piperazinyl, hydantoinyl, valerolactamyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl.

"5-membered heteroaryl" means a monocyclic aromatic ring system having five ring atoms selected from carbon and at least one (typically 1 to 3, more typically 1 or 2) heteroatoms (e.g., oxygen, nitrogen or sulfur). Typical examples are 5-membered heteroaryl containing 1 or 2 atoms selected independently from nitrogen atoms, sulfur atoms and oxygen atoms such as pyrrolyl, thienyl, furyl, imidazolyl, pyrazolyl, isothiazolyl, isoxazolyl, and the like.

If a group is described as being "substituted", a non-hydrogen substituent is in the place of hydrogen on a carbon, sulfur or nitrogen of the substituent. Thus, for example, a substituted alkyl is an alkyl wherein at least one non-hydrogen substituent is in the place of hydrogen on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent can be identical or different (unless otherwise stated). A person of ordinary skill in the art will recognize that the compounds and definitions provided do not include impermissible substituent patterns (e.g., methyl substituted with 5 different groups, and the like) Such impermissible substitution patterns are clearly recognized by a person of ordinary skill in the art.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. The term "geometric isomer" refers to compounds having at least one double bond, wherein the double bond(s) may exist in cis, trans syn, anti, entgegen (E), and zusammen (Z) forms as well as mixtures thereof. When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the geometric isomeric purity of the named or depicted geometric isomer is at least 60%, 70%, 80%, 90%, 99%, or 99.9% pure by weight. Geometric isomeric purity is determined by dividing the weight of the named or depicted geometric isomer in the mixture by the total weight of all of the geometric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99%, or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers is at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, nitric, and sulfuric acids) and of organic acids (such as, e.g., acetic acid, benzenesulfonic, benzoic, methanesulfonic, and p-toluenesulfonic acids). For example, in one embodiment the acid addition salt is a hemisulfate salt. Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts), alkaline earth metal salts (such as magnesium and calcium salts) and organic base salts (such as meglumine salt).

As used herein, the term "pharmaceutically-acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically-acceptable salts are well known in the art. For example, S. M. Berge, et al. describes pharmacologically acceptable salts in *J. Pharm. Sci.*, 1977, 66:1-19.

The neutral forms of the compounds of the invention are regenerated from their corresponding salts by contacting the salt with a base or acid and isolating the parent compound in the conventional manner. The parent form of the compound may differ from the various salt forms in certain physical properties, such as solubility in polar solvents. The neutral forms of compounds disclosed herein also are included in the invention.

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

The term "effective amount" or "therapeutically effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., from 1 mg to about 50 g per day, e.g., from 1 mg to about 5 grams per day).

The particular mode of administration and the dosage regimen will be selected by the attending clinician, taking into account the particulars of the case (e.g., the subject, the disease, the disease state involved, the particular treatment, and whether the treatment is prophylactic). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a PPARδ related disease using the disclosed PPAR agonists for guidance.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject.

Non-limiting examples of pharmaceutically acceptable carriers and excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical carriers and excipients are suitable for use with disclosed compounds.

Compounds of the Invention

Disclosed herein are embodiments of a compound having general Formula (I), (II), or (III):

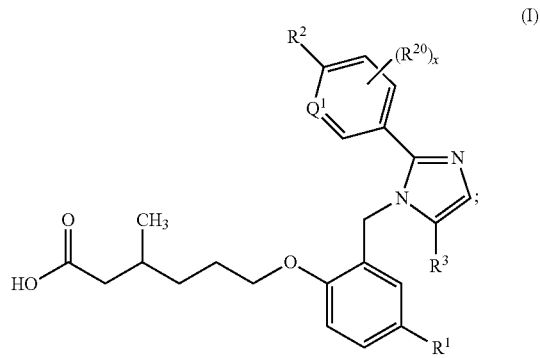

(I)

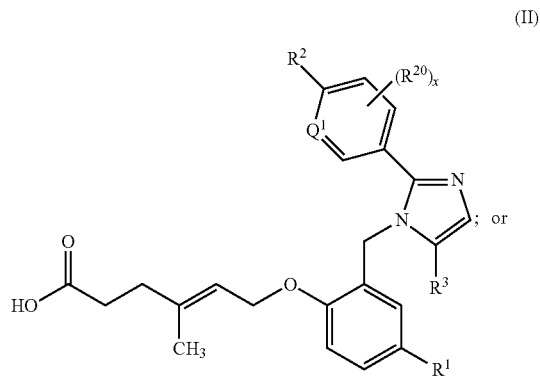

(II)

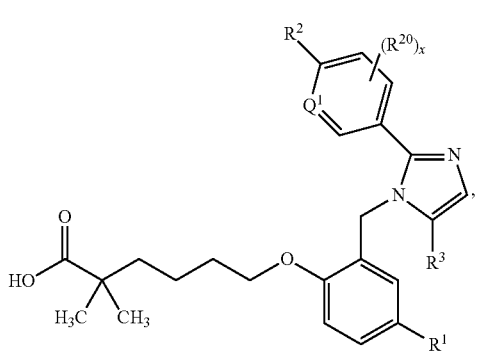

or a pharmaceutically acceptable salt thereof,
wherein:
$R^1$ is hydrogen, halogen, —$C_1$-$C_4$-alkyl, —CN, —$C_1$-$C_4$-haloalkoxy, or —$C_3$-$C_6$-cycloalkyl;
$Q^1$ is CH or N;
$R^2$ is hydrogen, halogen, —CN, —$C_1$-$C_4$-alkyl, —$C_1$-$C_4$-haloalkyl, —$C_3$-$C_6$-cycloalkyl, alkoxy, —$C_1$-$C_4$-haloalkoxy, —$SO_2(C_1$-$C_4$-alkyl), 5- or 6-membered heterocycle, aryl, 5-membered heteroaryl, =—$R^{2A}$, —$O(CH_2)_mR^{2B}$, —$N(C_1$-$C_4$-alkyl)$_2$, or —$C(O)(C_1$-$C_4$-alkyl), wherein aryl and heteroaryl are optionally substituted with halogen, —OH, —CN, formyl, acetyl, acetoxy, or carboxy, and wherein m is an integer having value of 1, 2, or 3;
x is an integer having a value of 1 or 2;
$R^{2A}$ and $R^{2B}$ are each independently —$C_1$-$C_4$-alkyl, —$C_1$-$C_4$-haloalkyl, or —$C_3$-$C_6$-cycloalkyl;
each $R^{20}$ is independently hydrogen, halogen, —$C_1$-$C_4$-alkyl, —CN, or —$C_1$-$C_4$-alkoxy; and
$R^3$ is $CH_3$ or $CD_3$.

In a $1^{St}$ embodiment, the compound has the structure of Formula (I), (II), or (III), wherein $R^3$ is $CH_3$, and the remaining variables are the same as defined above.

In a $2^{nd}$ embodiment, the compound has the structure of Formula (Ia), (IIa), or (IIIa):

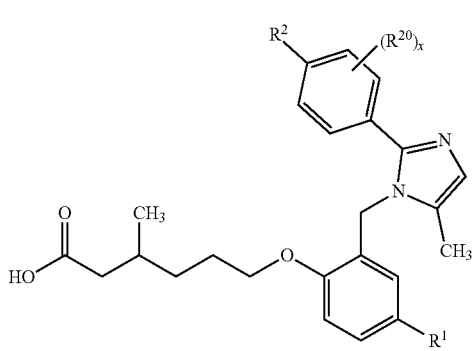

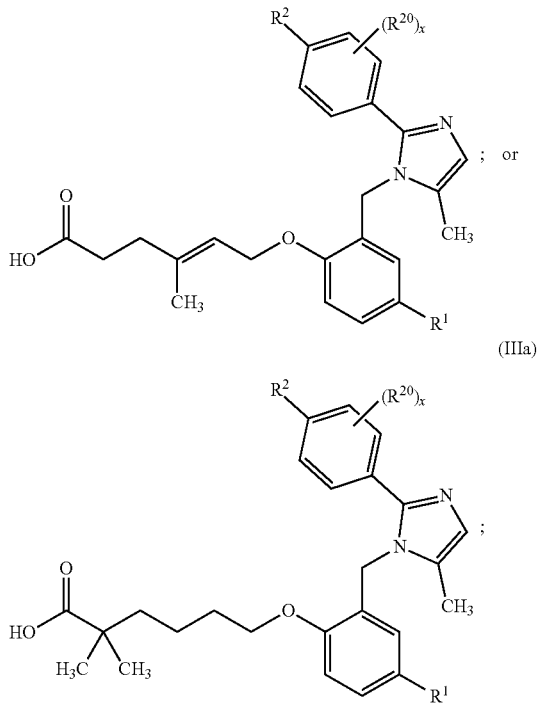

or a pharmaceutically acceptable salt thereof, wherein the variables are as defined for Formulas (I), (II), and (III).

In a $3^{rd}$ embodiment, the compound the compound has the structure of Formula (Iaa):

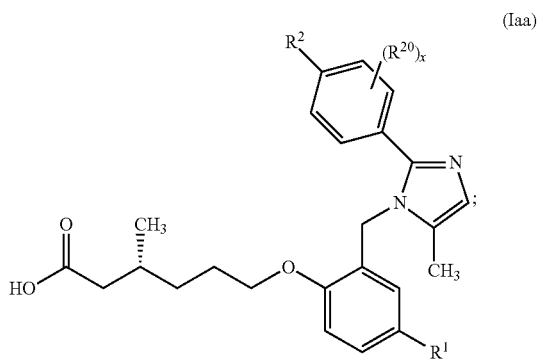

or, alternatively, the structure of Formula (Iaa'):

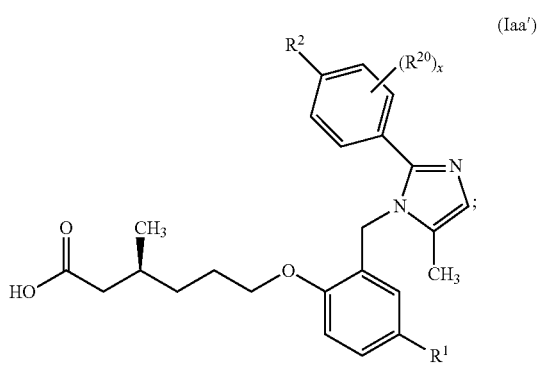

or a pharmaceutically acceptable salt thereof, wherein the variables are as defined in the 1st embodiment.

In a 4th embodiment, the compound has the structure of Formula (Ib), (IIb) or (IIIb):

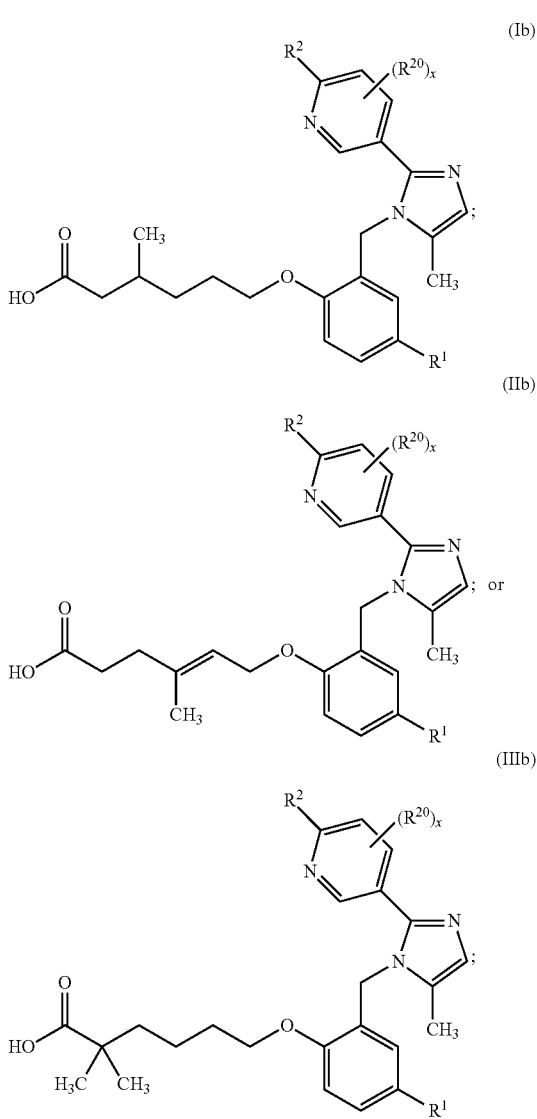

or a pharmaceutically acceptable salt thereof, wherein the variables are as defined in the 1st embodiment.

In a 5th embodiment, the compound the compound has the structure of Formula (Ibb):

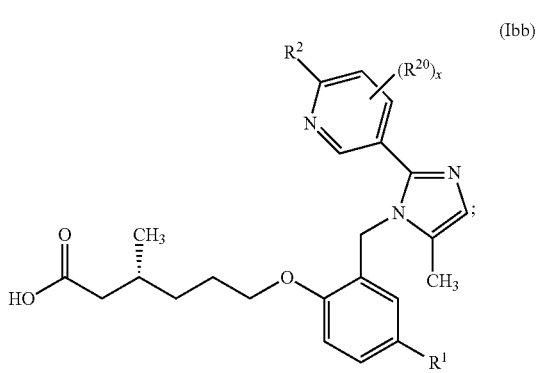

or, alternatively, the structure of Formula (Ibb'):

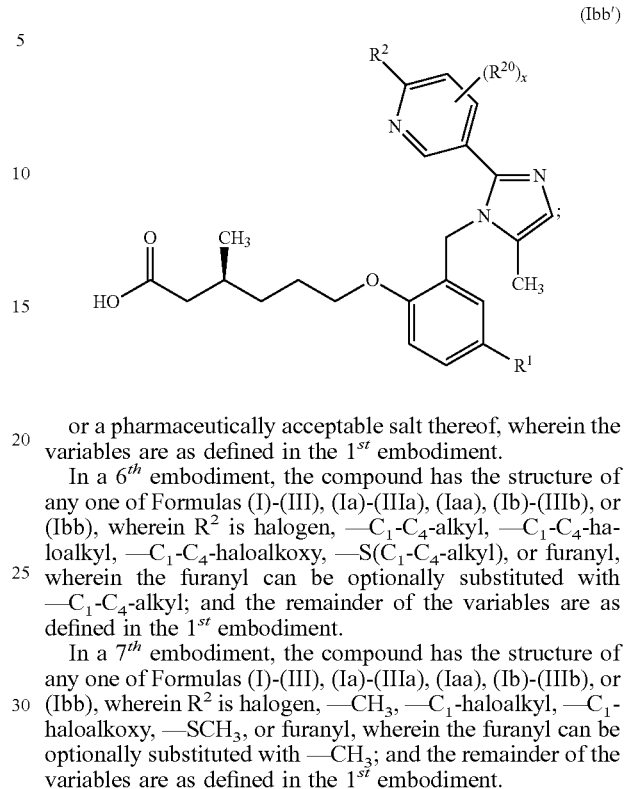

or a pharmaceutically acceptable salt thereof, wherein the variables are as defined in the 1st embodiment.

In a 6th embodiment, the compound has the structure of any one of Formulas (I)-(III), (Ia)-(IIIa), (Iaa), (Ib)-(IIIb), or (Ibb), wherein $R^2$ is halogen, —$C_1$-$C_4$-alkyl, —$C_1$-$C_4$-haloalkyl, —$C_1$-$C_4$-haloalkoxy, —$S(C_1$-$C_4$-alkyl), or furanyl, wherein the furanyl can be optionally substituted with —$C_1$-$C_4$-alkyl; and the remainder of the variables are as defined in the 1st embodiment.

In a 7th embodiment, the compound has the structure of any one of Formulas (I)-(III), (Ia)-(IIIa), (Iaa), (Ib)-(IIIb), or (Ibb), wherein $R^2$ is halogen, —$CH_3$, —$C_1$-haloalkyl, —$C_1$-haloalkoxy, —$SCH_3$, or furanyl, wherein the furanyl can be optionally substituted with —$CH_3$; and the remainder of the variables are as defined in the 1st embodiment.

In a 8th embodiment, the compound has the structure of any one of Formulas (I)-(III), (Ia)-(IIIa), (Iaa), (Ib)-(IIIb), or (Ibb), wherein $R^2$ is halogen, —$CH_3$, —$C_1$-haloalkyl, —$C_1$-haloalkoxy, or —$SCH_3$, and the remainder of the variables are as defined in the 1st embodiment.

In an 9th embodiment, the compound has the structure of any one of Formulas (I)-(III), (Ia)-(IIIa), (Iaa), (Ib)-(IIIb), or (Ibb), wherein $R^2$ is chloro, unsubstituted furanyl, —$CH_3$, —$CF_3$, —$OCF_3$, —$OCHF_2$, or —$SCH_3$, and the remainder of the variables are as defined in the 1st embodiment.

In a 10th embodiment, the compound has the structure of any one of Formulas (I)-(III), (Ia)-(IIIa), (Iaa), (Ib)-(IIIb), or (Ibb), wherein $R^2$ is —$CF_3$ or —$OCF_3$, and the remainder of the variables are as defined in the 1st embodiment.

In an 11th embodiment, the compound has the structure of any one of Formulas (I)-(III), (Ia)-(IIIa), (Iaa), (Ib)-(IIIb), or (Ibb), wherein $R^2$ is —$CF_3$, and the remainder of the variables are as defined in the 1st embodiment.

In a 12th embodiment, the compound has the structure of any one of Formulas (I)-(III), (Ia)-(IIIa), (Iaa), (Ib)-(IIIb), or (Ibb), wherein $R^1$ is hydrogen or halogen; and the remainder of the variables are as defined in the 1st, 6th, 7th, 8th, 9th, 10th, or 11th embodiment.

In a 13th embodiment, the compound has the structure of any one of Formulas (I)-(III), (Ia)-(IIIa), (Iaa), (Ib)-(IIIb), or (Ibb), wherein $R^1$ is hydrogen or fluoro; and the remainder of the variables are as defined in the 1st, 6th, 7th, 8th, 9th, 10th, or 11th embodiment.

In a 14th embodiment, the compound has the structure of any one of Formulas (I)-(III), (Ia)-(IIIa), (Iaa), (Ib)-(IIIb), or (Ibb), wherein each $R^{20}$ is independently hydrogen or halogen; and the remainder of the variables are as defined in the 1st, 6th, 7th, 8th, 9th, 10th, 11th, 12th, or 13th embodiment.

In a 15th embodiment, the compound has the structure of any one of Formulas (I)-(III), (Ia)-(IIIa), (Iaa), (Ib)-(IIIb), or (Ibb), wherein $R^{20}$ is hydrogen or fluoro; and the remainder of the variables are as defined in the 1st, 6th, 7th, 8th, 9th, 10th, 11th, 12th, or 13th embodiment.

In a 16th embodiment, the compound has the structure of any one of Formula (Iaa) or (Ibb), wherein $R^1$ is hydrogen or fluoro, $R^2$ is $C_1$-$C_4$-haloalkyl or $C_1$-$C_4$-haloalkoxy, $R^{20}$ is hydrogen, and x is an integer having a value of 1.

In a 17th embodiment, the compound has the structure of any one of Formula (Iaa) or (Ibb), wherein $R^1$ is hydrogen, $R^2$ is trifluoromethyl or trifluoromethoxy, $R^{20}$ is hydrogen, and x is an integer having a value of 1.

In certain embodiments, the invention is any one of the compounds depicted in the exemplification section of the instant application; pharmaceutically acceptable salts as well as the neutral forms of these compounds also are included in the invention. Specifically, disclosed embodiments concern is any one of the compounds depicted in Examples 2a-2u; pharmaceutically acceptable salts as well as the neutral forms of these compounds also are included in the disclosed embodiments. In preferred embodiments, disclosed embodiments concern any one of Compounds 2a-2u; pharmaceutically acceptable salts as well as the neutral forms of these compounds also are included in the disclosed embodiments.

Another embodiment of the invention is hydrates or other solvates of the compounds disclosed herein, such as ethanolates, and crystal polymorph substances of any one of the compound of the formula (I), (II) and (III) or a pharmaceutically acceptable salt thereof.

Methods of Preparing Compounds of the Invention

Methods of preparing compounds of Formula (I), (II), and (III) are disclosed. In general, a compound of Formula (I), wherein $R^3$ is —$CH_3$, may be prepared by reacting a compound of Formula (IV)

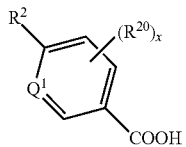

(IV)

with prop-2-yn-1amine to afford a compound of Formula (V):

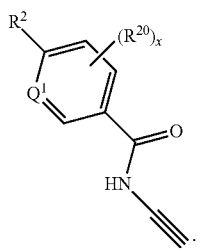

(V)

The compound of Formula (V) can be subsequently reacted with 2-methoxybenzylamine to afford a compound of Formula (VI):

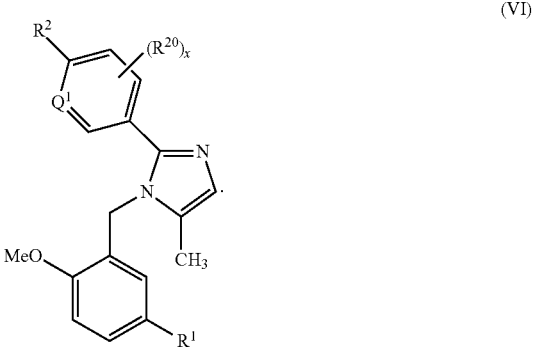

(VI)

The compound of Formula (IV) then can be subjected to demethylation conditions to afford a compound of Formula (VII):

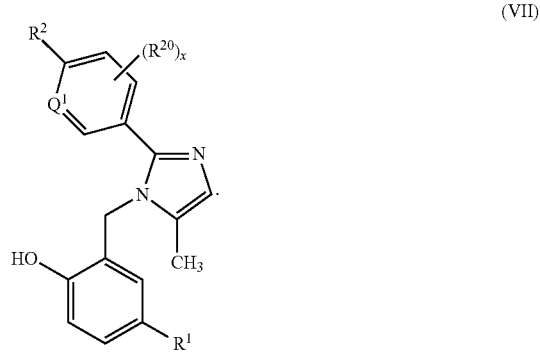

(VII)

The compound of Formula (VII) can be reacted with (R)-ethyl 6-bromo-3-methylhexanoate to afford a compound of formula (VIII):

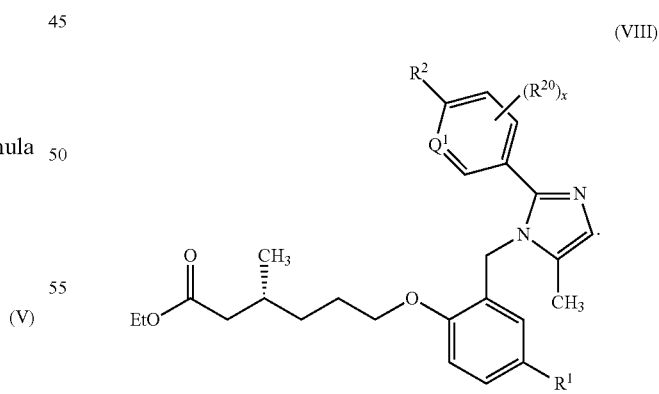

(VIII)

Subsequently, the compound of Formula (VII) may be subjected to hydrolysis conditions to afford the compound of Formula (I).

Similarly, a compound of Formula (II) may be prepared by reacting a compound of Formula (VII) with (E)-ethyl 6-bromo-4-methylhex-4-enoate to afford a compound of Formula (IX):

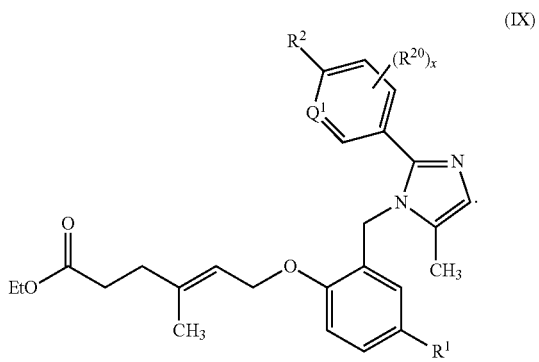

Subsequent hydrolysis of the compound of Formula (IX) affords the compound of Formula (II).

Likewise, a compound of Formula (III) may be prepared by reacting a compound of Formula (VII) with (E)-ethyl 6-bromo-2,2-dimethylhex-4-enoate to afford a compound of Formula (X):

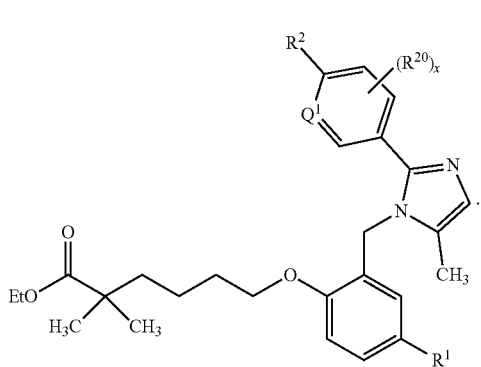

Subsequent hydrolysis of the compound of Formula (X) affords the compound of Formula (III).

Detailed synthetic protocols for preparing exemplary compounds of Formula (I), (II), and (III) are presented in Examples 2a-2u.

Methods of Treatment

Methods of treating a PPARδ-related disease or condition in a subject are disclosed. The methods can include administering to the subject a therapeutically effective amount of one or more compounds or compositions provided herein.

In one embodiment, the PPARδ-related disease is a mitochondrial disease. Examples of mitochondrial diseases include, but are not limited to, Alpers Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, and Pearson Syndrome.

In other embodiments, the PPARδ-related disease is a vascular disease (such as a cardiovascular disease or any disease that would benefit from increasing vascularization in tissues exhibiting impaired or inadequate blood flow). In other embodiments, the PPARδ-related disease is a muscular disease, such as a muscular dystrophy. Examples of muscular dystrophy include but are not limited to Duchenne muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

In some embodiments, the PPARδ-related disease or condition is a demyelinating disease, such as multiple sclerosis, Charcot-Marie-Tooth disease, Pelizaeus-Merzbacher disease, encephalomyelitis, neuromyelitis optica, adrenoleukodystrophy, or Guillian-Barre syndrome.

In other embodiments, the PPARδ-related disease is a metabolic disease. Examples of metabolic diseases include but are not limited to obesity, hypertriglyceridemia, hyperlipidemia, hypoalphalipoproteinemia, hypercholesterolemia, dyslipidemia, Syndrome X, and Type II diabetes mellitus.

In yet other embodiments, the PPARδ-related disease is a muscle structure disorder. Examples of a muscle structure disorders include, but are not limited to, Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, and stress urinary incontinence.

In still other embodiments, the PPARδ-related disease is a neuronal activation disorder, Examples of neuronal activation disorders include, but are not limited to, amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder.

In other embodiments, the PPARδ-related disease is a muscle fatigue disorder. Examples of muscle fatigue disorders include, but are not limited to chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, and thyrotoxic myopathy.

In some embodiments, the PPARδ-related disease is a muscle mass disorder. Examples of muscle mass disorders include, but are not limited to, cachexia, cartilage degeneration, cerebral palsy, compartment syndrome, critical illness myopathy, inclusion body myositis, muscular atrophy (disuse), sarcopenia, steroid myopathy, and systemic lupus erythematosus.

In other embodiments, the PPARδ-related disease is a beta oxidation disease. Examples of beta oxidation diseases include, but are not limited to, systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and riboflavin-responsive disorders of β-oxidation (RR-MADD).

In some embodiments, the PPARδ-related disease is a vascular disease. Examples of vascular diseases include, but are not limited to, peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy.

In other embodiments, the PPARδ-related disease is an ocular vascular disease. Examples of ocular vascular diseases include, but are not limited to, age-related macular degeneration (AMD), stargardt disease, hypertensive retinopathy, diabetic retinopathy, retinopathy, macular degeneration, retinal haemorrhage, and glaucoma.

In yet other embodiments, the PPARδ-related disease is a muscular eye disease. Examples of muscular eye diseases include, but are not limited to, strabismus (crossed eye/wandering eye/walleye ophthalmoparesis), progressive external ophthalmoplegia, esotropia, exotropia, a disorder of refraction and accommodation, hypermetropia, myopia, astigmatism, anisometropia, presbyopia, a disorders of accommodation, or internal ophthalmoplegia.

In yet other embodiments, the PPARδ-related disease is a metabolic disease. Examples of metabolic disorders include, but are not limited to, hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, non-alcoholic fatty liver disease (NAFLD), nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis.

In still other embodiments, the PPARδ-related disease is cancer. Examples of cancer include, but are not limited to, cancers of the colon, large intestine, skin, breast, prostate, ovary, and/or lung.

In other embodiments, the PPARδ-related disease is an ischemic injury. Examples of ischemic injuries include, but are not limited to, cardiac ischemia, such as myocardial infarction; brain ischemia (e.g., acute ischemic stroke; chronic ischemic of the brain, such as vascular dementia; and transient ischemic attack (TIA); bowel ischemia, such as ischemic colitis; limb ischemia, such as acute arm or leg ischemia; subcutaneous ischemia, such as cyanosis or gangrene; and ischemic organ injury, such as ischemic renal injury (IRI).

In still other embodiments, the PPARδ-related disease is a renal disease. Examples of renal diseases include, but are not limited to, glomerulonephritis, glomerulosclerosis, nephrotic syndrome, hypertensive nephrosclerosis, acute nephritis, recurrent hematuria, persistent hematuria, chronic nephritis, rapidly progressive nephritis, acute kidney injury (also known as acute renal failure), chronic renal failure, diabetic nephropathy, or Bartter's syndrome. PCT/US2014/033088, incorporated herein by reference, demonstrates genetic and pharmacological activation of PPARδ promotes muscle regeneration in an acute thermal injury mouse model. Accordingly, use of PPARδ as a therapeutic target to enhance regenerative efficiency of skeletal muscle is also provided.

Pharmaceutical Compositions and Administration Thereof

Additional Therapeutic Agents

Pharmaceutical compositions are disclosed that include one or more compounds provided herein (such as 1, 2, 3, 4, or 5 of such compounds), and typically at least one additional substance, such as an excipient, a known therapeutic other than those of the present disclosure, and combinations thereof. In some embodiments, the disclosed PPAR agonists can be used in combination with other agents known to have beneficial activity with the disclosed PPAR agonists. For example, disclosed compounds can be administered alone or in combination with one or more other PPAR agonists, such as a thiazolidinedione, including rosiglitazone, pioglitazone, troglitazone, and combinations thereof, or a sulfonylurea agent or a pharmaceutically acceptable salt thereof, such as tolbutamide, tolazamide, glipizide, carbutamide, glisoxepide, glisentide, glibornuride, glibenclamide, gliquidone glimepiride, gliclazide and the pharmaceutically acceptable salts of these compounds, or muraglitazar, farglitazar, naveglitazar, netoglitazone, rivoglitazone, K-111, GW-677954, (–)-Halofenate, acid, arachidonic acid, clofbrate, gemfibrozil, fenofibrate, ciprofibrate, bezafibrate, lovastatin, pravastatin, simvastatin, mevastatin, fluvastatin, indomethacin, fenoprofen, ibuprofen, and the pharmaceutically acceptable salts of these compounds.

In one embodiment, disclosed compounds may be administered in combination with dexamphetamine, amphetamine, mazindole or phentermine; and administered in combination with medicaments having an anti-inflammatory effect.

Further, when used for the treatment of a metabolic condition, the pharmaceutical compositions provided herein can be administered as a combination therapy with one or more pharmacologically active substances having favorable effects on metabolic disturbances or disorders. For example, the disclosed pharmaceutical compositions may be administered in combination with RXR agonists for treating metabolic and cardiovascular diseases medicaments, which lower blood glucose; antidiabetics, such as insulins and insulin derivatives, including Lantus, Apidra, and other fast-acting insulins, and GLP-1 receptor modulators; active ingredients for treating dyslipidemias; anti-atherosclerotic medicaments; anti-obesity agents; anti-inflammatory active ingredients; active ingredients for treating malignant tumors; anti-thrombotic active ingredients; active ingredients for treating high blood pressure; active ingredients for treating heart failure, and combinations thereof.

Methods of Administration

The precise amount of compound administered to provide a therapeutically effective amount to the subject will depend on the mode of administration, the type, and severity of the disease and/or condition and on the characteristics of the subject, such as general health, age, sex, body weight, and tolerance to drugs. One of ordinary skill in the art will be able to determine appropriate dosages depending on these and other factors. When administered in combination with other therapeutic agents, a "therapeutically effective amount" of any additional therapeutic agent(s) will depend on the type of drug used. Suitable dosages are known for approved therapeutic agents and can be adjusted by one of ordinary skill in the art according to the condition of the subject, the type of condition(s) being treated and the amount of a compound of the invention being used by following, for example, dosages reported in the literature and recommended in the *Physician's Desk Reference* (57th ed., 2003). For example, a therapeutically effective amount can be given in unit dosage form (e.g., 0.1 mg to about 50 g per day).

The disclosed PPARδ agonists can be administered to a subject by routes known to one of skill in the art. Examples of routes of administration include, but are not limited to, parenteral, e.g., intravenous, intradermal, subcutaneous, oral, intranasal (e.g., inhalation), transdermal, topical, transmucosal, and rectal administration. An exemplary method for oral administration of the compounds of the invention is shown for Compound 2a, Compound 2d, and Compound 2n herein (see Example 6). Exemplary methods for intravenous administration of the compounds of the invention is described in U.S. Provisional Application No. 62/404,390, incorporated herein by reference.

Administration of therapeutic agents by intravenous formulation is well known in the pharmaceutical industry. Intravenous formulations comprise the pharmaceutically active agent dissolved in a pharmaceutically acceptable solvent or solution, such as sterile water, normal saline solutions, lactated Ringer's, or other salt solutions such as Ringer's solution.

An oral formulation typically is prepared as a compressed preparation in, for example, the form of a tablet or pill. A tablet may contain, for example, about 5-10% of the active ingredient (e.g., a salt of Formula (I), (II), or (III)); about 80% of fillers, disintegrants, lubricants, glidants, and binders; and 10% of compounds which ensure easy disintegration, disaggregation, and dissolution of the tablet in the stomach or the intestine. Pills can be coated with sugar, varnish, or wax to disguise the taste.

EXEMPLIFICATION

Example 1a

PPARδ Activity Screen

Cell Culture and Transfection: CV-1 cells were grown in DMEM+10% charcoal stripped FCS. Cells were seeded into 384-well plates the day before transfection to give a confluency of 50-80% at transfection. A total of 0.8 g DNA containing 0.64 micrograms pCMX-PPARDelta LBD, 0.1 micrograms pCMX.beta.Gal, 0.08 micrograms pGLMH2004 reporter and 0.02 micrograms pCMX empty vector was transfected per well using FuGene transfection reagent according to the manufacturer's instructions (Roche). Cells were allowed to express protein for 48 h followed by addition of compound.

Plasmids: Human PPARδ was used to PCR amplify the PPARδ LBD. The amplified cDNA ligand binding domain (LBD) of PPARδ isoform was (PPARδ amino acid 128 to C-terminus) and fused to the DNA binding domain (DBD) of the yeast transcription factor GAL4 by subcloning fragments in frame into the vector pCMX GAL (Sadowski et al. (1992), Gene 118, 137) generating the plasmids pCMX-PPARDelta LBD. Ensuing fusions were verified by sequencing. The pCMXMH2004 luciferase reporter contains multiple copies of the GAL4 DNA response element under a minimal eukaryotic promoter (Hollenberg and Evans, 1988). pCMXβGal was generated.

Compounds: All compounds were dissolved in DMSO and diluted 1:1000 upon addition to the cells. Compounds were tested in quadruple in concentrations ranging from 0.001 to 100 μM. Cells were treated with compound for 24 h followed by luciferase assay. Each compound was tested in at least two separate experiments.

Luciferase assay: Medium including test compound was aspirated and washed with PBS. 50 μl PBS including 1 mM Mg++ and Ca++ were then added to each well. The luciferase assay was performed using the LucLite kit according to the manufacturer's instructions (Packard Instruments). Light emission was quantified by counting on a Perkin Elmer Envision reader. To measure 3-galactosidase activity 25 μl supernatant from each transfection lysate was transferred to a new 384 microplate. Beta-galactosidase assays were performed in the microwell plates using a kit from Promega and read in a Perkin Elmer Envision reader. The beta-galactosidase data were used to normalize (transfection efficiency, cell growth etc.) the luciferase data.

Statistical Methods: The activity of a compound is calculated as fold induction compared to an untreated sample. For each compound the efficacy (maximal activity) is given as a relative activity compared to GW501516, a PPARδ agonist. The $EC_{50}$ is the concentration giving 50% of maximal observed activity. $EC_{50}$ values were calculated via non-linear regression using GraphPad PRISM (GraphPad Software, San Diego, Calif.).

TABLE 1

| | PPARdelta Activity Screen | | |
|---|---|---|---|
| Compound | Structure | Mol. Wt | PPAR delta transactivation EC50 (nM) |
| Compound 2a | | 476.50 | 1.00 |

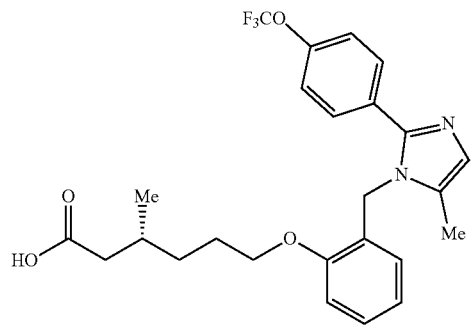 [SMILES: Cc1cnc(-c2ccc(OC(F)(F)F)cc2)n1Cc1ccccc1OCCC[C@@H](C)CC(=O)O]

TABLE 1-continued

| | PPARdelta Activity Screen | | |
|---|---|---|---|
| Compound | Structure | Mol. Wt | PPAR delta transactivation EC50 (nM) |
| Compound 2b | *(structure: 3-methyl-6-[2-((2-(4-chlorophenyl)-5-methyl-1H-imidazol-1-yl)methyl)phenoxy]hexanoic acid)* | 426.93 | 7.80 |
| Compound 2c | *(structure: 3-methyl-6-[2-((2-(4-(furan-2-yl)phenyl)-5-methyl-1H-imidazol-1-yl)methyl)phenoxy]hexanoic acid)* | 458.54 | 3.70 |
| Compound 2d | *(structure: 3-methyl-6-[2-((2-(4-trifluoromethylphenyl)-5-methyl-1H-imidazol-1-yl)methyl)phenoxy]hexanoic acid)* | 460.41 | 0.10 |
| Compound 2e | *(structure: 4-methyl-6-[2-((2-(4-trifluoromethoxyphenyl)-5-methyl-1H-imidazol-1-yl)methyl)phenoxy]hex-4-enoic acid)* | 474.47 | 0.20 |

TABLE 1-continued
PPARdelta Activity Screen
| Compound | Structure | Mol. Wt | PPAR delta transactivation EC50 (nM) |
|---|---|---|---|
| Compound 2f | 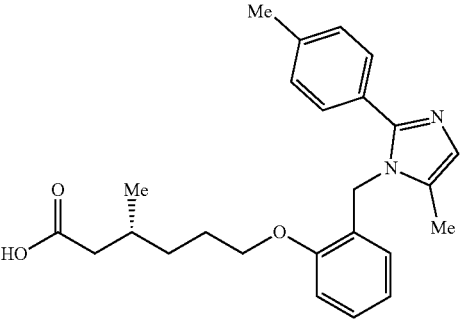 [SMILES: Cc1cnc(-c2ccc(C(F)(F)F)cc2)n1Cc1ccccc1OCCC[C@@H](C)CC(=O)O] | 406.52 | 24.30 |
| Compound 2g | 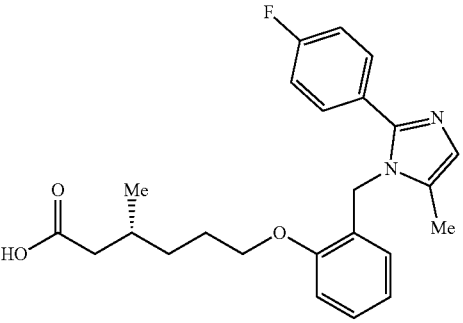 [SMILES: Cc1cnc(-c2ccc(F)cc2)n1Cc1ccccc1OCCC[C@@H](C)CC(=O)O] | 410.48 | 39.00 |
| Compound 2h | 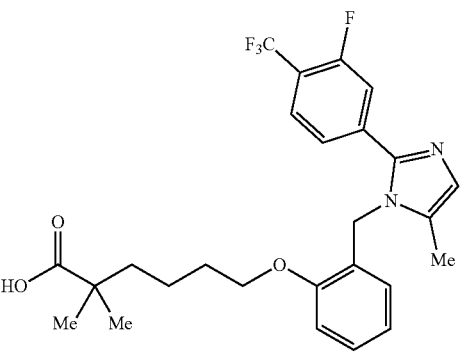 [SMILES: Cc1cnc(-c2ccc(C(F)(F)F)c(F)c2)n1Cc1ccccc1OCCCCC(C)(C)C(=O)O] | 492.50 | 3.50 |
| Compound 2i | 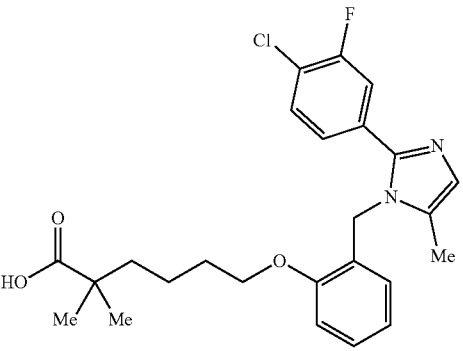 [SMILES: Cc1cnc(-c2ccc(Cl)c(F)c2)n1Cc1ccccc1OCCCCC(C)(C)C(=O)O] | 458.95 | 18.80 |

TABLE 1-continued

PPARdelta Activity Screen

| Compound | Structure | Mol. Wt | PPAR delta transactivation EC50 (nM) |
|---|---|---|---|
| Compound 2j | 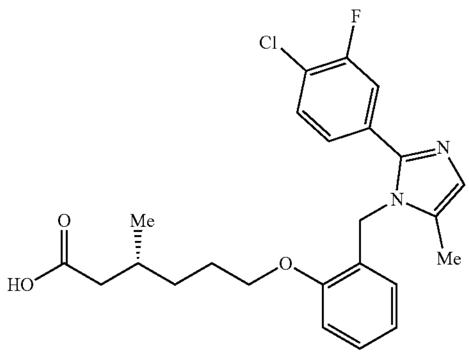 [SMILES: Cc1cnc(-c2ccc(Cl)c(F)c2)n1Cc1ccccc1OCCC[C@@H](C)CC(=O)O] | 444.93 | 0.80 |
| Compound 2k | 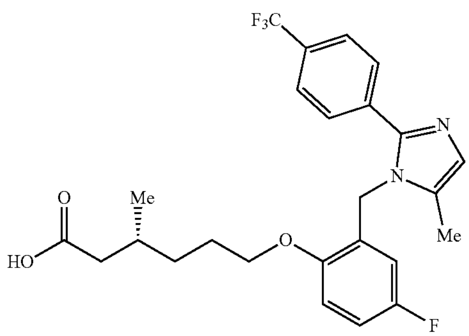 [SMILES: Cc1cnc(-c2ccc(C(F)(F)F)cc2)n1Cc1cc(F)ccc1OCCC[C@@H](C)CC(=O)O] | 478.47 | 6.60 |
| Compound 2l | 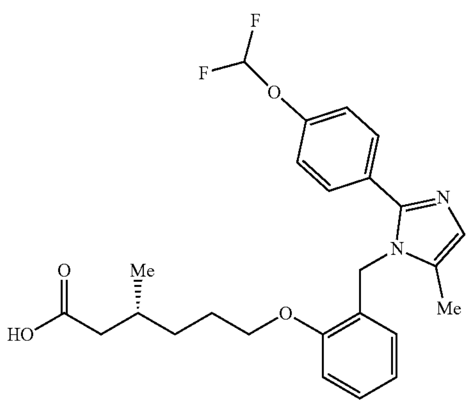 [SMILES: Cc1cnc(-c2ccc(OC(F)F)cc2)n1Cc1ccccc1OCCC[C@@H](C)CC(=O)O] | 458.50 | 13.50 |
| Compound 2m | 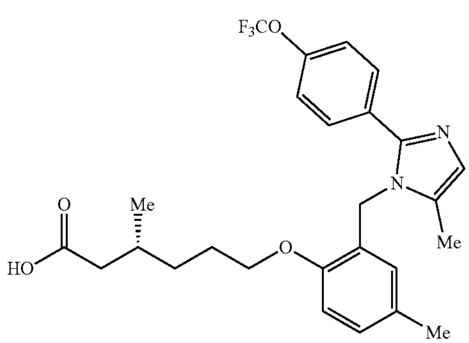 [SMILES: Cc1ccc(OCCC[C@@H](C)CC(=O)O)c(Cn2c(C)cnc2-c2ccc(OC(F)(F)F)cc2)c1] | 490.51 | 0.50 |

TABLE 1-continued

PPARdelta Activity Screen

| Compound | Structure | Mol. Wt | PPAR delta transactivation EC50 (nM) |
|---|---|---|---|
| Compound 2n | 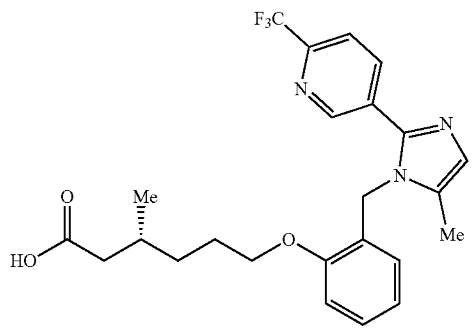 | 461.49 | 4.40 |
| Compound 2o | 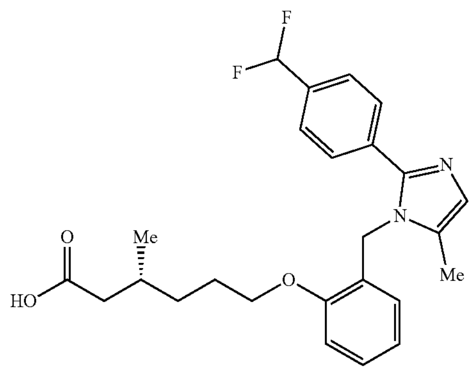 [SMILES: Cc1cnc(-c2ccc(C(F)F)cc2)n1Cc1ccccc1OCCC[C@@H](C)CC(=O)O] | 442.50 | 9.90 |
| Compound 2p | 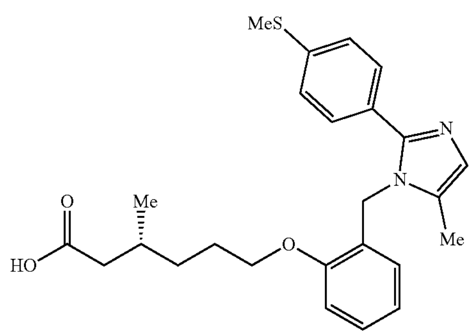 [SMILES: CSc1ccc(-c2ncc(C)n2Cc2ccccc2OCCC[C@@H](C)CC(=O)O)cc1] | 438.58 | 13.10 |
| Compound 2q | 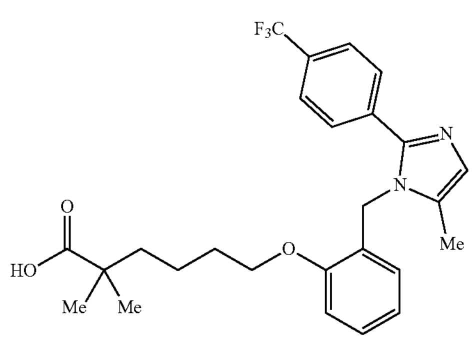 [SMILES: Cc1cnc(-c2ccc(C(F)(F)F)cc2)n1Cc1ccccc1OCCCCC(C)(C)C(=O)O] | 473.51 | 14.30 |

TABLE 1-continued

| Compound | Structure | Mol. Wt | PPAR delta transactivation EC50 (nM) |
|---|---|---|---|
| Compound 2s | 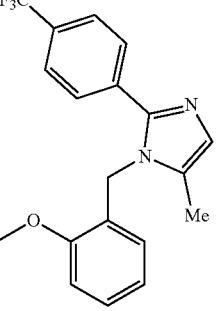 | 460.41 | 18 |
| Compound 2t | 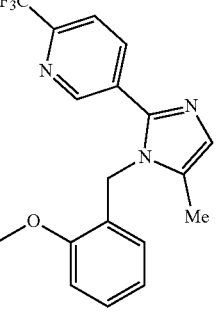 | 461.49 | 227 |
| Comparator Compound 1 | 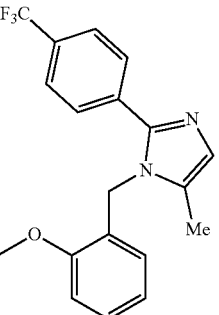 | 446.18 | 0.10 |
| Comparator Compound 2 | 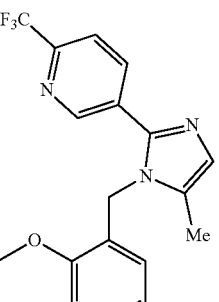 | 447.18 | 3.80 |

Certain compounds of this invention show agonistic activity of PPARδ and selectivity for PPARδ. In addition, certain compounds of this invention show improved clearance compared to comparator compounds. Also, certain compounds of this invention show low hERG inhibition compared to comparator compounds.

Example 1b

Pharmacokinetic (PK) Screening (I.V.)

In this example, the intravenous PK profile of several PPARδ agonists disclosed herein in male CD1 mice was determined. Similar methods can be used to analyze other compounds provided herein. All compounds were administered separately to CD1 mice at 1 mg/kg (i.v.), except the comparator compound to 2c was administered at 3 mg/kg (i.v.), as noted below.

| Ex. No. | Structure | I.V. (1 mg/kg dose) High or Low CL | CL (mL/min/kg) | Comparator Structure | I.V. (1 mg/kg dose) High or Low CL | CL (mL/min/kg) |
|---|---|---|---|---|---|---|
| 2a | [structure] | Low | 33 | [structure] | High | 185 |
| 2b | [structure] | Low | 22 | — | — | — |
| 2c | [structure] | Low | 73 | [structure] | High | 270* |

-continued

| Ex. No. | Structure | I.V. (1 mg/kg dose) High or Low CL | I.V. (1 mg/kg dose) CL (mL/min/kg) | Comparator Structure | I.V. (1 mg/kg dose) High or Low CL | I.V. (1 mg/kg dose) CL (mL/min/kg) |
|---|---|---|---|---|---|---|
| 2d | *(structure with F₃C-phenyl-imidazole, chiral Me, carboxylic acid)* | Low | 25 | *(comparator structure with F₃C-phenyl-imidazole)* | Due to low exposure data could not be measured | |
| 2e | *(structure with F₃CO-phenyl-imidazole, alkene with Me, carboxylic acid)* | Low | 70 | *(comparator structure with F₃CO-phenyl-imidazole)* | High | 185 |
| 2f | *(structure with Me-phenyl-imidazole, chiral Me, carboxylic acid)* | — | — | — | — | — |
| 2g | *(structure with F-phenyl-imidazole, chiral Me, carboxylic acid)* | — | — | — | — | — |

-continued

| Ex. No. | Structure | High or Low CL | CL (mL/min/kg) | Comparator Structure | High or Low CL | CL (mL/min/kg) |
|---|---|---|---|---|---|---|
| 2h | [Structure: 4-fluoro-3-(trifluoromethyl)phenyl imidazole with benzyloxy-dimethyl-hexanoic acid] | Low | 25 | — | — | — |
| 2i | [Structure: 4-chloro-3-fluorophenyl imidazole with benzyloxy-dimethyl-hexanoic acid] | — | — | — | — | — |
| 2j | [Structure: 4-chloro-3-fluorophenyl imidazole with benzyloxy-methyl-hexanoic acid] | Low | 38 | — | — | — |
| 2k | [Structure: 4-(trifluoromethyl)phenyl imidazole with fluoro-benzyloxy-methyl-hexanoic acid] | Low | 17 | — | — | — |

-continued

| Ex. No. | Structure | I.V. (1 mg/kg dose) High or Low CL | I.V. (1 mg/kg dose) CL (mL/min/kg) | Comparator Structure | I.V. (1 mg/kg dose) High or Low CL | I.V. (1 mg/kg dose) CL (mL/min/kg) |
| --- | --- | --- | --- | --- | --- | --- |
| 2l | 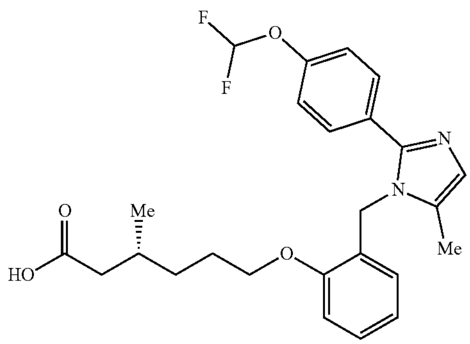 [SMILES: Cc1cnc(-c2ccc(OC(F)F)cc2)n1Cc1ccccc1OCCC[C@@H](C)CC(=O)O] | — | — | — | — | — |
| 2m | 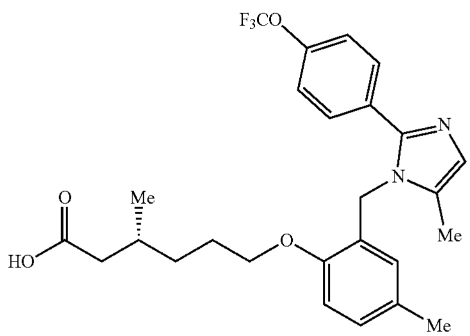 [SMILES: Cc1ccc(OCCC[C@@H](C)CC(=O)O)c(Cn2c(C)cnc2-c2ccc(OC(F)(F)F)cc2)c1] | Low | 85 | — | — | — |
| 2n | 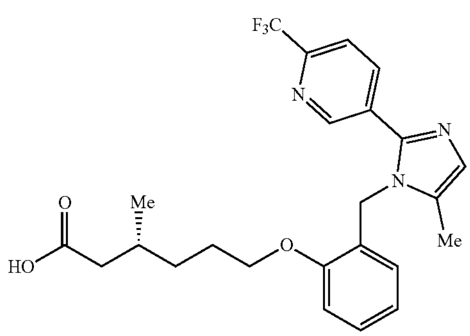 | Low | 62 | | Due to low exposure data could not be measured | |
| 2o | 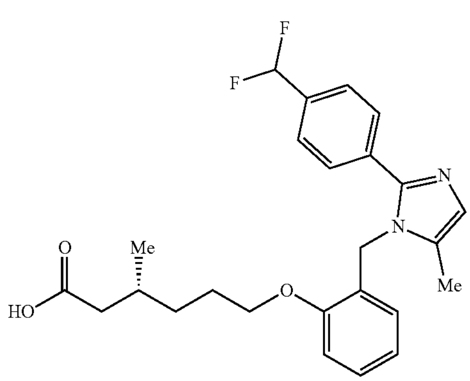 [SMILES: Cc1cnc(-c2ccc(C(F)F)cc2)n1Cc1ccccc1OCCC[C@@H](C)CC(=O)O] | — | — | — | — | — |

| Ex. No. | Structure | I.V. (1 mg/kg dose) High or Low CL | I.V. (1 mg/kg dose) CL (mL/min/kg) | Comparator Structure | I.V. (1 mg/kg dose) High or Low CL | I.V. (1 mg/kg dose) CL (mL/min/kg) |
|---|---|---|---|---|---|---|
| 2p | [structure] | — | — | — | — | — |
| 2q | [structure] | Low | 11 | — | — | — |

*3 mg/kg i.v. dose

High or low clearance (CL) values were assigned based on the reported value for hepatic blood flow in mice (CL=85 mL/min/kg). Plasma CL values were obtained from i.v. pharmacokinetic profiles of the compounds in CD-1 mice after administration of either 1 mg/kg or 3 mg/kg doses. See Boxenbaum H. (1980) Interspecies variation in liver weight, hepatic blood flow and antipyrine intrinsic clearance in extrapolation of Benzodiazepines and phenytoin. *J. Pharmacokinet Biopharm* 8: 165-176, incorporated herein by reference.

The compounds of the invention have desirable clearance profiles, improved exposure and/or improved half-life characteristics over their respective comparator compounds.

Example 2

Synthetic Preparation of Compound Embodiments

Abbreviations

Me methyl
Et ethyl
nPr n-propyl
iPr isopropyl
cPr cyclopropyl
nBu n-butyl
iBu isobutyl
tBu tert-butyl
Boc tert-butyloxycarbonyl
Ac acetyl
Ph phenyl
Tf trifluoromethanesulfonyl
Ts 4-methylphenylsulfonyl
DIAD diisopropyl azodicarboxylate
EDCI 3-(3-dimethylaminopropyl)-1-ethylcarbodiimide
HOBt 1-hydroxybenzotriazole
HATU 1-[bis(dimethylamino)methylene]-1H-1,2,3-triazolo[4,5-b]pyridinium 3-oxide hexafluorophosphate
HBTU N,N,N',N'-Tetramethyl-O-(1H-benzotriazol-1-yl)uronium hexafluorophosphate
NBS N-bromosuccinimide
DIPEA diisopropylethylamine
mCPBA m-chloroperoxybenzoic acid
Togni's reagent 3,3-dimethyl-1-(trifluoromethyl)-1,2-benziodoxole
DCM dichloromethane
DME dimethoxyethane
DMF N,N-dimethylformamide
DMF.DMA N,N-dimethylformamide dimethyl acetal
DMSO dimethylsulfoxide
TFA trifluoroacetic acid
THF tetrahydrofuran
MW microwave irradiation
aq Aqueous
M concentration expressed in mol/L
RT room temperature
TLC thin layer chromatography
HPLC high-performance liquid chromatography MPLC medium pressure liquid chromatography
LCMS liquid chromatography-mass spectrometry
ESI+ Electrospray ionization positive mode
ESI− Electrospray ionization negative mode
¹H NMR (DMSO-d₆) δ (ppm) of peak in ¹H NMR in DMSO-d₆
s singlet (spectrum)
d doublet (spectrum)
t triplet (spectrum)
q quartet (spectrum)
dd double doublet (spectrum)
br broad line (spectrum)
m multiplet (spectrum)

Example-2a

Synthesis of (R)-3-methyl-6-(2-((5-methyl-2-(4-(trifluoromethoxy)phenyl)-1H-imidazol-1-yl)methyl)phenoxy)hexanoic acid (Compound 2a)

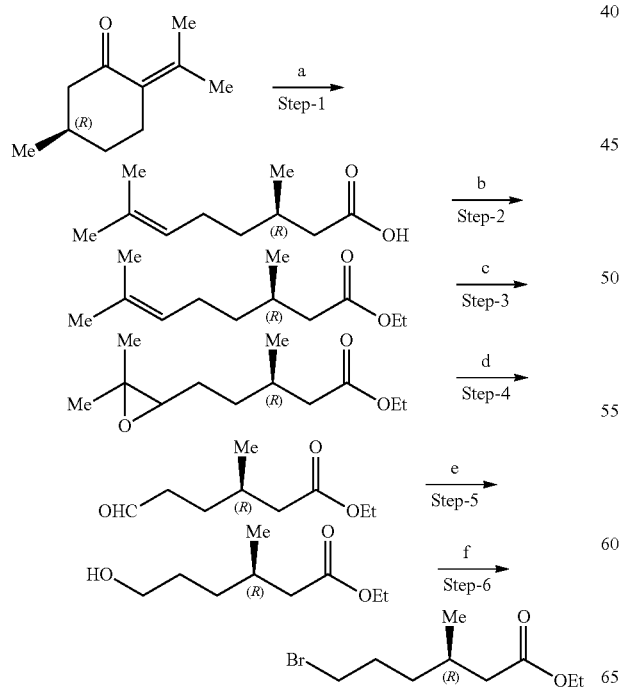

Scheme-2

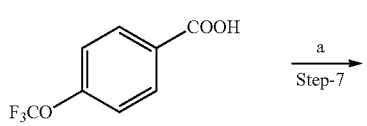

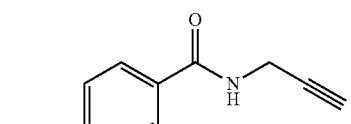

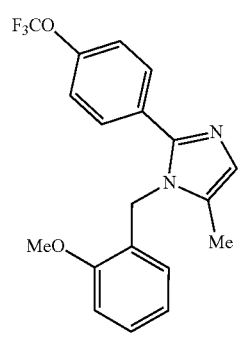

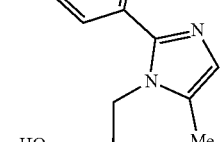

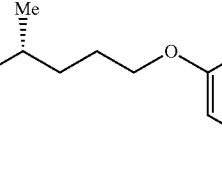

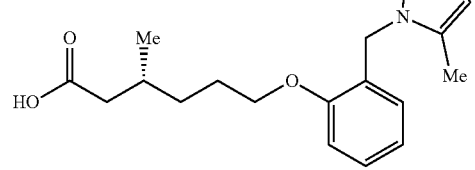

Step-1: Synthesis of (R)-3,7-dimethyloct-6-enoic acid

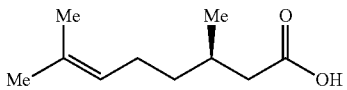 [SMILES: CC(C)=CCC[C@@H](C)CC(=O)O]

In a 5 L three neck round bottom flask, (R)-pulegone (150.0 g, 986.84 mmol) was purged with HCl gas for 3 h at −30° C. The reaction mixture was transferred to re-sealable reaction tube and mixture allowed to stand at RT for 12 h. The mixture was treated with NaOH solution (4N, 3 L) and resulting mixture was stirred at RT for further 12 h. Upon completion of reaction (monitored by TLC), the reaction mixture was diluted with water (1000 mL) and washed with diethyl ether (3×1000 mL). The aqueous layer was acidified (pH 4) with dilute HCl before extracting with diethyl ether (3×1000 mL). The combined organic layer was dried over anhydrous $Na_2SO_4$ and concentrated under reduced pressure to get the title compound (125 g, 74.8%).

$^1$H NMR (300 MHz, DMSO-$d_6$): δ 12.01 (s, 1H), 5.07 (t, J=6.9 Hz, 1H), 2.22 (dd, J=15.0, 6.0 Hz, 1H), 2.03-1.78 (m, 4H), 1.64 (s, 3H), 1.56 (s, 3H), 1.36-1.17 (m, 2H), 0.88 (d, J=6.6 Hz, 3H).

Step-2: Synthesis of ethyl (R)-3,7-dimethyloct-6-enoate

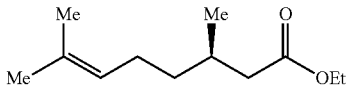 [SMILES: CCOC(=O)C[C@H](C)CCC=C(C)C]

In a 5 L round bottom flask, a suspension of (R)-3,7-dimethyloct-6-enoic acid (100.0 g, 587.41 mmol) and $K_2CO_3$ (243.59 g, 1762.23 mmol) in DMF (1000 mL) was treated with ethyl bromide (95.94 g, 881.12 mmol) at RT. The reaction mixture was stirred at RT for 2 h. Upon completion of reaction (monitored by TLC), the reaction mixture was diluted with water (1000 mL) and extracted with diethyl ether (3×1000 mL). The combined organic extracts were dried over anhydrous $Na_2SO_4$ and concentrated under reduced pressure to get the title compound (101.1 g (86.7%).

$^1$H NMR (300 MHz, CDCl$_3$): δ 5.08 (t, J=6.9 Hz, 1H), 4.12 (q, J=7.2 Hz, 2H), 2.29 (dd, J=14.7, 6.0 Hz, 1H), 2.12-2.05 (m, 1H), 1.99-1.94 (m, 3H), 1.66 (s, 3H), 1.58 (s, 3H), 1.39-1.16 (m, 2H), 1.24 (t, J=6.9 Hz, 3H), 0.93 (d, J=6.6 Hz, 3H).

Step-3: Synthesis of ethyl (3R)-5-(3,3-dimethyloxiran-2-yl)-3-methylpentanoate

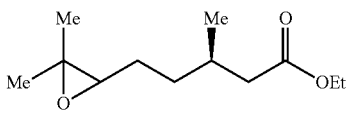 [SMILES: CCOC(=O)C[C@H](C)CCC1OC1(C)C]

In a 5 L round bottom flask, to a solution of ethyl (R)-3,7-dimethyloct-6-enoate (100.0 g, 504.51 mmol) in diethyl ether (1 L) was added a solution of 65% mCPBA (267.51 g, 1.01 mol) in diethyl ether (1 L) dropwise at −30° C. Once the addition was complete, the mixture was warmed to 0° C. and stirred at same temperature for 6 h, before allowing it to stand overnight (~14 h) at 0-3° C. After completion of the reaction (monitored by TLC), the reaction mixture was diluted with diethyl ether (1 L) and washed with 1N NaOH (2×1 L), followed by water (1 L). The organic layer was washed with brine, dried over anhydrous $Na_2SO_4$ and concentrated under reduced pressure to afford the title compound (99.5 g, 92.0%).

$^1$H NMR (300 MHz, CDCl$_3$): δ 4.12 (q, J=7.2 Hz, 2H), 2.69 (t, J=5.4 Hz, 1H), 2.30 (dd, J=8.7, 1.5 Hz 1H), 2.17-2.09 (m, 1H), 2.04-1.97 (m, 1H), 1.55-1.42 (m, 4H), 1.30 (s, 3H), 1.27 (s, 3H), 1.25 (t, J=7.2 Hz, 3H), 0.95 (d, J=6.6 Hz, 3H).

Step-4: Synthesis of ethyl (R)-3-methyl-6-oxohexanoate

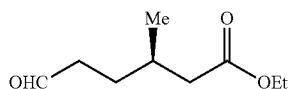 [SMILES: CCOC(=O)C[C@H](C)CCC=O]

In a 5 L round bottom flask, a solution of ethyl (3R)-5-(3,3-dimethyloxiran-2-yl)-3-methylpentanoate (99.0 g, 462.07 mmol) in 1,4-dioxane (1 L) was treated with a solution of NaIO$_4$ (296.49 g, 1.386 mol) in water (1 L) at RT. The reaction mixture was stirred at same temperature for 12 h. Upon completion of reaction (monitored by TLC), the inorganic salts were filtered through Celite® pad and filtrate was extracted with EtOAc (3×1 L). The combined organic extract was washed with water, brine and dried over anhydrous $Na_2SO_4$. The solution was concentrated under reduced pressure to afford the title compound (79.56 g, 99.3%).

$^1$H NMR (300 MHz, CDCl$_3$): δ 9.79 (s, 1H), 4.11 (q, J=7.2 Hz, 2H), 2.48-2.43 (m, 2H), 2.27 (dd, J=15, 6.6 Hz, 1H), 2.17-2.10 (m, 1H), 2.02-1.96 (m, 1H), 1.72-1.66 (m, 1H), 1.54-1.50 (m, 1H), 1.25 (t, J=7.2 Hz, 3H), 0.96 (d, J=6.6 Hz, 3H).

Step 5: Synthesis of ethyl (R)-6-hydroxy-3-methylhexanoate

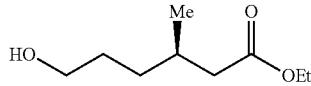 [SMILES: CCOC(=O)C[C@H](C)CCCO]

In a 1 L round bottom flask, a solution of ethyl (R)-3-methyl-6-oxohexanoate (79.0 g, 458.76 mmol) in methanol (400 mL) was treated with NaBH$_4$ (27.75 g, 734.02 mmol) at RT. The reaction mixture was stirred at RT for 2 h. Upon completion of reaction (monitored by TLC), the reaction mixture was diluted with water (500 mL) and extracted with EtOAc (3×500 mL). The combined organic extract was dried over anhydrous $Na_2SO_4$ and concentrated under reduced pressure to get the title compound (70.0 g).

$^1$H NMR (300 MHz, CDCl$_3$): δ 4.12 (q, J=7.2 Hz, 2H), 3.64 (t, J=6.3 Hz, 2H), 2.30 (dd, J=14.7, 6.6 Hz, 1H), 2.17-2.09 (m, 1H), 2.02-1.96 (m, 1H), 1.67-1.56 (m, 5H), 1.26 (t, J=7.2 Hz, 3H), 0.95 (d, J=6.6 Hz, 3H).

Step-6: Synthesis of ethyl (R)-6-bromo-3-methylhexanoate

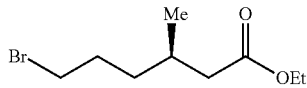 [SMILES: CCOC(=O)C[C@H](C)CCCBr]

In a 1 L round bottom flask, a solution of ethyl (R)-6-hydroxy-3-methylhexanoate (65.0 g, 373.56 mmol) in DCM (650 mL) was treated with PBr$_3$ (101.0 g, 373.56 mmol) at RT. The reaction mixture was stirred at RT for 3 h. Upon completion of reaction (monitored by TLC), the reaction mixture was diluted with water (500 mL) and extracted with diethyl ether (3×500 mL). The organic extract was separated and dried over anhydrous Na$_2$SO$_4$. The solvent was removed under reduced pressure. The desired product was obtained (57.12 g) was used directly in the next step without further purifications.

Step-7: Synthesis of N-(prop-2-yn-1-yl)-4-(trifluoromethoxy)benzamide

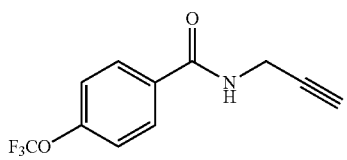

In a 500 mL round bottom flask, a stirred solution of 4-(trifluoromethoxy)benzoic acid (20.0 g, 97.08 mmol) and prop-2-yn-1-amine (6.44 g, 116.49 mmol) in DMF (200 mL) was treated sequentially with EDCI.HCl (22.24 g, 116.49 mmol), HOBt (16.01 g, 116.49 mmol) and Et$_3$N (20.4 mL, 145.62 mmol) at RT under nitrogen atmosphere. The reaction mixture was stirred at RT for 12 h under nitrogen atmosphere. Upon completion of reaction (monitored by TLC), the reaction mixture was diluted with ice cold water and solid precipitated out. The solid was filtered and dried under reduced pressure to yield the title compound (22.0 g, 95.4%).

$^1$H NMR (400 MHz, DMSO-d$_6$): δ 9.08 (brs, 1H), 7.99 (d, J=8.7 Hz, 2H), 7.48 (d, J=8.1 Hz, 2H), 4.05-4.03 (m, 2H), 3.14 (t, J=2.4 Hz, 1H).

LCMS (ESI+, m/z): 244.2 (M+H)$^+$.

Step-8: Synthesis of 1-(2-methoxybenzyl)-5-methyl-2-(4-(trifluoromethoxy)phenyl)-1H-imidazole

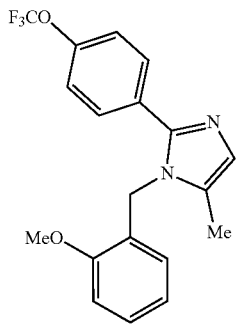 [SMILES: COc1ccccc1Cn1c(C)cnc1-c1ccc(OC(F)(F)F)cc1]

In a 500 mL resealable tube, a solution of N-(prop-2-yn-1-yl)-4-(trifluoromethoxy)benzamide (15.0 g, 61.73 mmol) and 2-methoxybenzyl amine (21.10 g, 154.32 mmol) in toluene (150 mL) was treated with Zn(OTf)$_2$ (2.30 g, 6.17 mmol) at RT under nitrogen atmosphere. The reaction mixture was heated at 120° C. for 12 h. Upon completion of reaction (monitored by TLC), the reaction mixture was diluted with water and extracted with EtOAc (3×100 mL). The organic extract was washed with saturated NaHCO$_3$, brine and dried over anhydrous Na$_2$SO$_4$. The solution was concentrated under reduced pressure and residue obtained was purified by silica gel column chromatography (elution, 25% EtOAc in hexanes) to yield the title compound (15.2 g, 67.8%).

$^1$H NMR (300 MHz, DMSO-d$_6$): δ 7.55 (d, J=8.4 Hz, 2H), 7.39 (d, J=8.4 Hz, 2H), 7.28 (m, 1H), 7.05 (d, J=8.4 Hz, 1H), 6.91-6.86 (m, 2H), 6.37 (d, J=7.5 Hz, 1H), 5.14 (s, 2H), 3.80 (s, 3H), 2.08 (s, 3H).

$^{19}$F NMR (300 MHz, DMSO-d$_6$): δ −52.03.

LCMS (ESI+, m/z): 363.6 (M+H)$^+$.

Step-9: Synthesis of 2-((5-methyl-2-(4-(trifluoromethoxy)phenyl)-1H-imidazol-1-yl)methyl)phenol

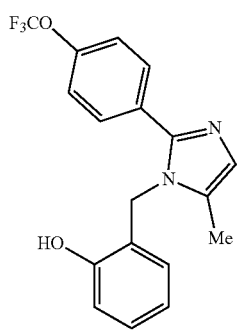 [SMILES: Cc1cnc(-c2ccc(OC(F)(F)F)cc2)n1Cc1ccccc1O]

In a 500 mL round bottom flask, a solution of 1-(2-methoxybenzyl)-5-methyl-2-(4-(trifluoromethoxy)phenyl)-1H-imidazole (30.0 g, 82.64 mmol) in dichloromethane (300 mL) was treated with BBr$_3$ (30.0 mL, 82.64 mmol) drop wise at 0° C. The reaction mixture was stirred at RT for 2 h. Upon completion of reaction (monitored by TLC), the reaction mixture was basified (pH~9) with aqueous NaHCO$_3$ and extracted with EtOAc. The organic extract was dried over anhydrous Na$_2$SO$_4$ and concentrated under reduced pressure to afford the title compound (27.1 g, 94.4%).

$^1$H NMR (300 MHz, DMSO-d$_6$): δ 9.93 (s, 1H), 7.55 (d, J=9.0 Hz, 2H), 7.39 (d, J=8.1 Hz, 2H), 7.11-7.06 (m, 1H), 6.91-6.82 (m, 2H), 6.70 (t, J=6.9 Hz, 1H), 6.27 (d, J=7.8 Hz, 1H), 5.09 (s, 2H), 2.06 (s, 3H).

$^{19}$F NMR (300 MHz, DMSO-d$_6$): δ −56.76.

LCMS (ESI+, m/z): 349.3 (M+H)$^+$.

Step-10: Synthesis of ethyl (R)-3-methyl-6-(2-((5-methyl-2-(4-(trifluoromethoxy)phenyl)-1H-imidazol-1-yl)methyl)phenoxy)hexanoate

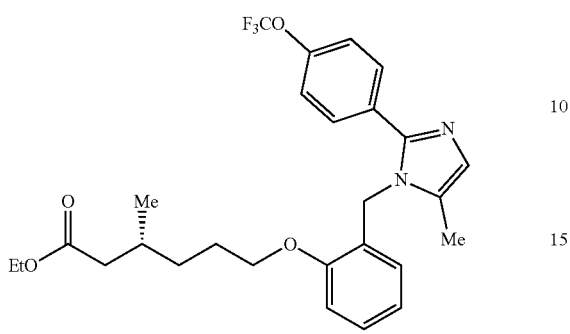

In a 250 mL round bottom flask, a stirred solution of 2-((5-methyl-2-(4-(trifluoromethoxy)phenyl)-1H-imidazol-1-yl)methyl)phenol (10.0 g, 28.71 mmol) in DMF (100 mL) was treated with KO$^t$Bu (9.66 g, 86.13 mmol) and ethyl (R)-6-bromo-3-methylhexanoate (20.33 g, 86.13 mmol) at RT under nitrogen atmosphere. The resulting reaction mixture was stirred at RT for 2 h. Upon completion of the reaction (monitored by TLC), the reaction mixture quenched with ice cold water and extracted with ethyl acetate. The organic layer was washed with brine, dried over anhydrous Na$_2$SO$_4$. and concentrated under reduced pressure. The residue obtained was purified by silica gel column chromatography (gradient elution, 15-30% EtOAc in hexanes) to afford the title compound (7.5 g, 52.1%).

LCMS (ESI$_+$, m/z): 505.4 (M+H)$^+$.

Step-11: Synthesis of (R)-3-methyl-6-(2-((5-methyl-2-(4-(trifluoromethoxy)phenyl)-1H-imidazol-1-yl)methyl)phenoxy)hexanoic acid (Compound 2a)

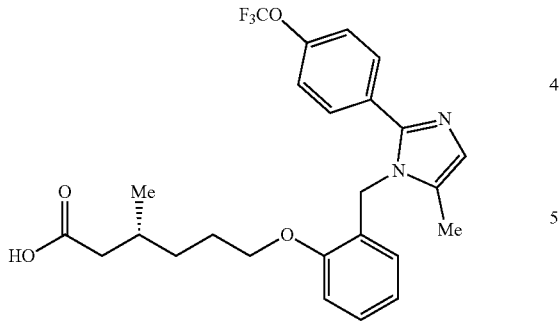

In a 250 mL round bottom flask, a stirred solution of ethyl (R)-3-methyl-6-(2-((5-methyl-2-(4-(trifluoromethoxy)phenyl)-1H-imidazol-1-yl)methyl)phenoxy)hexanoate (7.5 g, 14.86 mmol) in THF (75 mL), ethanol (32 mL) and water (32 mL) was treated with lithium hydroxide monohydrate (3.12 g, 74.33 mmol) at RT. The reaction mixture was stirred at RT for 12 h. Upon completion of reaction (monitored by TLC), the reaction mixture was concentrated under reduced pressure. The residue obtained was washed with EtOAc, diluted with cold water and acidified (pH~5) with 1N HCl. The solid was filtered and dried under reduced pressure to give the title compound (5.3 g, 75.7%).

$^1$H NMR (400 MHz, DMSO-d$_6$, 80° C.): δ 11.70 (brs, 1H), 7.57 (d, J=8.4 Hz, 2H), 7.32 (d, J=8.4 Hz, 2H), 7.24 (t, J=7.2 Hz, 1H), 7.01 (d, J=8.4 Hz, 1H), 6.89 (s, 1H), 6.85 (t, J=7.2 Hz, 1H), 6.40 (d, J=7.2 Hz, 1H), 5.16 (s, 2H), 4.02 (t, J=6.4 Hz, 2H), 2.20 (dd, J=14.8, 6.0 Hz, 1H), 2.11 (s, 3H), 2.06-2.00 (m, 1H), 1.90-1.88 (m, 1H), 1.75-1.71 (m, 2H), 1.48-1.45 (m, 1H), 1.33-1.29 (m, 1H), 0.91 (d, J=6.8 Hz, 3H).

$^{19}$F NMR (400 MHz, DMSO-d$_6$): δ −56.80

LCMS (ESI+, m/z): 477.8 (M+H)$^+$.

HPLC: 98.19% (210 nm).

Example-2b

Synthesis of (R)-6-(2-((2-(4-chlorophenyl)-5-methyl-1H-imidazol-1-yl)methyl)phenoxy)-3-methylhexanoic acid (Compound 2b)

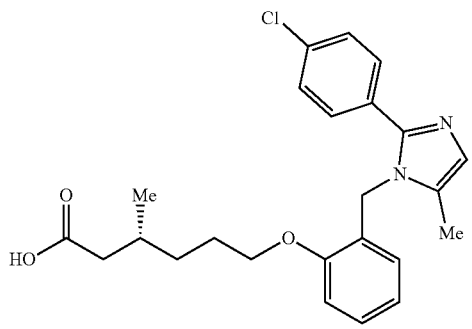

Scheme

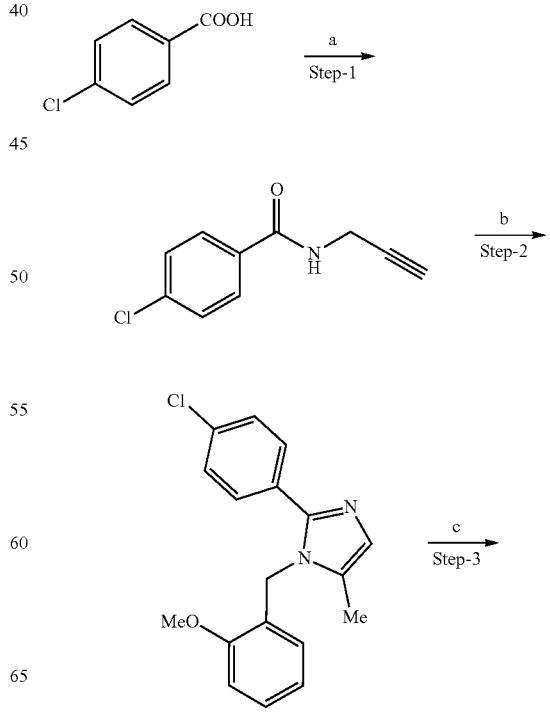

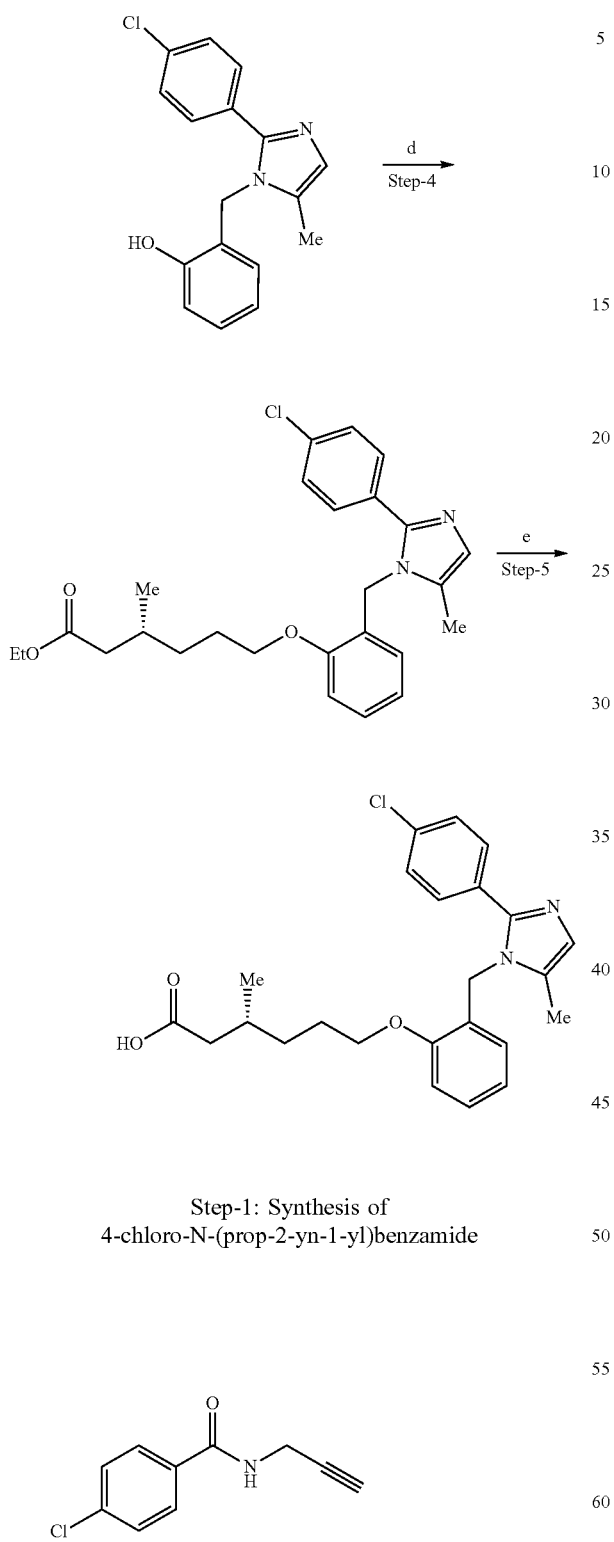

Step-1: Synthesis of 4-chloro-N-(prop-2-yn-1-yl)benzamide

The title compound was synthesized from 4-chlorobenzoic acid (5.0 g, 31.94 mmol) and prop-2-yn-1-amine (1.75 g, 31.94 mmol) following the experimental procedure described in step-7 of Example-2a.

Yield: 4.52 g (73.0%).

$^1$H NMR (400 MHz, DMSO-d$_6$): δ 9.21 (brs, 1H), 7.85 (d, J=8.8 Hz, 2H), 7.53 (d, J=8.8 Hz, 2H), 4.04-4.02 (m, 2H), 3.12 (t, J=2.8 Hz, 1H).

LCMS (ESI+, m/z): 194.0, 196.0 (M+H)$^+$.

Step-2: Synthesis of 2-(4-chlorophenyl)-1-(2-methoxybenzyl)-5-methyl-1H-imidazole

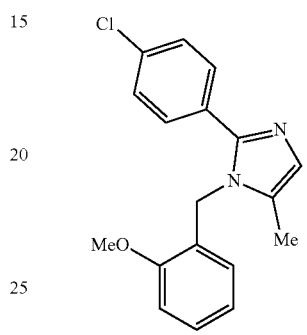

The title compound was synthesized from 4-chloro-N-(prop-2-yn-1-yl)benzamide (1.0 g, 5.16 mmol) and 2-methoxybenzyl amine (1.06 g, 7.74 mmol) following the experimental procedure described in step-8 of Example-2a.

Yield: 0.81 g (51.1%).

$^1$H NMR (400 MHz, CDCl$_3$): δ 7.41 (d, J=8.8 Hz, 2H), 7.30-725 (m, 3H), 6.98 (s, 1H), 6.93-6.88 (m, 2H), 6.58 (d, J=7.2 Hz, 1H), 5.09 (s, 2H), 3.86 (s, 3H), 2.11 (s, 3H),

LCMS (ESI+, m/z): 313.1, 315.1 (M+H)$^+$.

Step-3: Synthesis of 2-((2-(4-chlorophenyl)-5-methyl-1H-imidazol-1-yl)methyl)phenol

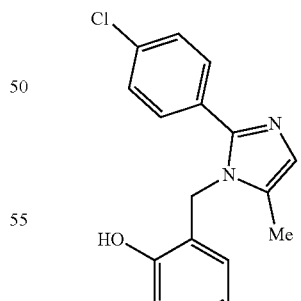

The title compound was synthesized from 2-(4-chlorophenyl)-1-(2-methoxybenzyl)-5-methyl-1H-imidazole (0.8 g, 2.56 mmol) following the experimental procedure described in step-9 of Example-2a.

Yield: 0.62 g (81.15%).

LCMS (ESI+, m/z): 299.3, 301.3 (M+H)$^+$.

Step-4: Synthesis of ethyl (R)-6-(2-((2-(4-chlorophenyl)-5-methyl-1H-imidazol-1-yl)methyl)phenoxy)-3-methylhexanoate

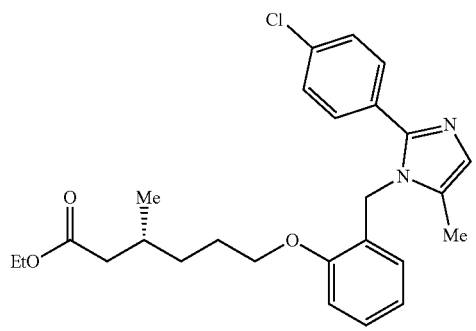

The title compound was synthesized from 2-((2-(4-chlorophenyl)-5-methyl-1H-imidazol-1-yl)methyl)phenol (0.6 g, 2.01 mmol) and ethyl (R)-6-bromo-3-methylhexanoate (0.186 g, 1.48 mmol) following the experimental procedure described in step-10 of Example-2a.
Yield: 0.321 g (35.1%).
LCMS (ESI+, m/z): 454.5, 456.5 (M+H)$^+$.

Step-5: Synthesis (R)-6-(2-((2-(4-chlorophenyl)-5-methyl-1H-imidazol-1-yl)methyl) phenoxy)-3-methylhexanoic acid (Compound 2b)

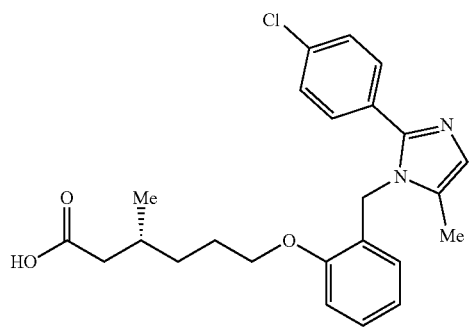

The title compound was synthesized from ethyl (R)-6-(2-((2-(4-chlorophenyl)-5-methyl-1H-imidazol-1-yl)methyl) phenoxy)-3-methylhexanoate (0.3 g, 0.66 mmol) following the experimental procedure described in step-11 of Example-2a and purified by preparative silica gel thin layer chromatography (elution, 4% MeOH—CH$_2$Cl$_2$).
Yield: 0.05 g (18%).
$^1$H NMR (400 MHz, DMSO-d$_6$, 80° C.): δ 7.48 (d, J=8.4 Hz, 2H), 7.40 (d, J=8.4 Hz, 2H), 7.24 (t, J=7.6 Hz, 1H), 7.00 (d, J=8.4 Hz, 1H), 6.88 (s, 1H), 6.84 (t, J=7.6 Hz, 1H), 6.51 (d, J=7.2 Hz, 1H), 5.14 (s, 2H), 3.99 (t, J=5.6 Hz, 2H), 2.19-2.16 (m, 1H), 2.09 (s, 3H), 2.06-2.00 (m, 1H), 1.93-1.86 (m, 1H), 1.72-1.67 (m, 2H), 1.45-1.42 (m, 1H), 1.32-1.26 (m, 1H), 0.91 (d, J=6.4 Hz, 3H).

LCMS (ESI+, m/z): 427.2, 429.2 (M+H)$^+$.
HPLC: 95.84% (210 nm).

Example-2c

Synthesis of (R)-6-(2-((2-(4-(furan-2-yl)phenyl)-5-methyl-1H-imidazol-1-yl)methyl) phenoxy)-3-methylhexanoic acid (Compound 2c)

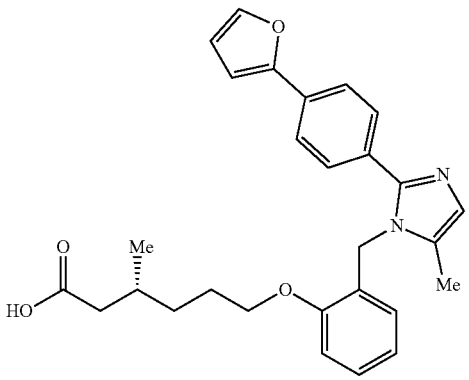 [SMILES: Cc1cnc(-c2ccc(-c3ccco3)cc2)n1Cc1ccccc1OCCC[C@@H](C)CC(=O)O]

Scheme

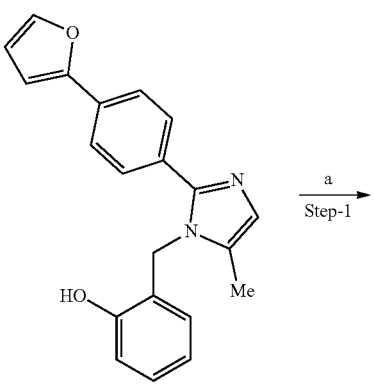

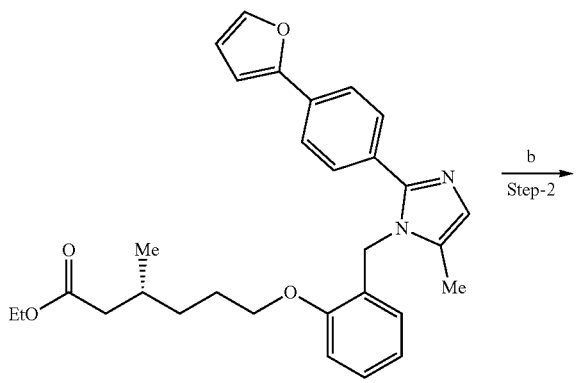

53

-continued

Step-1: Synthesis of ethyl (R)-6-(2-((2-(4-(furan-2-yl)phenyl)-5-methyl-1H-imidazol-1-yl)methyl)phenoxy)-3-methylhexanoate

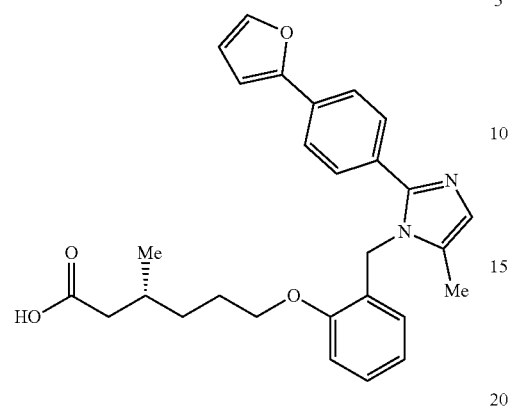

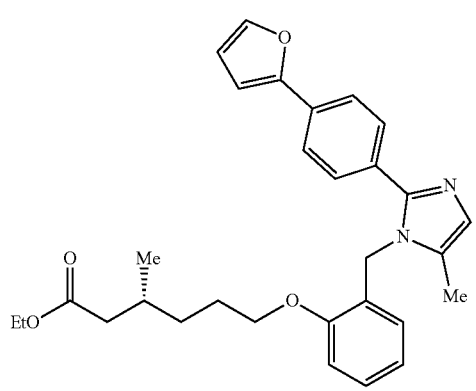

In a 50 mL round bottom flask, a stirred solution of 2-((2-(4-(furan-2-yl)phenyl)-5-methyl-1H-imidazol-1-yl)methyl)phenol (0.2 g, 0.60 mmol) (a procedure for the preparation of which is disclosed in U.S. Application No. 62/061,483, incorporated herein by reference) in DMF (5 mL) was treated with $K_2CO_3$ (0.25 g, 1.81 mmol) and ethyl (R)-6-bromo-3-methylhexanoate (0.42 g, 1.81 mmol) at RT under nitrogen atmosphere. The resulting reaction mixture was heated 60° C. for 12 h. Upon completion of the reaction (monitored by TLC), the reaction mixture was quenched with ice cold water and extracted with ethyl acetate (25 mL×3). The combined organic extract was washed with brine, dried over anhydrous $Na_2SO_4$. and concentrated under reduced pressure. The residue obtained was purified by silica gel column chromatography (gradient elution, 15-30% EtOAc in hexanes) to afford the title compound (0.181 g, 61.2%).

LCMS (ESI+, m/z): 487.3 (M+H)$^+$.

54

Step-2: Synthesis of (R)-6-(2-((2-(4-(furan-2-yl)phenyl)-5-methyl-1H-imidazol-1-yl) methyl)phenoxy)-3-methylhexanoic acid (Compound 2c)

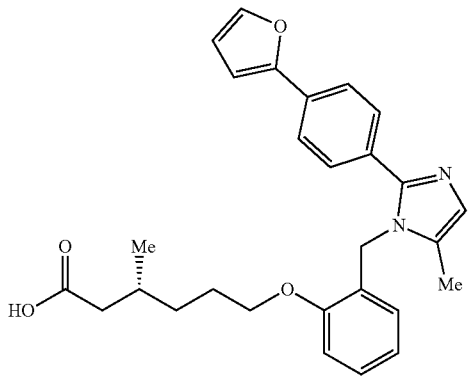

The title compound was synthesized from ethyl (R)-6-(2-((2-(4-(furan-2-yl)phenyl)-5-methyl-1H-imidazol-1-yl) methyl)phenoxy)-3-methylhexanoate (0.180 g, 0.37 mmol) following the experimental procedure described in step-11 of Example-2a and purified by preparative HPLC [Luna (250 mm×21.20 mm, 5μ); flow: 18.0 ml/min; mobile phase: A/B=0.1% TFA in water/MeCN; T/% B=0/20, 2/20/8/70]. Yield: 0.04 g (23.6%).

$^1$H NMR (400 MHz, DMSO-d$_6$, 80° C.): δ 7.68 (d, J=8.8 Hz, 2H), 7.65 (s, 1H), 7.50 (d, J=8.8 Hz, 2H), 7.24 (t, J=8.0 Hz 1H), 7.02 (d, J=8.0 Hz, 1H), 6.90-6.84 (m, 3H), 6.57-6.56 (m, 1H), 6.48 (d, J=8.4 Hz, 1H), 5.18 (s, 2H), 4.02 (d, J=6.0 Hz, 2H), 2.19-2.15 (m, 1H), 2.10 (s, 3H), 2.04-1.98 (m, 1H), 1.91-1.86 (m, 1H), 1.72-1.70 (m, 2H), 1.47-1.42 (m, 1H), 1.31-1.29 (m, 1H), 0.89 (d, J=6.8 Hz, 3H).

LCMS (ESI+, m/z): 459.2 (M+H)$^+$.

HPLC: 97.50% (210 nm).

Example-2d

Synthesis of (R)-3-methyl-6-(2-((5-methyl-2-(4-(trifluoromethyl)phenyl)-1H-imidazol-1-yl)methyl) phenoxy)hexanoic acid (Compound 2d)

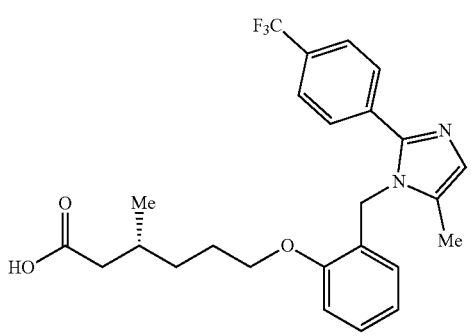

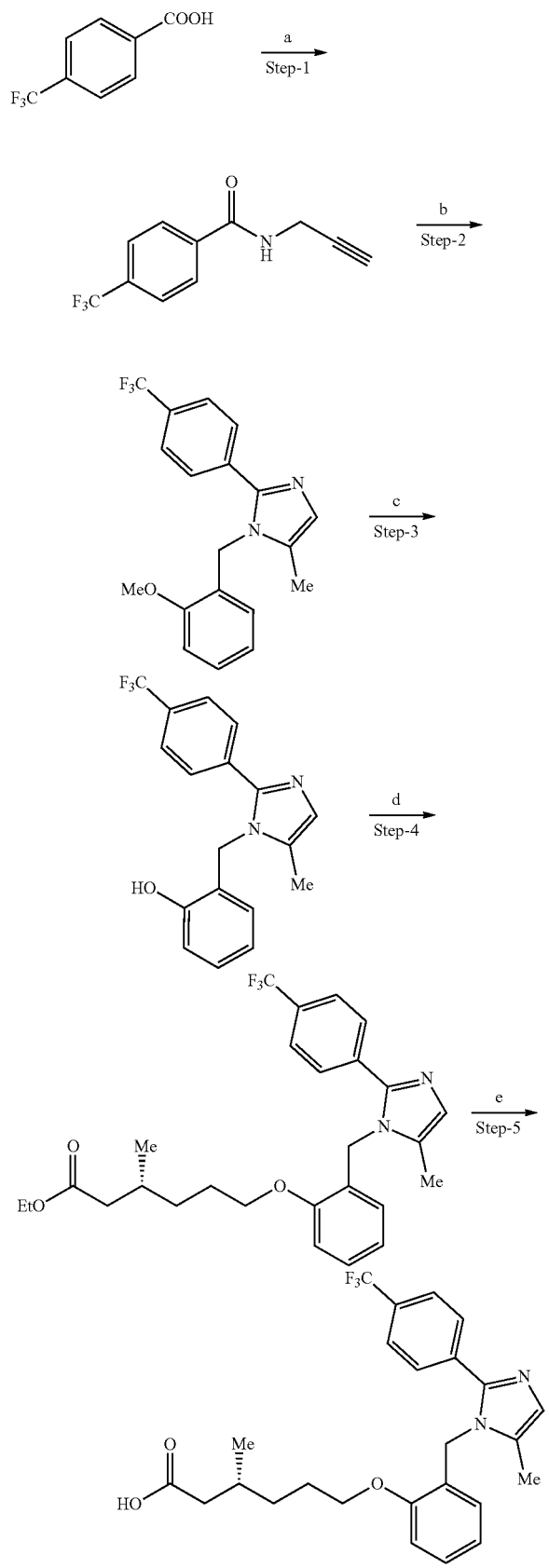

Step-1: Synthesis of N-(prop-2-yn-1-yl)-4-(trifluoromethyl)benzamide

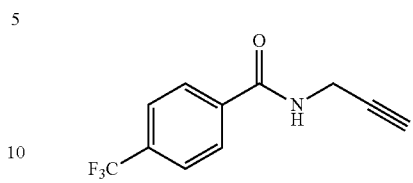

In a 500 mL round bottom flask, a stirred solution of 4-(trifluoromethyl)benzoic acid (10 g, 52.63 mmol) and prop-2-yn-1-amine (3.47 g, 63.15 mmol) in DMF (200 mL) was treated sequentially with EDCI.HCl (20.09 g, 105.2 mmol), HOBt (14.2 g, 105.2 mmol) and Et$_3$N (14.6 mL, 105.2 mmol) at RT under nitrogen atmosphere. The reaction mixture was stirred at RT for 12 h under nitrogen atmosphere. Upon completion of reaction (monitored by TLC), the reaction mixture was diluted with ice cold water and solid precipitated out. The solid was filtered and dried under reduced pressure to yield the title compound (8.42 g, 70.5%).

$^1$H NMR (300 MHz, CDCl$_3$): δ 7.90 (d, J=8.1 Hz, 2H), 7.71 (d, J=8.8 Hz, 2H), 6.47 (brs, 1H), 4.28-4.62 (m, 2H), 3.12 (t, J=2.4 Hz, 1H).

LCMS (ESI+, m/z): 228.2 (M+H)$^+$.

Step-2: Synthesis of 1-(2-methoxybenzyl)-5-methyl-2-(4-(trifluoromethyl)phenyl)-1H-imidazole

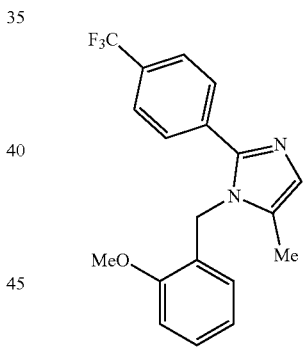

In a 500 mL resealable reaction tube, a solution of N-(prop-2-yn-1-yl)-4-(trifluoromethyl)benzamide (13.3 g, 58.59 mmol) and 2-methoxybenzyl amine (12.0 g, 87.84 mmol) in toluene (150 mL) was treated with Zn(OTf)$_2$ (6.67 g, 17.5 mmol) at RT under nitrogen atmosphere. The reaction mixture was heated at 110° C. for 12 h. Upon completion of reaction (monitored by TLC), the reaction mixture was diluted with water and extracted with EtOAc (3×100 mL). The combined organic extract was washed with saturated NaHCO$_3$, brine and dried over anhydrous Na$_2$SO$_4$. The solution was concentrated under reduced pressure and the residue obtained was purified by silica gel column chromatography (elution, 25% EtOAc in hexanes) to afford the title compound (17.3 g, 85.3%).

$^1$H NMR (400 MHz, CDCl$_3$): δ 7.59-7.54 (m, 4H), 7.30-7.23 (m, 1H), 7.00 (s, 1H), 6.91-6.86 (m, 2H), 6.57 (d, J=7.2 Hz, 1H), 5.11 (s, 2H), 3.84 (s, 3H), 2.11 (s, 3H).

LCMS (ESI+, m/z): 347.3 (M+H)$^+$.

Step-3: Synthesis of 2-((5-methyl-2-(4-(trifluoromethyl)phenyl)-1H-imidazol-1-yl)methyl)phenol

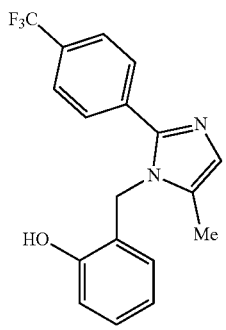 [SMILES: Cc1cnc(-c2ccc(C(F)(F)F)cc2)n1Cc1ccccc1O]

In a 500 mL round bottom flask, a solution of 1-(2-methoxybenzyl)-5-methyl-2-(4-(trifluoromethyl)phenyl)-1H-imidazole (17.3 g, 49.94 mmol) in DCM (150 mL) was treated with BBr$_3$ (1.0 M, 90.0 mL) drop wise at 0° C. The reaction mixture was stirred at RT for 4 h. Upon completion of reaction (monitored by TLC), the reaction mixture was basified (pH~9) with aqueous NaHCO$_3$ and extracted with EtOAc (3×500 mL). The combined organic extract was dried over anhydrous Na$_2$SO$_4$ and concentrated under reduced pressure to afford the title compound (19.2 g, crude).

$^1$H NMR (400 MHz, DMSO-d$_6$): δ 9.99 (s, 1H), 7.88 (d, J=8.4 Hz, 2H), 7.77 (d, J=8.4 Hz, 2H), 7.33 (s, 1H), 7.14-7.10 (m, 1H), 6.83 (d, J=8.0 Hz, 1H), 6.74-6.70 (m, 1H), 6.55 (d, J=6.8 Hz, 1H), 5.21 (s, 2H), 2.16 (s, 3H).

LCMS (ESI+, m/z): 333.3 (M+H)$^+$.

Step-4: Synthesis of ethyl (R)-3-methyl-6-(2-((5-methyl-2-(4-(trifluoromethyl)phenyl)-1H-imidazol-1-yl)methyl)phenoxy)hexanoate

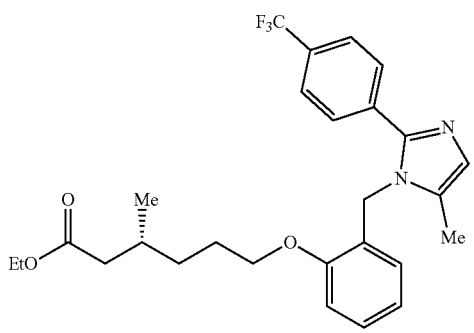

In a 250 mL round bottom flask, a stirred solution of 2-((5-methyl-2-(4-(trifluoromethyl) phenyl)-1H-imidazol-1-yl)methyl)phenol (4.0 g, 12.0 mmol) in DMF (100 mL) was treated with KO$^t$Bu (4.03 g, 36.1 mmol) and ethyl (R)-6-bromo-3-methylhexanoate (8.52 g, 36.10 mmol) at RT under nitrogen atmosphere. The resulting reaction mixture was stirred at RT for 12 h. Upon completion of the reaction (monitored by TLC), the reaction mixture quenched with ice cold water and extracted with EtOAc (3×100 mL). The combined organic extract was washed with brine, dried over anhydrous Na$_2$SO$_4$. and concentrated under reduced pressure. The residue obtained was purified by silica gel column chromatography (gradient elution, 15-30% EtOAc in hexanes) to afford the title compound (3.31 g, 56.3%).

LCMS (ESI+, m/z): 489.3 (M+H)$^+$.

Step-5: Synthesis of (R)-3-methyl-6-(2-((5-methyl-2-(4-(trifluoromethyl)phenyl)-1H-imidazol-1-yl) methyl)phenoxy)hexanoic acid (Compound 2d)

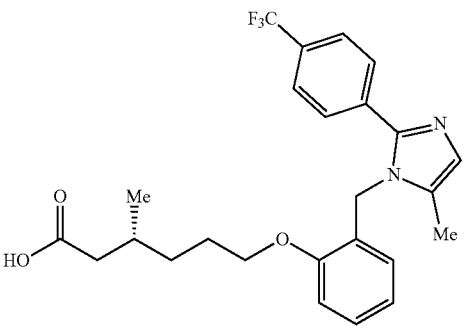

In a 250 mL round bottom flask, a stirred solution of ethyl (R)-3-methyl-6-(2-((5-methyl-2-(4-(trifluoromethyl)phenyl)-1H-imidazol-1-yl)methyl)phenoxy)hexanoate (3.3 g, 6.75 mmol) in THF (30 mL), ethanol (10 mL) and water (10 mL) was treated with lithium hydroxide monohydrate (1.42 g, 33.8 mmol) at RT. The reaction mixture was stirred at RT for 12 h. Upon completion of reaction (monitored by TLC), the reaction mixture was concentrated under reduced pressure. The residue obtained was washed with EtOAc, diluted with cold water and acidified (pH~5) with 1N HCl. The solid obtained was filtered and dried under reduced pressure to give the title compound (1.12 g, 36.0%).

$^1$H NMR (400 MHz, DMSO-d$_6$): δ 12.00 (brs, 1H), 7.71 (d, J=8.4 Hz, 2H), 7.62 (d, J=8.4 Hz, 2H), 7.26-7.21 (m, 1H), 7.01 (d, J=8.4 Hz, 1H), 6.93 (s, 1H), 6.86-6.83 (m, 1H), 6.38 (d, J=6.8 Hz, 1H), 5.16 (s, 2H), 3.98 (t, J=6.0 Hz, 2H), 2.19-2.14 (m, 1H), 2.08 (s, 3H), 1.99-1.93 (m, 1H), 1.84-1.76 (m, 1H), 1.67-1.65 (m, 2H), 1.45-1.42 (m, 1H), 1.28-1.18 (m, 1H), 0.83 (d, J=6.4 Hz, 3H) $^{19}$F NMR (400 MHz, DMSO-d$_6$): δ −56.4

LCMS (ESI+, m/z): 460.8 (M+H)$^+$.

HPLC: 98.89% (210 nm).

Preparation of Polymorphs and Salts of Compound 2d

Various forms of compound 2d can be formed from different crystallization experiments, as detailed below.

Compound 2d Form B

New Form B of Compound 2d was obtained by slurrying Compound 2d in ethyl acetate at 50° C., 2-propanol at 50° C., acetone at 25° C., water at 25° C., water/methanol at 25° C., or ethanol at 25° C.

Compound 2d Form C

New Form C of Compound 2d was obtained by slurrying Compound 2d in acetonitrile at 50° C., water/acetonitrile at 4° C., and 2-methyltetrahydrofuran at 4° C.

Compound 2d Form D

New Form D of Compound 2d was obtained by slurrying Compound 2d in cyclopentyl methyl ether at 50° C., toluene at 25° C., and from evaporative crystallization from dichloromethane.

Compound 2d Form E

New Form E Compound 2d was obtained by slurrying Compound 2d in methanol at 25° C.

Preparation of Hemisulfate Salt Form 1 of Compound 2d

In a 50 mL vial was dissolved 883.2 mg of Compound 2d was dissolved in 35 mL methanol. Then, $H_2SO_4$ (1920 μL, 1M in $H_2O$, 1 equivalent) was pipetted in. The solvent was allowed to evaporate under $N_2$. Once evaporated, 2-propanol (18 mL) was pipetted in followed by a stir bar. The vial was capped and placed on a 50° C. stir plate for 1 hour, then the temperature was dropped to 25° C., where it stirred for 1 day. After 1 day, the solids were filtered under vacuum and allowed to air dry.

$^1$H NMR (400 MHz, DMSO-$d_6$): δ 7.85 (d, J=8.4 Hz, 2H), 7.74 (d, J=8.4 Hz, 2H), 7.36 (s, 1H), 7.27 (t, J=8.4 Hz, 1H), 7.02 (d, J=8.4 Hz, 1H), 6.85 (t, J=7.6 Hz, 1H), 6.62 (d, J=7.2 Hz, 1H), 5.26 (s, 2H), 3.96 (t, J=6.0 Hz, 2H), 2.21-2.16 (m, 4H), 1.96 (dd, J=8.0, 15.2 Hz, 1H), 1.83-1.80 (m, 1H), 1.67-1.59 (m, 2H), 1.35-1.31 (m, 1H), 1.28-1.18 (m, 1H), 0.85 (d, J=6.4 Hz, 3H).

Mass Spectrum (ESI) m/e 461.2.

Elemental Analysis: Calculated: C, 58.93%; H, 5.54%; N, 5.50%; S, 3.15. Observed: C, 58.30%; H, 5.36%; N, 5.42%; S, 3.47.

The hemisulfate salt form 1 of Compound 2d was also obtained according to the same manner as that mentioned above using acetonitrile (18 mL) as a solvent instead of 2-propanol (18 mL).

Preparation of Hemisulfate Salt Form 2 of Compound 2d

Approximately 90 to 110 mg of hemisulfate form 1 of Compound 2d was weighed out and transferred to a 4 mL amber glass vial followed by 0.8 mL of methanol and a magnetic stir bar. The vial was sealed and placed onto a temperature controlled stir plate set to 25° C. and stirred for 15 days at 500 rpm. The solid isolate from this experiment, identified as hemisulfate form 2 of Compound 2d, was obtained and characterized, in particular, by XRPD.

Example-2e

Synthesis of (E)-4-methyl-6-(2-((5-methyl-2-(4-(trifluoromethoxy)phenyl)-1H-imidazol-1-yl)methyl)phenoxy)hex-4-enoic acid (Compound 2e)

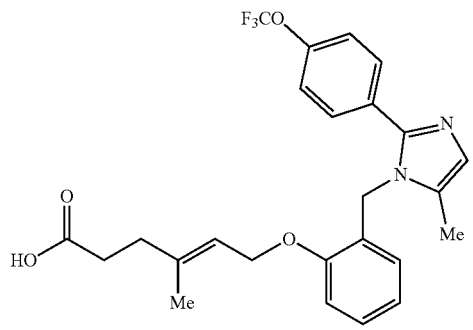 [SMILES: C/C(=C\COc1ccccc1Cn1c(C)cnc1-c1ccc(OC(F)(F)F)cc1)CCC(=O)O]

Scheme

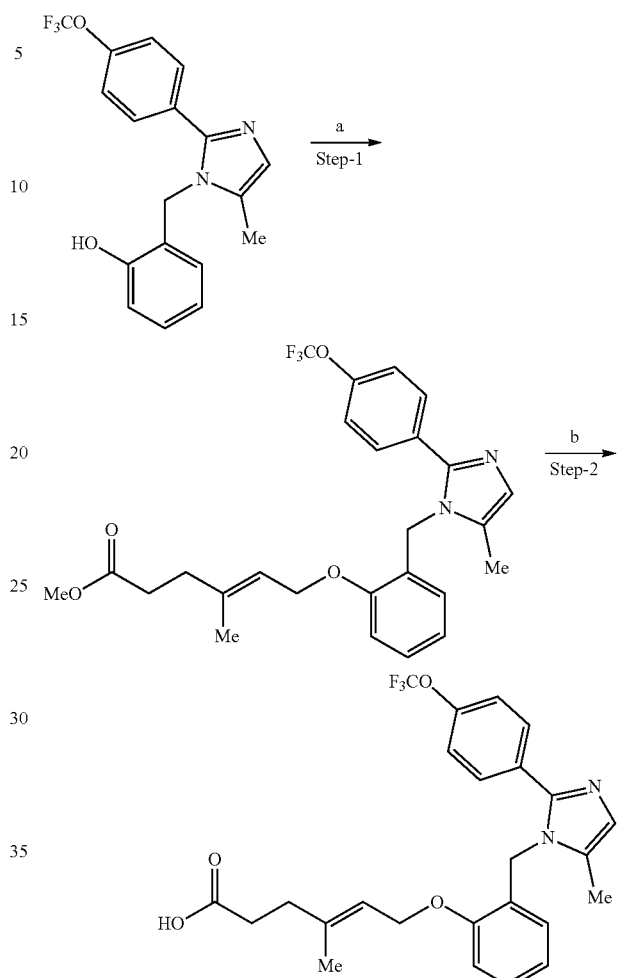

Step-1: Synthesis of methyl (E)-4-methyl-6-(2-((5-methyl-2-(4-(trifluoromethoxy)phenyl)-1H-imidazol-1-yl)methyl)phenoxy)hex-4-enoate

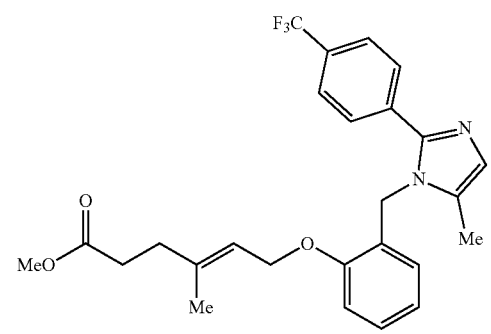 [SMILES: COC(=O)CC/C(C)=C/COc1ccccc1Cn1c(C)cnc1-c1ccc(C(F)(F)F)cc1]

The title compound was synthesized from 2-((5-methyl-2-(4-(trifluoromethoxy)phenyl)-1H-imidazol-1-yl)methyl)phenol (0.3 g, 0.86 mmol) and methyl (E)-6-bromo-4-methylhex-4-enoate (0.57 g, 2.58 mmol) (a procedure for the preparation of which is disclosed in U.S. Application No. 62/061,483, incorporated herein by reference) following the experimental procedure described in step-1 of Example-2c.

Yield: 0.180 g.

LCMS (ESI+, m/z): 489.4 (M+H)+.

Step-2: Synthesis of (E)-4-methyl-6-(2-((5-methyl-2-(4-(trifluoromethoxy)phenyl)-1H-imidazol-1-yl)methyl)phenoxy)hex-4-enoic acid (Compound 2e)

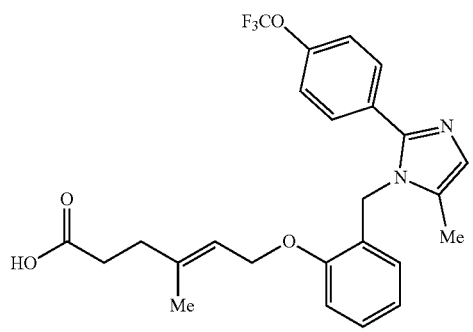 [SMILES: C/C(=C\COc1ccccc1Cn1c(C)cnc1-c1ccc(OC(F)(F)F)cc1)CCC(=O)O]

The title compound was synthesized from methyl (E)-4-methyl-6-(2-((5-methyl-2-(4-(trifluoromethoxy)phenyl)-1H-imidazol-1-yl)methyl)phenoxy)hex-4-enoate (0.18 g, 0.36 mmol) following the experimental procedure described in step-11 of Example-2a.

$^1$H NMR (400 MHz, DMSO-$d_6$): δ 7.69 (d, J=8.8 Hz, 2H), 7.49 (d, J=8.4 Hz, 2H), 7.44 (s, 1H), 7.26 (t, J=7.6 Hz, 1H), 7.01 (d, J=8.0 Hz, 1H), 6.83 (t, J=7.2 Hz, 1H), 6.72 (d, J=6.8 Hz, 1H), 5.33-5.28 (m, 3H), 4.52 (d, J=6.4 Hz, 2H), 2.34-2.27 (m, 4H), 2.22 (s, 3H), 1.66 (s, 3H).

$^{19}$F NMR (400 MHz, DMSO-$d_6$): δ −56.77

LCMS (ESI+, m/z): 475.3 (M+H)+.

HPLC: 95.75% (210 nm).

Example-2f

Synthesis of (R)-3-methyl-6-(2-((5-methyl-2-(p-tolyl)-1H-imidazol-1-yl)methyl)phenoxy) hexanoic acid (Compound 2f)

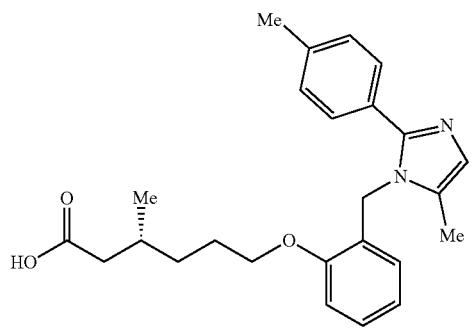 [SMILES: Cc1ccc(-c2ncc(C)n2Cc2ccccc2OCCC[C@@H](C)CC(=O)O)cc1]

Scheme

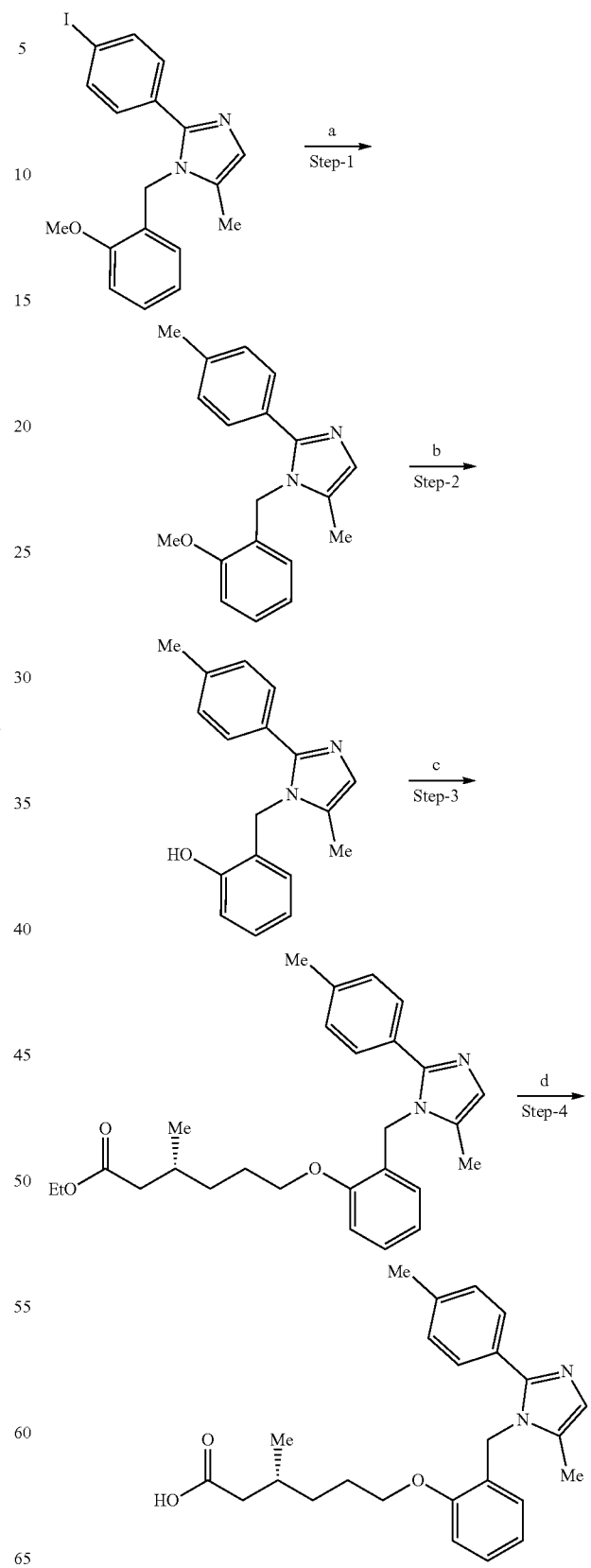

Step-1: Synthesis of 1-(2-methoxybenzyl)-5-methyl-2-(p-tolyl)-1H-imidazole

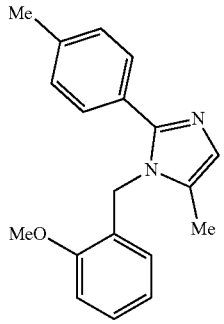

In a 50 mL re-sealable reaction tube, 2-(4-iodophenyl)-1-(2-methoxybenzyl)-5-methyl-1H-imidazole (0.4 g, 0.99 mmol) and methyl boronic acid (0.088 g, 1.48 mmol) were dissolved in degassed toluene (10 mL) at RT under nitrogen atmosphere. Pd(OAc)$_2$ (0.011 g, 0.049 mmol) tricyclohexyl phosphine (0.027 g, 0.09 mmol) and K$_3$PO$_4$ (0.63 g, 2.97 mmol) were added to the above solution under nitrogen atmosphere. The resulting mixture was degassed by purging argon gas for 15 min, and reaction mixture was heated to 90° C. until completion of the reaction (monitored by TLC). The reaction mixture was cooled to RT, diluted with cold water and washed with ethyl acetate (30 mL×3). The combined organic extract was washed with brine, dried over anhydrous Na$_2$SO$_4$ and concentrated under reduced pressure to get the title compound (0.26 g, 89.9%).

$^1$H NMR (400 MHz, CDCl$_3$): δ 7.37 (d, J=8.4 Hz, 2H), 7.29 (d, J=7.8 Hz, 1H), 7.14 (d, J=8.4 Hz, 2H), 6.97 (s, 1H), 6.91 (d, J=8.1 Hz, 2H), 6.62 (d, J=7.2 Hz, 1H), 5.12 (s, 2H), 3.84 (s, 3H), 2.34 (s, 3H), 2.10 (s, 3H).

Step-2: Synthesis of 2-((5-methyl-2-(p-tolyl)-1H-imidazol-1-yl)methyl)phenol

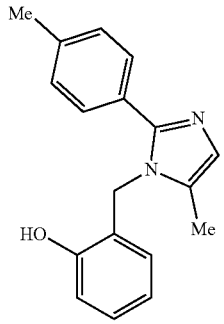

The title compound was synthesized from 1-(2-methoxybenzyl)-5-methyl-2-(p-tolyl)-1H-imidazole (0.25 g, 0.85 mmol) following the experimental procedure described in step-9 of Example-2a.

Yield: 0.23 g.

LCMS (ESI+, m/z): 279.3 (M+H)$^+$.

Step-3: Synthesis of ethyl (R)-3-methyl-6-(2-((5-methyl-2-(p-tolyl)-1H-imidazol-1-yl)methyl)phenoxy)hexanoate

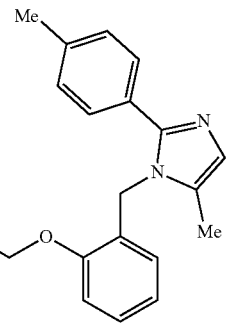

The title compound was synthesized from 2-((5-methyl-2-(p-tolyl)-1H-imidazol-1-yl)methyl)phenol (0.23 g, 0.83 mmol) and ethyl (R)-6-bromo-3-methylhexanoate (0.392 g, 1.65 mmol) following the experimental procedure described in step-1 of Example-2c.

Yield: 0.21 g (58.4%).

LCMS (ESI+, m/z): 436.5 (M+H)$^+$.

Step-4: Synthesis of (R)-3-methyl-6-(2-((5-methyl-2-(p-tolyl)-1H-imidazol-1-yl)methyl) phenoxy) hexanoic acid (Compound 2f)

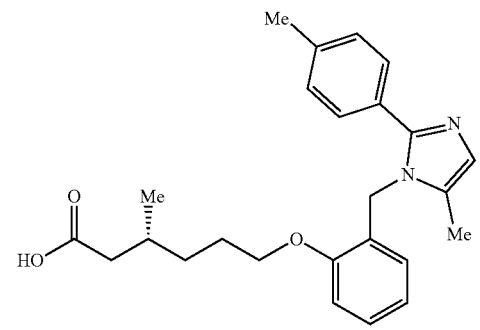 [SMILES: Cc1ccc(-c2ncc(C)n2Cc2ccccc2OCCC[C@@H](C)CC(=O)O)cc1]

The title compound was synthesized from ethyl (R)-3-methyl-6-(2-((5-methyl-2-(p-tolyl)-1H-imidazol-1-yl) methyl)phenoxy)hexanoate (0.2 g, 0.46 mmol) following the experimental procedure described in step-11 of Example-2a and purified by preparative HPLC [Luna C18 (21.2 mm×250 mm, 5 μm); flow: 18 mL/min; mobile phase: A/B=0.1% TFA in water/MeCN; T/% B=0/30, 2/40/8/80].

Yield: 0.029 g (15.5%).

$^1$H NMR (400 MHz, DMSO-d$_6$, 80° C.): δ 7.34 (d, J=8.0 Hz, 2H), 7.25-7.22 (m, 1H), 7.16 (d, J=8.0 Hz, 2H), 7.00 (d, J=8.0 Hz, 1H), 6.87-6.84 (m, 2H), 6.48 (brs, 1H), 5.13 (s, 2H), 4.04 (t, J=6.4 Hz, 2H), 2.30 (s, 3H), 2.14-2.13 (m, 1H), 2.07 (s, 3H), 2.05-1.99 (m, 1H), 1.91-1.86 (m, 1H), 1.71-1.69 (m, 2H), 1.48-1.40 (m, 1H), 1.35-1.23 (m, 1H), 0.91 (d, J=8.0 Hz, 3H).

LCMS (ESI+, m/z): 407.1 (M+H)$^+$.

HPLC: 99.28% (210 nm).

Example-2g

Synthesis of (R)-6-(2-((2-(4-fluorophenyl)-5-methyl-1H-imidazol-1-yl)methyl)phenoxy)-3-methylhexanoic acid (Compound 2g)

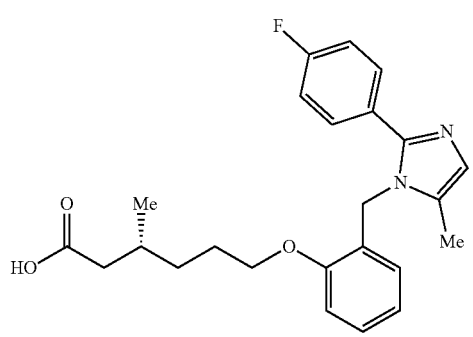 [SMILES: Cc1cnc(-c2ccc(F)cc2)n1Cc1ccccc1OCCC[C@@H](C)CC(=O)O]

Scheme

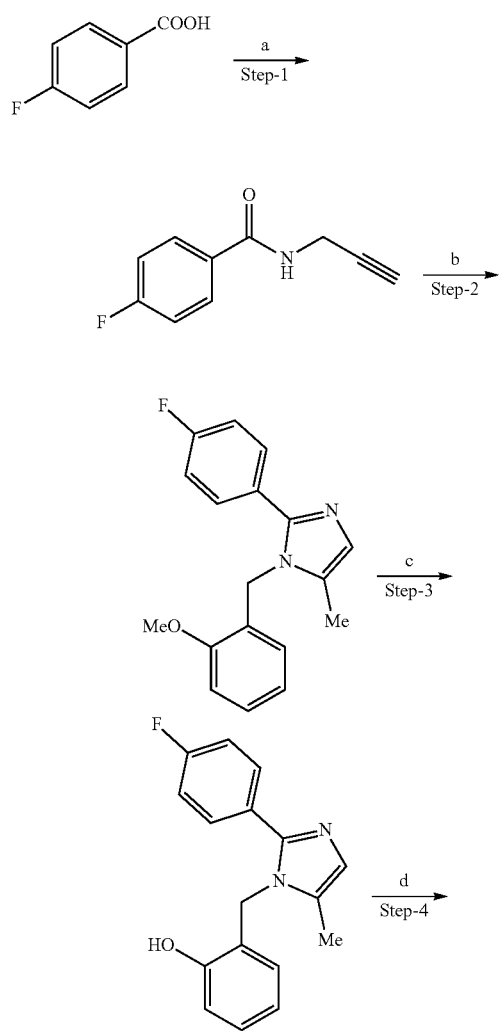

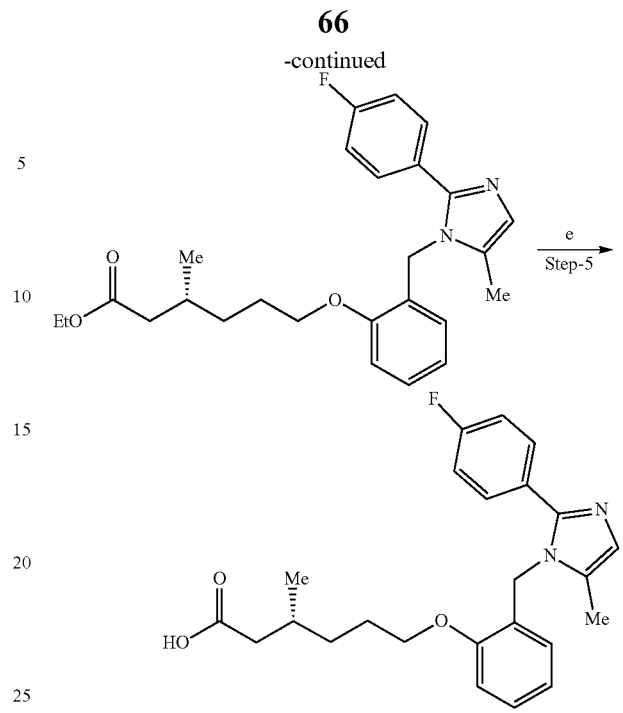

Step-1: Synthesis of 4-fluoro-N-(prop-2-yn-1-yl)benzamide

The title compound was synthesized from 4-fluorobenzoic acid (5.0 g, 35.68 mmol) and prop-2-yn-1-amine (2.35 g, 42.81 mmol) following the experimental procedure described in step-7 of Example-2a.

Yield: 4.25 g (67.22%).

$^1$H NMR (300 MHz, CDCl$_3$): δ 7.82-7.77 (m, 2H), 7.12 (t, J=8.4 Hz, 2H), 6.21 (bs, 1H), 4.26-4.23 (m, 2H), 2.29 (t, J=2.8 Hz, 1H).

Step-2: Synthesis of 2-(4-fluorophenyl)-1-(2-methoxybenzyl)-5-methyl-1H-imidazole The title compound was synthesized from 4-fluoro-N-(prop-2-yn-1-yl)benzamide (3.0 g, 16.93 mmol) and 2-methoxybenzyl amine (3.47 g, 25.39 mmol) following the experimental procedure described in step-8 of Example-2a.

Yield: 3.51 g (69.9%).

$^1$H NMR (300 MHz, CDCl$_3$): δ 7.46-7.41 (m, 2H), 7.30 (d, J=8.1 Hz, 1H), 7.04-6.87 (m, 5H), 6.58 (d, J=7.2 Hz, 1H), 5.08 (s, 2H), 3.85 (s, 3H), 2.11 (s, 3H).

$^{19}$F NMR (300 MHz, CDCl$_3$): δ −113.0

LCMS (ESI+, m/z): 297.3 (M+H)$^+$.

Step-3: Synthesis of 2-((2-(4-fluorophenyl)-5-methyl-1H-imidazol-1-yl)methyl)phenol

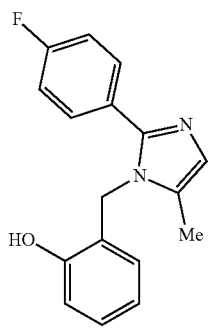 [SMILES: Cc1cnc(-c2ccc(F)cc2)n1Cc1ccccc1O]

The title compound was synthesized from 2-(4-fluorophenyl)-1-(2-methoxybenzyl)-5-methyl-1H-imidazole (3.5 g, 11.81 mmol) following the experimental procedure described in step-9 of Example-2a.

Yield: 2.7 g (81.1%).

LCMS (ESI+, m/z): 283.3 (M+H)$^+$.

Step-4: Synthesis of ethyl (R)-6-(2-((2-(4-fluorophenyl)-5-methyl-1H-imidazol-1-yl)methyl)phenoxy)-3-methylhexanoate

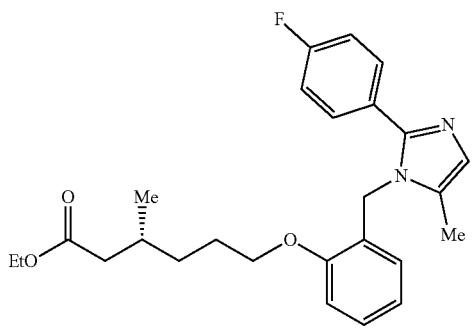

The title compound was synthesized from 2-((2-(4-fluorophenyl)-5-methyl-1H-imidazol-1-yl)methyl)phenol (0.6 g, 2.12 mmol) and ethyl (R)-6-bromo-3-methylhexanoate (1.51 g, 6.38 mmol) following the experimental procedure described in step-10 of Example-2a.

Yield: 0.62 g.

LCMS (ESI+, m/z): 439.4 (M+H)$^+$.

Step-5: Synthesis of (R)-6-(2-((2-(4-fluorophenyl)-5-methyl-1H-imidazol-1-yl)methyl) phenoxy)-3-methylhexanoic acid (Compound 2g)

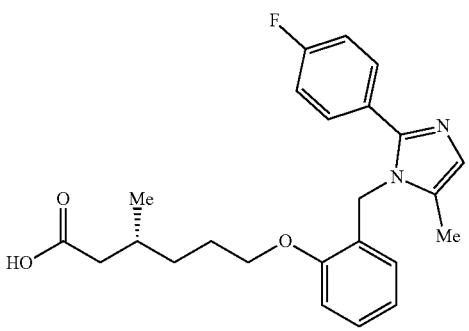

The title compound was synthesized from ethyl (R)-6-(2-(2-(4-fluorophenyl)-5-methyl-1H-imidazol-1-yl)methyl) phenoxy)-3-methylhexanoate (0.62 g, 1.41 mmol) following the experimental procedure described in step-11 of Example-2a and purified by preparative HPLC [Phenomenex Luna C 18 (21.2 mm×250 mm, 5 μm); flow: 15 mL/min; mobile phase: A/B=0.1% TFA in water/MeCN; T/% B=0/40, 2/40/8/80].

Yield: 0.111 g (18.9%).

$^1$H NMR (400 MHz, DMSO-d$_6$, 80° C.): δ 7.50-7.47 (m, 2H), 7.28-7.16 (m, 3H), 7.03 (d, J=8.0 Hz, 1H), 6.89-6.85 (m, 2H), 6.46 (d, J=7.2 Hz, 1H), 5.14 (s, 2H), 4.03 (t, J=5.6 Hz, 2H), 2.24-2.20 (m, 1H), 2.11 (s, 3H), 2.08-2.03 (m, 1H), 1.95-1.90 (m, 1H), 1.80-1.67 (m, 2H), 1.50-1.42 (m, 1H), 1.38-1.28 (m, 1H), 0.93 (d, J=6.8 Hz, 3H).

$^{19}$F NMR (400 MHz, DMSO-d$_6$): δ −113.00

LCMS (ESI+, m/z): 411.4 (M+H)$^+$.

HPLC: 99.3% (210 nm).

Example-2h

Synthesis of 6-(2-((2-(3-fluoro-4-(trifluoromethyl) phenyl)-5-methyl-1H-imidazol-1-yl)methyl)phenoxy)-2,2-dimethylhexanoic acid (Compound 2h)

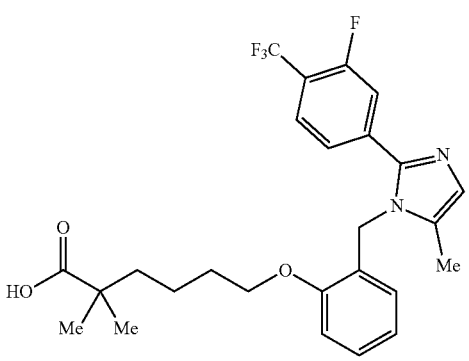

69

Scheme

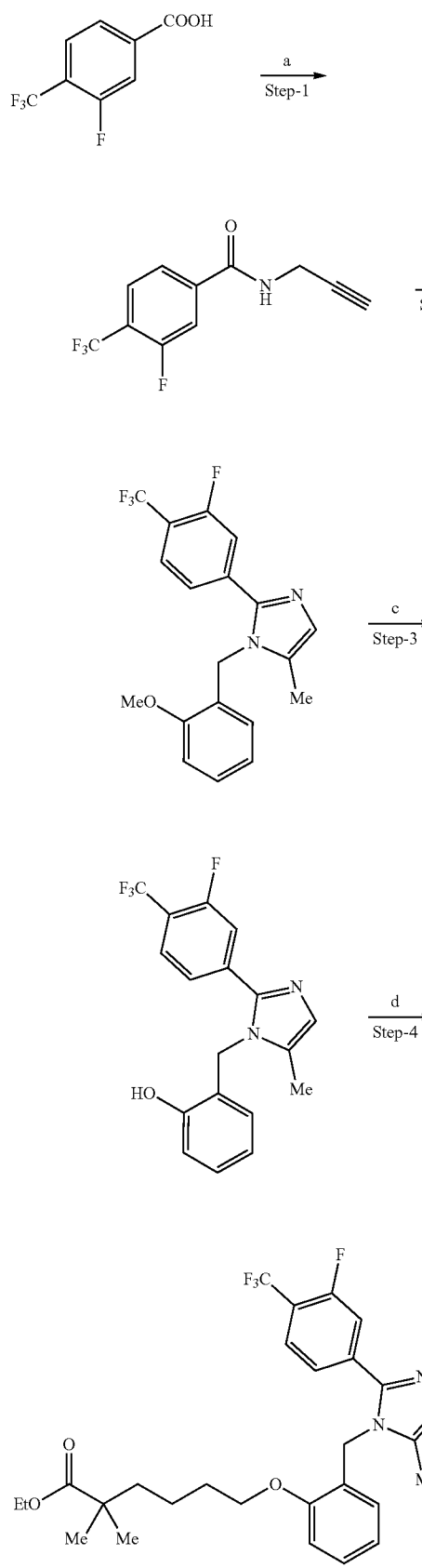

70

-continued

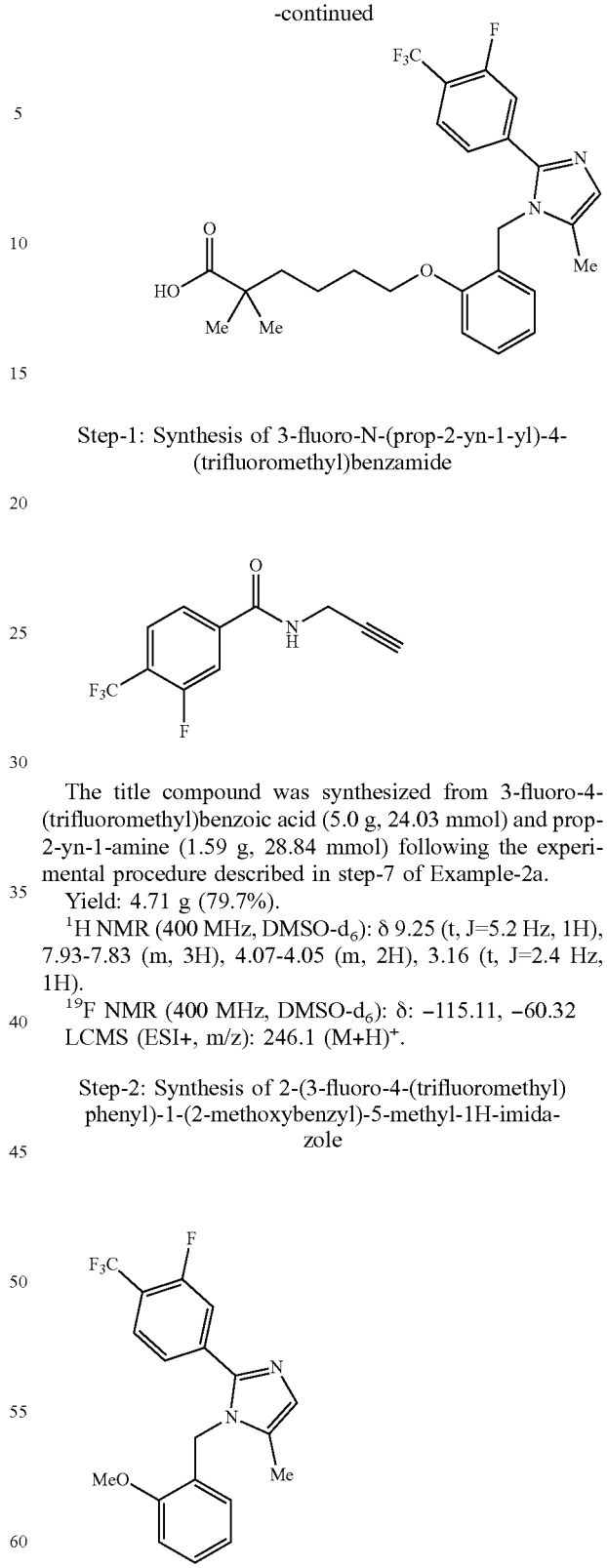

Step-1: Synthesis of 3-fluoro-N-(prop-2-yn-1-yl)-4-(trifluoromethyl)benzamide

The title compound was synthesized from 3-fluoro-4-(trifluoromethyl)benzoic acid (5.0 g, 24.03 mmol) and prop-2-yn-1-amine (1.59 g, 28.84 mmol) following the experimental procedure described in step-7 of Example-2a.

Yield: 4.71 g (79.7%).

$^1$H NMR (400 MHz, DMSO-$d_6$): δ 9.25 (t, J=5.2 Hz, 1H), 7.93-7.83 (m, 3H), 4.07-4.05 (m, 2H), 3.16 (t, J=2.4 Hz, 1H).

$^{19}$F NMR (400 MHz, DMSO-$d_6$): δ: −115.11, −60.32

LCMS (ESI+, m/z): 246.1 (M+H)$^+$.

Step-2: Synthesis of 2-(3-fluoro-4-(trifluoromethyl)phenyl)-1-(2-methoxybenzyl)-5-methyl-1H-imidazole The title compound was synthesized from 3-fluoro-N-(prop-2-yn-1-yl)-4-(trifluoromethyl)benzamide (2.5 g, 10.1 mmol) and 2-methoxybenzyl amine (2.1 g, 15.2 mmol) following the experimental procedure described in step-8 of Example-2a.

Yield: 2.3 g (61.8%).

$^1$H NMR (400 MHz, DMSO-d$_6$): δ 7.78 (t, J=7.8 Hz, 1H), 7.52 (d, J=12.3 Hz, 1H), 7.45 (d, J=8.4 Hz, 1H), 7.30-7.24 (m, 1H), 7.04 (d, J=7.8 Hz, 1H), 6.96 (s, 1H), 6.88-6.83 (m, 1H), 6.38 (d, J=7.5 Hz, 1H), 5.21 (s, 2H), 3.78 (s, 3H), 2.10 (s, 3H).

$^{19}$F NMR (400 MHz, DMSO-d$_6$): δ: −115.36, −59.90

LCMS (ESI+, m/z): 365.0 (M+H)$^+$.

Step-3: Synthesis of 2-((2-(3-fluoro-4-(trifluoromethyl)phenyl)-5-methyl-1H-imidazol-1-yl)methyl)phenol

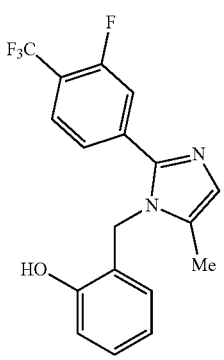 [SMILES: Cc1cnc(-c2ccc(C(F)(F)F)c(F)c2)n1Cc1ccccc1O]

The title compound was synthesized from 2-(3-fluoro-4-(trifluoromethyl)phenyl)-1-(2-methoxybenzyl)-5-methyl-1H-imidazole (1.0 g, 2.74 mmol) following the experimental procedure described in step-9 of Example-2a.

Yield: 1.1 g, (crude)

LCMS (ESI+, m/z): 351.2 (M+H)$^+$.

Step-4: Synthesis of ethyl 6-(2-((2-(3-fluoro-4-(trifluoromethyl)phenyl)-5-methyl-1H-imidazol-1-yl)methyl)phenoxy)-2,2-dimethylhexanoate

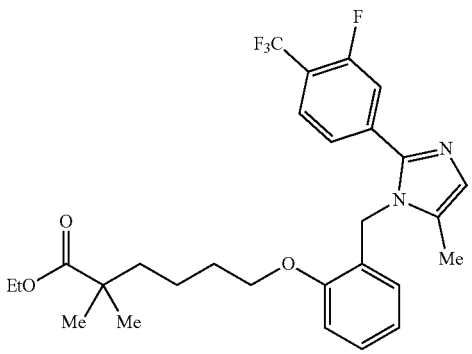 [SMILES: Cc1cnc(-c2ccc(C(F)(F)F)c(F)c2)n1Cc1ccccc1OCCCCC(C)(C)C(=O)O]

The title compound was synthesized from 2-((2-(3-fluoro-4-(trifluoromethyl)phenyl)-5-methyl-1H-imidazol-1-yl)methyl)phenol (0.5 g, 1.42 mmol) and ethyl 6-bromo-2,2-dimethylhexanoate (1.07 g, 4.28 mmol) (procedures for the preparation of which are disclosed in U.S. Application No. 62/061,483, incorporated herein by reference) following the experimental procedure described in step-1 of Example-2c.

Yield: 0.31 g (41.81%).

LCMS (ESI+, m/z): 520.7 (M+H)$^+$.

Step-5: Synthesis of 6-(2-((2-(3-fluoro-4-(trifluoromethyl)phenyl)-5-methyl-1H-imidazol-1-yl)methyl)phenoxy)-2,2-dimethylhexanoic acid (Compound 2h)

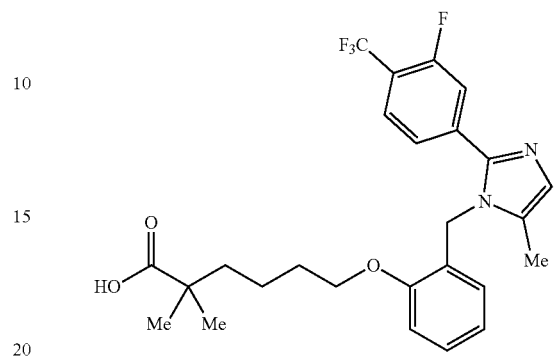

The title compound was synthesized from ethyl 6-(2-((2-(3-fluoro-4-(trifluoromethyl)phenyl)-5-methyl-1H-imidazol-1-yl)methyl)phenoxy)-2,2-dimethylhexanoate (0.3 g, 0.57 mmol) following the experimental procedure described in step-11 of Example-2a.

Yield: 0.120 g, (46.4%).

$^1$H NMR (400 MHz, DMSO-d$_6$, 80° C.): δ 7.73 (t, J=8.4 Hz, 1H), 7.49-7.45 (m, 2H), 7.26 (m, J=7.6 Hz, 1H), 7.04 (d, J=8.4 Hz, 1H), 6.96 (s, 1H), 6.86 (t, J=7.6 Hz, 1H), 6.46 (d, J=7.2 Hz, 1H), 5.23 (s, 2H), 4.03 (t, J=6.4 Hz, 2H), 2.14 (s, 3H), 1.71-1.67 (m, 2H), 1.53-1.49 (m, 2H), 1.41-1.36 (m, 2H), 1.06 (s, 6H).

$^{19}$F NMR (400 MHz, DMSO-d$_6$): δ −115.25, −59.87

LCMS (ESI+, m/z): 493.3 (M+H)$^+$.

HPLC: 97.62% (210 nm):

Example-2i

Synthesis of 6-(2-((2-(4-chloro-3-fluorophenyl)-5-methyl-1H-imidazol-1-yl)methyl)-phenoxy)-2,2-dimethylhexanoic acid (Compound 2i)

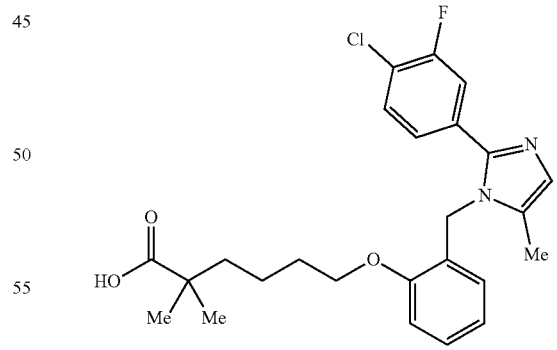

Scheme

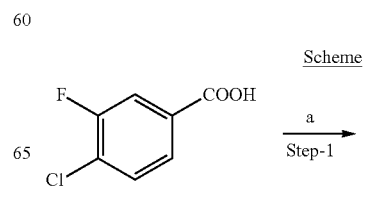

73
-continued

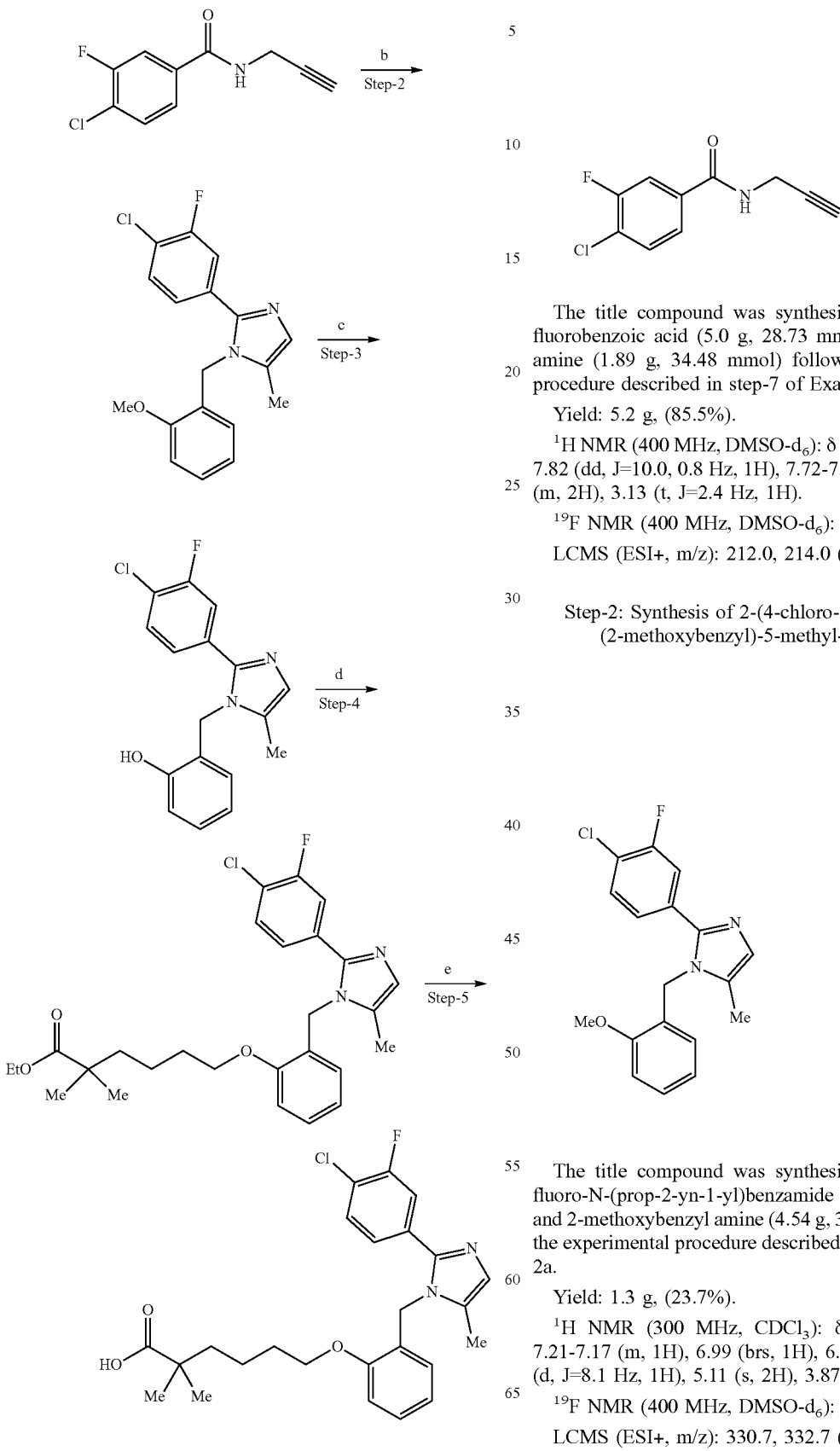

74

Step-1: Synthesis of 4-chloro-3-fluoro-N-(prop-2-yn-1-yl)benzamide

The title compound was synthesized from 4-chloro-3-fluorobenzoic acid (5.0 g, 28.73 mmol) and prop-2-yn-1-amine (1.89 g, 34.48 mmol) following the experimental procedure described in step-7 of Example-2a.

Yield: 5.2 g, (85.5%).

$^1$H NMR (400 MHz, DMSO-$d_6$): δ 9.09 (t, J=5.2 Hz, 1H), 7.82 (dd, J=10.0, 0.8 Hz, 1H), 7.72-7.69 (m, 2H), 4.04-4.02 (m, 2H), 3.13 (t, J=2.4 Hz, 1H).

$^{19}$F NMR (400 MHz, DMSO-$d_6$): δ: −115.48

LCMS (ESI+, m/z): 212.0, 214.0 (M+H)$^+$.

Step-2: Synthesis of 2-(4-chloro-3-fluorophenyl)-1-(2-methoxybenzyl)-5-methyl-1H-imidazole The title compound was synthesized from 4-chloro-3-fluoro-N-(prop-2-yn-1-yl)benzamide (3.5 g, 16.54 mmol) and 2-methoxybenzyl amine (4.54 g, 33.08 mmol) following the experimental procedure described in step-8 of Example-2a.

Yield: 1.3 g, (23.7%).

$^1$H NMR (300 MHz, CDCl$_3$): δ 7.36-7.28 (m, 3H), 7.21-7.17 (m, 1H), 6.99 (brs, 1H), 6.95-6.88 (m, 2H), 6.56 (d, J=8.1 Hz, 1H), 5.11 (s, 2H), 3.87 (s, 3H), 2.13 (s, 3H).

$^{19}$F NMR (400 MHz, DMSO-$d_6$): δ −114.79

LCMS (ESI+, m/z): 330.7, 332.7 (M+H)$^+$.

Step-3: Synthesis of 2-((2-(4-chloro-3-fluorophenyl)-5-methyl-1H-imidazol-1-yl)methyl)phenol

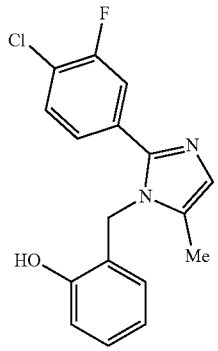 [SMILES: Cc1cnc(-c2ccc(Cl)c(F)c2)n1Cc1ccccc1O]

The title compound was synthesized from 2-(4-chloro-3-fluorophenyl)-1-(2-methoxybenzyl)-5-methyl-1H-imidazole (1.3 g, 3.93 mmol) following the experimental procedure described in step-9 of Example-2a.

Yield: 1.1 g, (88.7%).

LCMS (ESI+, m/z): 317.0, 319.0 (M+H)+.

Step-4: Synthesis of ethyl 6-(2-((2-(4-chloro-3-fluorophenyl)-5-methyl-1H-imidazol-1-yl)methyl)phenoxy)-2,2-dimethylhexanoate

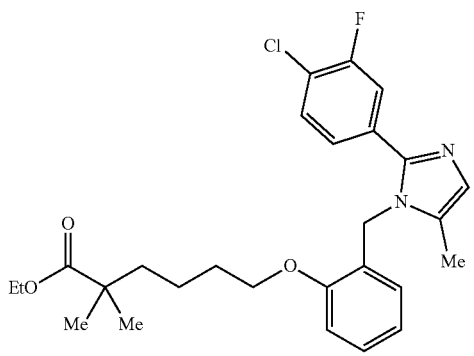 [SMILES: Cc1cnc(-c2ccc(Cl)c(F)c2)n1Cc1ccccc1OCCCCC(C)(C)C(=O)O]

The title compound was synthesized from 2-((2-(4-chloro-3-fluorophenyl)-5-methyl-1H-imidazol-1-yl)methyl)phenol (0.35 g, 1.11 mmol) and ethyl 6-bromo-2,2-dimethylhexanoate (0.831 g, 3.32 mmol) (procedures for the preparation of which are disclosed in U.S. Application No. 62/061,483, incorporated herein by reference) following the experimental procedure described in step-10 of Example-2a.

Yield: 0.25 g, (46.3%).

LCMS (ESI+, m/z): 486.9, 488.9 (M+H)+.

Step-5: Synthesis of 6-(2-((2-(4-chloro-3-fluorophenyl)-5-methyl-1H-imidazol-1-yl)methyl)phenoxy)-2,2-dimethylhexanoic acid (Compound 2i)

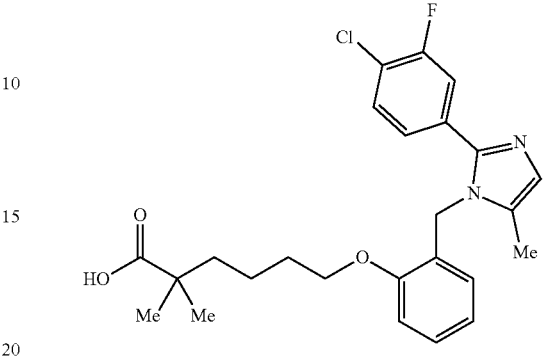

The title compound was synthesized from ethyl 6-(2-((2-(4-chloro-3-fluorophenyl)-5-methyl-1H-imidazol-1-yl)methyl)phenoxy)-2,2-dimethylhexanoate (0.25 g, 0.51 mmol) following the experimental procedure described in step-11 of Example-2a and purified by preparative HPLC [Column: Zorbax C18 (21.2 mm×150 mm, 5 μm); Flow: 20 mL/min; mobile phase: A/B=0.1% TFA in water/MeCN; T/% B=0/20, 2/20, 8/70].

Yield: 0.070 g (29.8%)

$^{1}$H NMR (400 MHz, DMSO-$d_6$, 80° C.): δ 12.02 (brs, 1H), 7.59 (t, J=8.0 Hz, 1H), 7.38 (d, J=10.8 Hz, 1H), 7.28-7.24 (m, 2H), 7.05 (d, J=8.4 Hz, 1H), 6.93 (s, 1H), 6.87 (t, J=7.6 Hz, 1H), 6.38 (d, J=7.6 Hz, 1H), 5.15 (s, 2H), 4.02 (t, J=6.0 Hz, 2H), 2.10 (s, 3H), 1.69-1.65 (m, 2H), 1.50-1.46 (m, 2H), 1.41-1.33 (m, 2H), 1.08 (s, 6H).

$^{19}$F NMR (400 MHz, DMSO-$d_6$): δ −110.89

LCMS (ESI+, m/z): 459.2, 461.2 (M+H)+.

HPLC: 98.95% (210 nm).

Example-2j

Synthesis of (R)-6-(2-((2-(4-chloro-3-fluorophenyl)-5-methyl-1H-imidazol-1-yl)methyl)phenoxy)-3-methylhexanoic acid (Compound 2j)

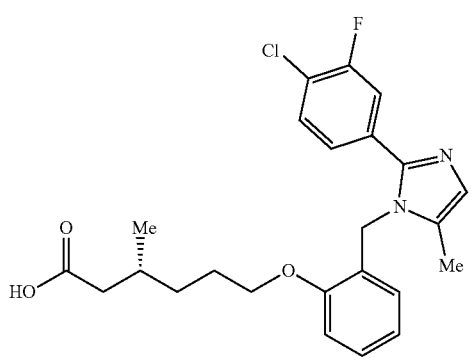 [SMILES: Cc1cnc(-c2ccc(Cl)c(F)c2)n1Cc1ccccc1OCCC[C@@H](C)CC(=O)O]

Scheme

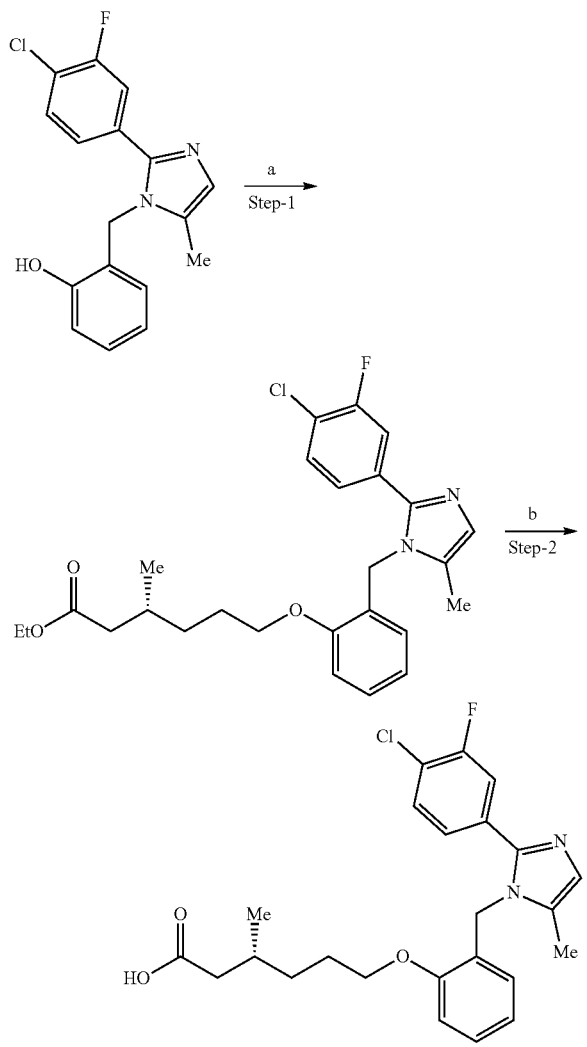

Step-1: Synthesis of ethyl (R)-6-(2-((2-(4-chloro-3-fluorophenyl)-5-methyl-1H-imidazol-1-yl)methyl)phenoxy)-3-methylhexanoate The title compound was synthesized from 2-((2-(4-chloro-3-fluorophenyl)-5-methyl-1H-imidazol-1-yl)methyl)phenol (0.350 g, 1.11 mmol) and ethyl (R)-6-bromo-3-methylhexanoate (0.784 g, 3.32 mmol) following the experimental procedure described in step-10 of Example-2a.

Yield: 0.15 g (28.6%).

LCMS (ESI+, m/z): 472.9, 474.9 (M+H)$^+$.

Step-2: Synthesis of (R)-6-(2-((2-(4-chloro-3-fluorophenyl)-5-methyl-1H-imidazol-1-yl)methyl)phenoxy)-3-methylhexanoic acid (Compound 2j)

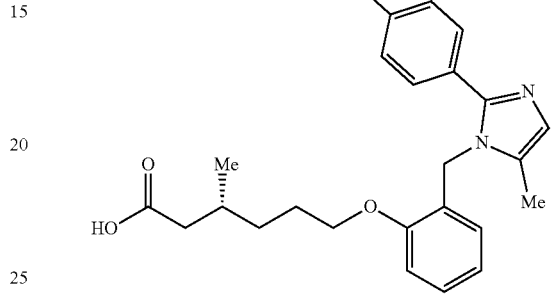

The title compound was synthesized from ethyl (R)-6-(2-((2-(4-chloro-3-fluorophenyl)-5-methyl-1H-imidazol-1-yl)methyl)phenoxy)-3-methylhexanoate (0.15 g, 0.32 mmol) following the experimental procedure described in step-11 of Example-2a.

Yield: 0.115 g (81.5%).

$^1$H NMR (400 MHz, DMSO-d$_6$, 80° C.): δ 12.02 (brs, 1H), 7.61 (t, J=8.0 Hz, 1H), 7.43 (d, J=10.8 Hz, 1H), 7.29-7.24 (m, 2H), 7.04 (d, J=8.4 Hz, 1H), 6.99 (s, 1H), 6.86 (t, J=7.6 Hz, 1H), 6.43 (d, J=7.6 Hz, 1H), 5.18 (s, 2H), 4.00 (t, J=6.4 Hz, 2H), 2.23-2.18 (m, 1H), 2.11 (s, 3H), 2.02-1.99 (m, 1H), 1.89-1.80 (m, 1H), 1.75-1.64 (m, 2H), 1.45-1.35 (m, 1H), 1.31-1.25 (m, 1H), 0.87 (d, J=6.8 Hz, 3H).

$^{19}$F NMR (400 MHz, DMSO-d$_6$): δ −115.50

LCMS (ESI+, m/z): 445.2, 447.2 (M+H)$^+$.

HPLC: 97.30% (210 nm).

Example-2k

Synthesis of (R)-6-(4-fluoro-2-((5-methyl-2-(4-(trifluoromethyl)phenyl)-1H-imidazol-1-yl)methyl)phenoxy)-3-methylhexanoic acid (Compound 2k)

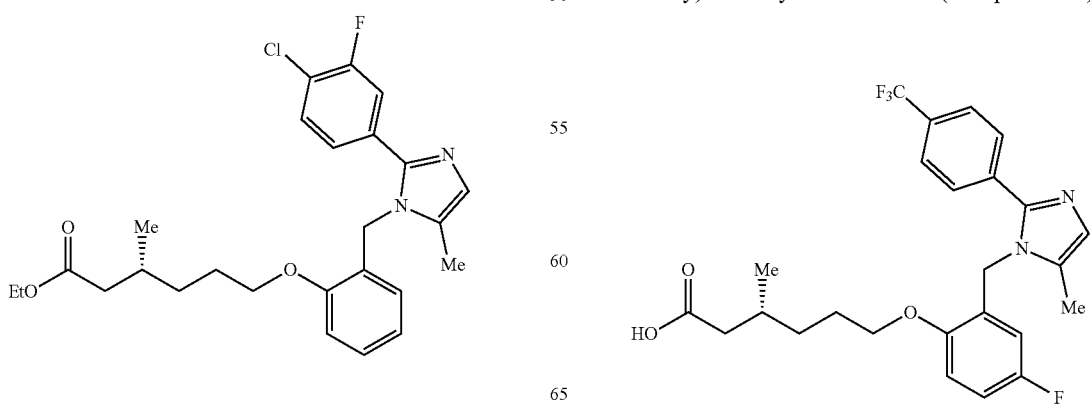

Scheme

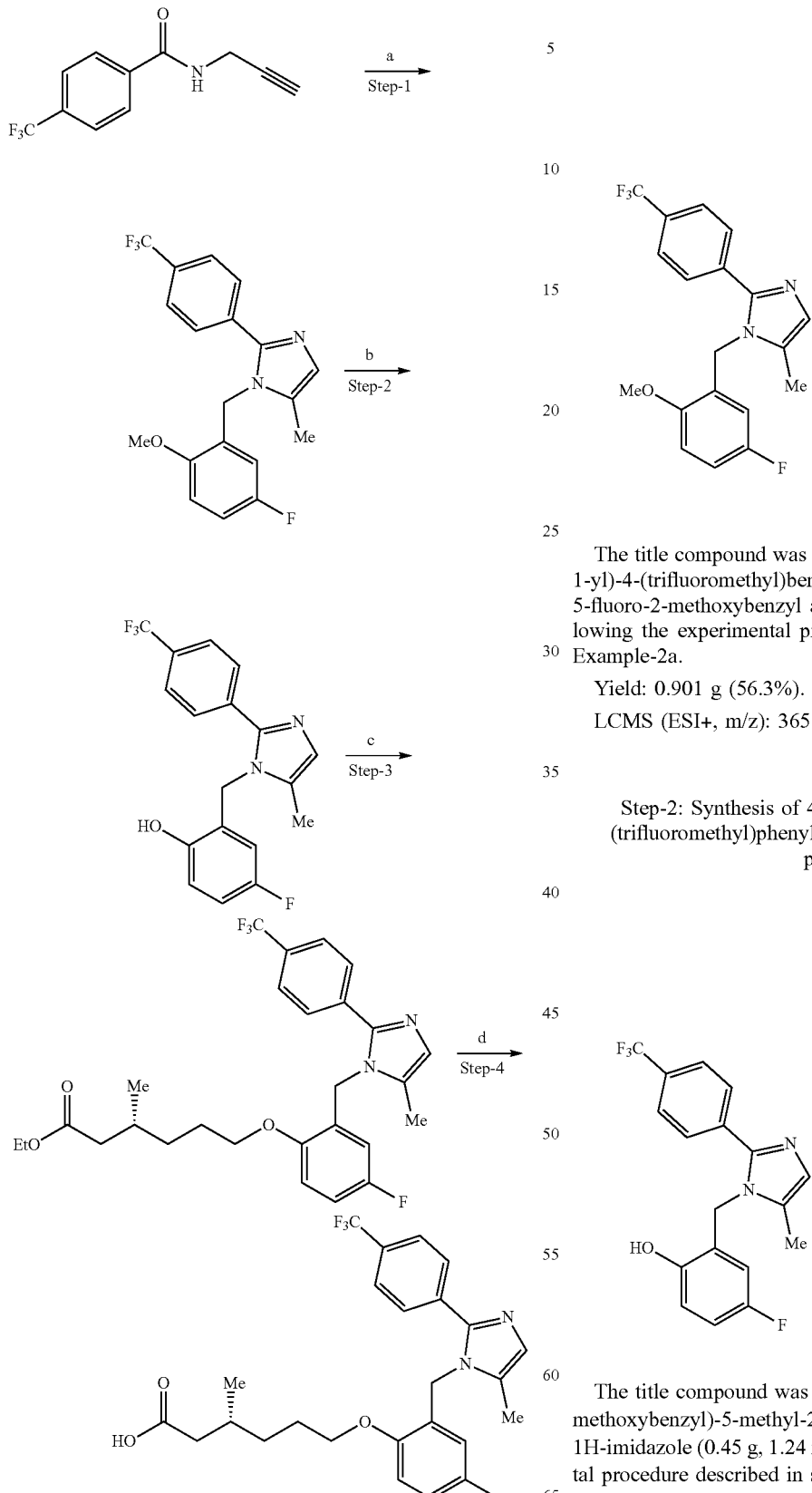

Step-1: Synthesis of 1-(5-fluoro-2-methoxybenzyl)-5-methyl-2-(4-(trifluoromethyl) phenyl)-1H-imidazole The title compound was synthesized from N-(prop-2-yn-1-yl)-4-(trifluoromethyl)benzamide (1.0 g, 4.39 mmol) and 5-fluoro-2-methoxybenzyl amine (1.36 g, 8.79 mmol) following the experimental procedure described in step-8 of Example-2a.

Yield: 0.901 g (56.3%).

LCMS (ESI+, m/z): 365.6 (M+H)$^+$.

Step-2: Synthesis of 4-fluoro-2-((5-methyl-2-(4-(trifluoromethyl)phenyl)-1H-imidazol-1-yl)methyl) phenol The title compound was synthesized from 1-(5-fluoro-2-methoxybenzyl)-5-methyl-2-(4-(trifluoromethyl)phenyl)-1H-imidazole (0.45 g, 1.24 mmol) following the experimental procedure described in step-9 of Example-2a.

Yield: 0.3 g (crude).

LCMS (ESI+, m/z): 350.9 (M+H)$^+$.

Step-3: Synthesis of ethyl (R)-6-(4-fluoro-2-((5-methyl-2-(4-(trifluoromethyl)phenyl)-1H-imidazol-1-yl)methyl)phenoxy)-3-methylhexanoate

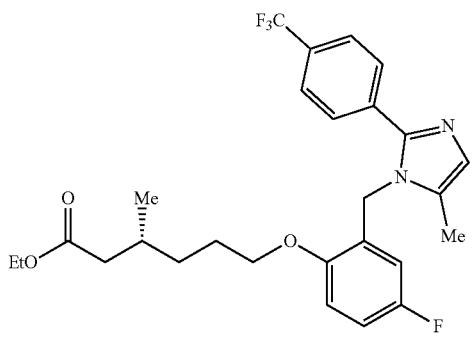 [SMILES: Cc1cnc(-c2ccc(C(F)(F)F)cc2)n1Cc1cc(F)ccc1OCCC[C@@H](C)CC(=O)O]

The title compound was synthesized from 4-fluoro-2-((5-methyl-2-(4-(trifluoromethyl)phenyl)-1H-imidazol-1-yl)methyl)phenol (0.3 g, 0.86 mmol) and ethyl (R)-6-bromo-3-methylhexanoate (0.61 g, 2.57 mmol) following the experimental procedure described in step-10 of Example-2a.

Yield: 0.2 g (46.2%).

LCMS (ESI+, m/z): 507.5 (M+H)+.

Step-4: Synthesis of (R)-6-(4-fluoro-2-((5-methyl-2-(4-(trifluoromethyl)phenyl)-1H-imidazol-1-yl)methyl)phenoxy)-3-methylhexanoic acid (Compound 2k)

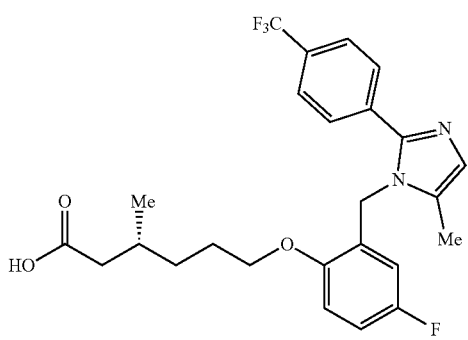 [SMILES: Cc1cnc(-c2ccc(C(F)(F)F)cc2)n1Cc1cc(F)ccc1OCCC[C@@H](C)CC(=O)O]

The title compound was synthesized from ethyl (R)-6-(4-fluoro-2-((5-methyl-2-(4-(trifluoromethyl)phenyl)-1H-imidazol-1-yl)methyl)phenoxy)-3-methylhexanoate (0.1 g, 0.19 mmol) following the experimental procedure described in step-11 of Example-2a.

Yield: 0.06 g (63.4%).

$^1$H NMR (400 MHz, DMSO-$d_6$): δ 12.08 (brs, 1H), 7.76 (d, J=8.0 Hz, 2H), 7.67 (d, J=7.6 Hz, 2H), 7.08 (d, J=8.4 Hz, 2H), 6.97 (s, 1H), 6.14 (brs, 1H), 5.18 (s, 2H), 3.97 (brs, 2H), 2.25-2.13 (m, 1H), 2.13 (s, 3H), 2.02-1.97 (m, 1H), 1.86-1.82 (m, 1H), 1.75-1.62 (m, 2H), 1.45-1.35 (m, 1H), 1.29-1.19 (m, 1H), 0.86 (d, J=6.4 Hz, 3H).

$^{19}$F NMR (400 MHz, DMSO-$d_6$): δ −123.14, −61.17

LCMS (ESI+, m/z): 478.8 (M+H)+.

HPLC: 94.6% (210 nm).

Example-21

Synthesis of (R)-6-(2-((2-(4-(difluoromethoxy)phenyl)-5-methyl-1H-imidazol-1-yl)methyl)phenoxy)-3-methylhexanoic acid (Compound 2l)

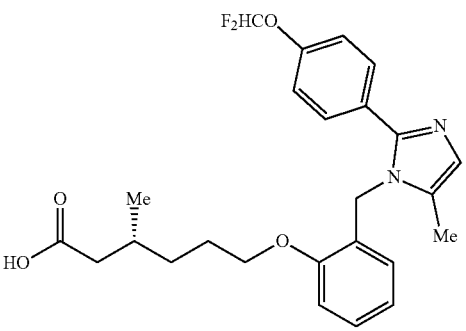 [SMILES: Cc1cnc(-c2ccc(OC(F)F)cc2)n1Cc1ccccc1OCCC[C@@H](C)CC(=O)O]

Scheme

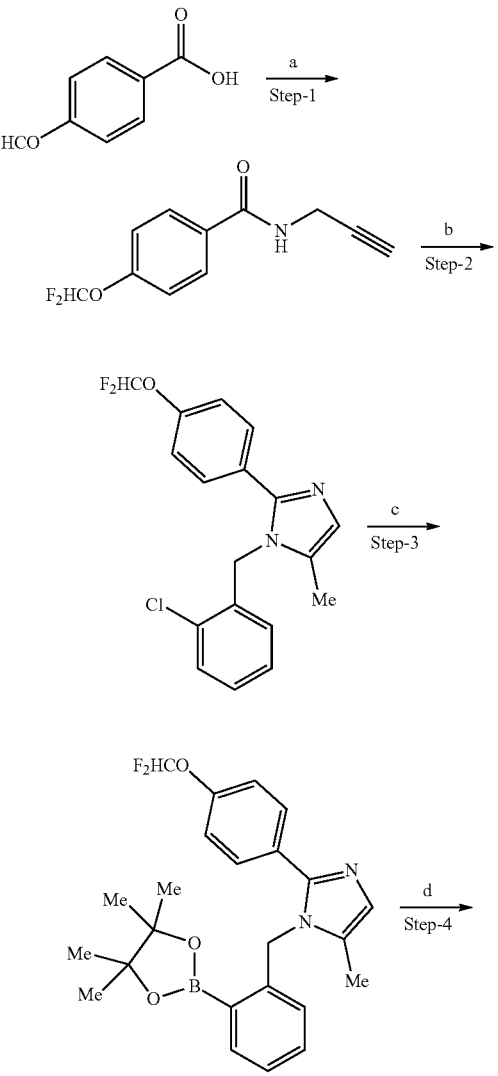

83
-continued

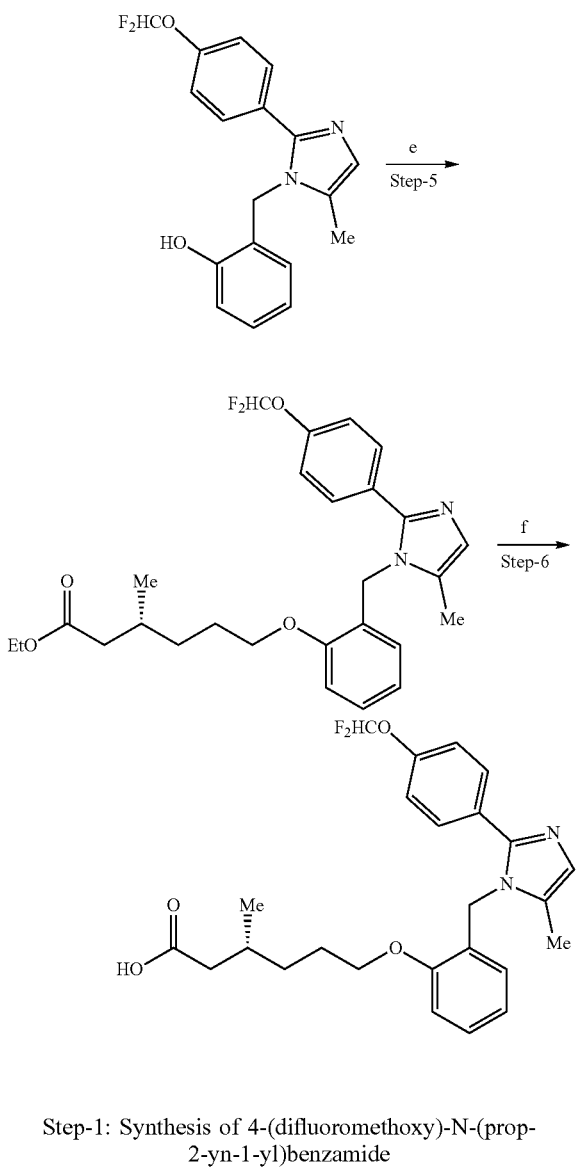

Step-1: Synthesis of 4-(difluoromethoxy)-N-(prop-2-yn-1-yl)benzamide

The title compound was synthesized from 4-(difluoromethoxy)benzoic acid (2.0 g, 10.63 mmol) and prop-2-yn-1-amine (0.70 g, 12.76 mmol) following the experimental procedure described in step-7 of Example-2a.

Yield: 1.61 g (66.9%).

$^1$H NMR (300 MHz, DMSO-$d_6$): δ 8.97 (t, J=5.1 Hz, 1H), 7.92 (d, J=8.7 Hz, 2H), 7.36 (t, J=73.8 Hz, 1H), 7.26 (d, J=8.7 Hz, 2H), 4.07-4.04 (m, 2H), 3.14 (t, J=2.4 Hz, 1H).

LCMS (ESI+, m/z): 226.0 (M+H)$^+$.

84

Step-2: Synthesis of 1-(2-chlorobenzyl)-2-(4-(difluoromethoxy)phenyl)-5-methyl-1H-imidazole

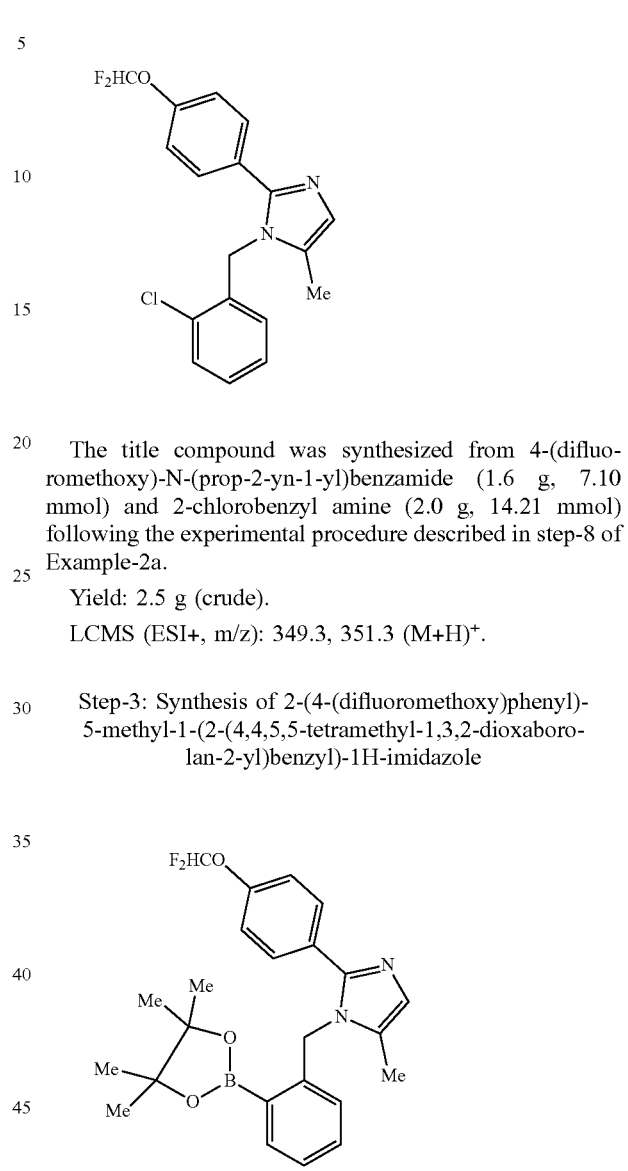

The title compound was synthesized from 4-(difluoromethoxy)-N-(prop-2-yn-1-yl)benzamide (1.6 g, 7.10 mmol) and 2-chlorobenzyl amine (2.0 g, 14.21 mmol) following the experimental procedure described in step-8 of Example-2a.

Yield: 2.5 g (crude).

LCMS (ESI+, m/z): 349.3, 351.3 (M+H)$^+$.

Step-3: Synthesis of 2-(4-(difluoromethoxy)phenyl)-5-methyl-1-(2-(4,4,5,5-tetramethyl-1,3,2-dioxaborolan-2-yl)benzyl)-1H-imidazole In a 100 mL re-sealable reaction tube, 1-(2-chlorobenzyl)-2-(4-(difluoromethoxy)phenyl)-5-methyl-1H-imidazole (1.0 g, 2.86 mmol) and 4,4,4',4',5,5,5',5'-octamethyl-2,2'-bi(1,3,2-dioxaborolane) (2.18 g, 8.60 mmol) were dissolved in degassed 1,4-dioxane (10 mL) at RT under nitrogen atmosphere. Pd$_2$(dba)$_3$ (0.13 g, 0.14 mmol), Xphos (0.14 g, 0.29 mmol) and KOAc (0.84 g, 8.61 mmol) were added to the above solution under nitrogen atmosphere. The resulting mixture was degassed by purging argon gas for 15 min, and reaction mixture was heated to 90° C. until completion of the reaction (monitored by TLC). The reaction mixture was cooled to RT. The solids were filtered through a Celite® pad and filtrate was washed with water (2×20 mL). The organic extract was dried over anhydrous Na$_2$SO$_4$ and solution was concentrated under reduced pressure. The residue obtained was purified using Combiflash MPLC (Silasep™, gradient elutions 50-60% EtOAc in hexanes) to give the title compound (0.45 g, 35.7%).

LCMS (ESI+, m/z): 441.2 (M+H)+

Step-4: Synthesis of 2-((2-(4-(difluoromethoxy)phenyl)-5-methyl-1H-imidazol-1-yl)methyl)phenol

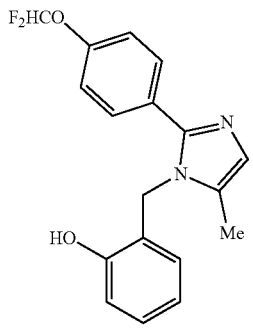 [SMILES: Cc1cnc(-c2ccc(OC(F)F)cc2)n1Cc1ccccc1O]

In a 100 mL round bottom flask, a solution of 2-(4-(difluoromethoxy)phenyl)-5-methyl-1-(2-(4,4,5,5-tetramethyl-1,3,2-dioxaborolan-2-yl)benzyl)-1H-imidazole (0.45 g, 1.02 mmol) in THF-H$_2$O (1:1, 10 mL) was treated with NaBO$_3$.4H$_2$O (0.47 g, 3.07 mmol) at RT. The reaction mixture was stirred at RT for 2 h. Upon completion of reaction (monitored by TLC), the reaction mixture was diluted with water and extracted with EtOAc. The organic extract was dried over anhydrous Na$_2$SO$_4$ and solution was concentrated under reduced pressure. The residue obtained was purified using Combiflash MPLC (Silasep™, gradient elutions, 50-60% EtOAc in hexanes) to give the title compound (0.33 g, 97.9%).

LCMS (ESI+, m/z): 331.4 (M+H)+.

Step-5: Synthesis of ethyl (R)-6-(2-((2-(4-(difluoromethoxy)phenyl)-5-methyl-1H-imidazol-1-yl)methyl)phenoxy)-3-methylhexanoate

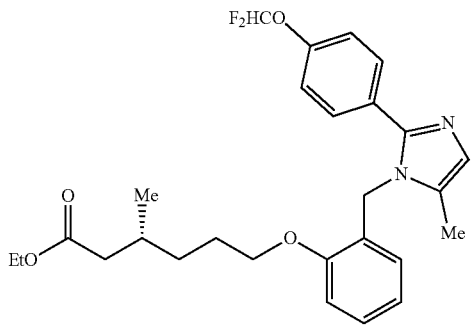

The title compound was synthesized from 2-((2-(4-(difluoromethoxy)phenyl)-5-methyl-1H-imidazol-1-yl)methyl)phenol (0.33 g, 0.99 mmol) and ethyl (R)-6-bromo-3-methylhexanoate (0.71 g, 2.99 mmol) following the experimental procedure described in step-10 of Example-2a.

Yield: 0.25 g (51.4%).

LCMS (ESI+, m/z): 487.6 (M+H)+.

Step-6: Synthesis of (R)-6-(2-((2-(4-(difluoromethoxy)phenyl)-5-methyl-1H-imidazol-1-yl)methyl)phenoxy)-3-methylhexanoic acid (Compound 2l)

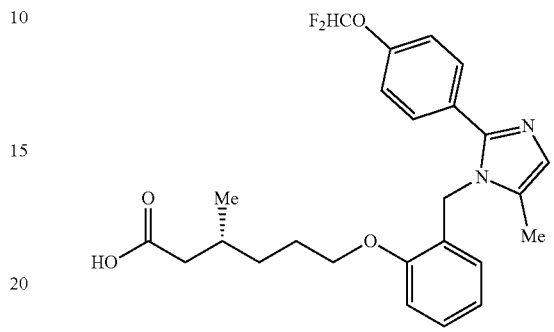

The title compound was synthesized from ethyl (R)-6-(2-((2-(4-(difluoromethoxy)phenyl)-5-methyl-1H-imidazol-1-yl)methyl)phenoxy)-3-methylhexanoate (0.1 g, 0.19 mmol) following the experimental procedure described in step-11 of Example-2a.

Yield: 0.05 g (53.2%).

$^1$H NMR (400 MHz, DMSO-d$_6$): δ 7.50 (d, J=8.8 Hz, 2H), 7.24 (t, J=7.6 Hz, 1H), 7.16 (d, J=8.8 Hz, 2H), 7.14 (d, J=74.0 Hz, 1H), 7.01 (d, J=8.8 Hz, 1H), 6.87-6.83 (m, 2H), 6.46 (d, J=7.6 Hz, 1H), 5.15 (s, 2H), 4.01 (t, J=6.4 Hz, 2H), 2.23-2.18 (m, 1H), 2.09 (s, 3H), 2.08-2.02 (m, 1H), 1.93-1.88 (m, 1H), 1.75-1.69 (m, 2H), 1.49-1.43 (m, 1H), 1.33-1.27 (m, 1H), 0.93 (d, J=6.4 Hz, 3H).

$^{19}$F NMR (400 MHz, DMSO-d$_6$): δ −82.36

LCMS (ESI+, m/z): 458.9 (M+H)+.

HPLC: 95.49% (210 nm).

Example-2m

Synthesis of (R)-3-methyl-6-(4-methyl-2-((5-methyl-2-(4-(trifluoromethoxy)phenyl)-1H-imidazol-1-yl)methyl)phenoxy)hexanoic acid (Compound 2m)

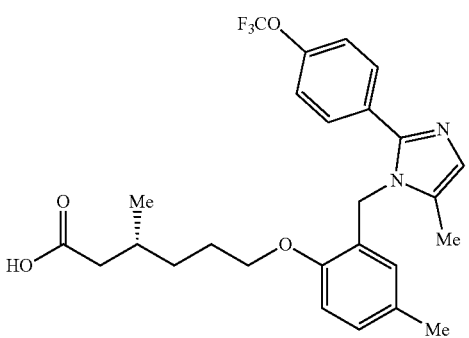 [SMILES: Cc1ccc(OCCC[C@@H](C)CC(=O)O)c(Cn2c(C)cnc2-c2ccc(OC(F)(F)F)cc2)c1]

Scheme

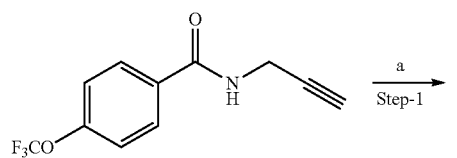

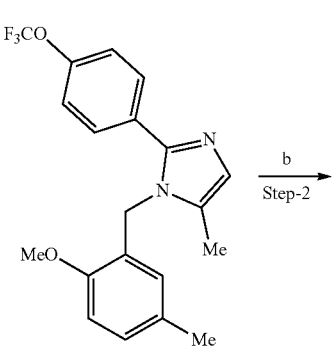

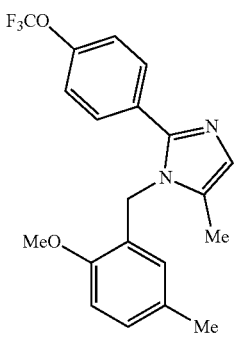 [SMILES: COc1ccc(C)cc1Cn1c(C)cnc1-c1ccc(OC(F)(F)F)cc1]

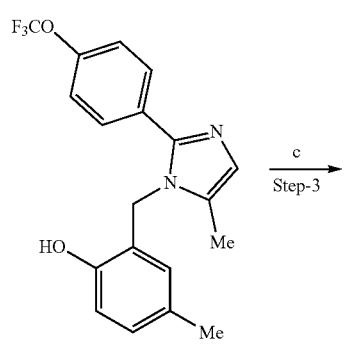

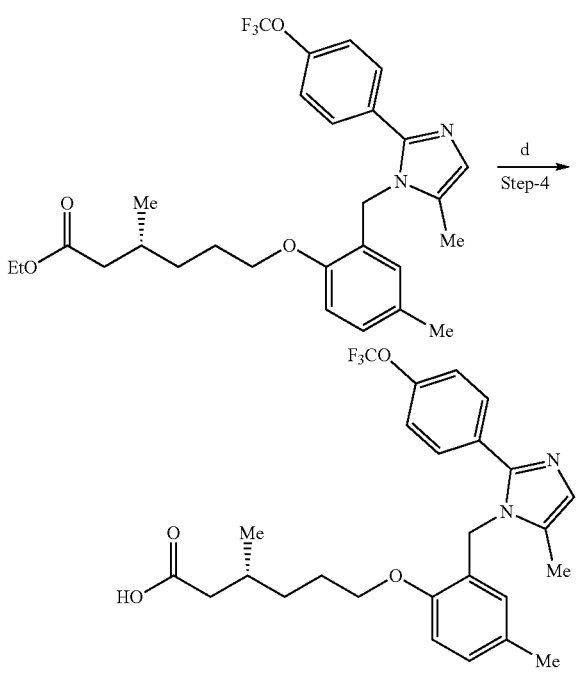

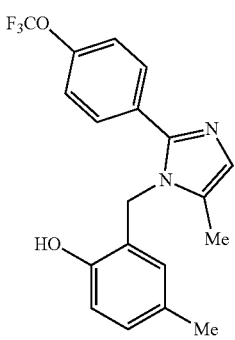 [SMILES: Cc1ccc(O)c(Cn2c(C)cnc2-c2ccc(OC(F)(F)F)cc2)c1]

Step-1: Synthesis of 1-(2-methoxy-5-methylbenzyl)-5-methyl-2-(4-(trifluoromethoxy)phenyl)-1H-imidazole The title compound was synthesized from N-(prop-2-yn-1-yl)-4-(trifluoromethoxy)benzamide (0.7 g, 2.88 mmol) and 2-methoxy-5-methylbenzyl amine (1.36 g, 8.79 mmol) following the experimental procedure described in step-8 of Example-2a.

Yield: 0.35 g (32.3%).

$^1$H NMR (300 MHz, CDCl$_3$): δ 7.51 (d, J=6.9 Hz, 2H), 7.17 (d, J=8.0 Hz, 2H), 7.09 (d, J=8.1 Hz, 1H), 6.98 (s, 1H), 6.81 (d, J=8.1 Hz, 1H), 6.38 (s, 1H), 5.08 (s, 2H), 3.83 (s, 3H), 2.19 (s, 3H), 2.12 (s, 3H).

LCMS (ESI+, m/z): 377.3 (M+H)$^+$.

Step-2: Synthesis of 4-methyl-2-((5-methyl-2-(4-(trifluoromethoxy)phenyl)-1H-imidazol-1-yl) methyl)phenol The title compound was synthesized from 1-(2-methoxy-5-methylbenzyl)-5-methyl-2-(4-(trifluoromethoxy)phenyl)-1H-imidazole (0.35 g, 0.93 mmol) following the experimental procedure described in step-9 of Example-2a.

Yield: 0.22 g (65.4%).

LCMS (ESI+, m/z): 363.3 (M+H)$^+$.

89

Step-3: Synthesis of ethyl (R)-3-methyl-6-(4-methyl-2-((5-methyl-2-(4-(trifluoromethoxy)phenyl)-1H-imidazol-1-yl)methyl)phenoxy)hexanoate

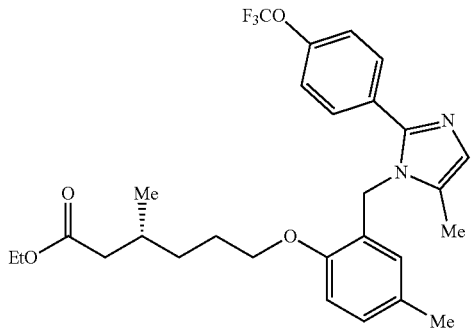

The title compound was synthesized from 4-methyl-2-((5-methyl-2-(4-(trifluoromethoxy)phenyl)-1H-imidazol-1-yl)methyl)phenol (0.1 g, 0.27 mmol) and ethyl (R)-6-bromo-3-methylhexanoate (0.196 g, 0.83 mmol) following the experimental procedure described in step-10 of Example-2a.

Yield: 0.14 g (98.5%).

LCMS (ESI+, m/z): 519.0 (M+H)$^+$.

Step-4: Synthesis of (R)-3-methyl-6-(4-methyl-2-((5-methyl-2-(4-(trifluoromethoxy)phenyl)-1H-imidazol-1-yl)methyl)phenoxy)hexanoic acid (Compound 2m)

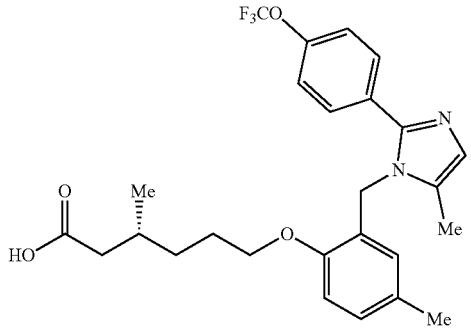

The title compound was synthesized from ethyl (R)-3-methyl-6-(4-methyl-2-((5-methyl-2-(4-(trifluoromethoxy)phenyl)-1H-imidazol-1-yl)methyl)phenoxy)hexanoate (0.15 g, 0.29 mmol) following the experimental procedure described in step-11 of Example-2a.

Yield: 0.01 g (10.6%).

$^1$H NMR (400 MHz, DMSO-d$_6$, 90° C.): δ 7.57 (d, J=8.4 Hz, 2H), 7.27 (d, J=8.0 Hz, 2H), 6.99 (d, J=8.0 Hz, 1H), 6.85-6.82 (m, 2H), 6.36 (s, 1H), 5.09 (s, 2H), 3.89 (d, J=4.8 Hz, 2H), 2.09 (s, 6H), 2.08-2.03 (m, 2H), 1.86-1.82 (m, 1H), 1.60-1.59 (m, 2H), 1.38-1.18 (m, 2H), 0.87 (d, J=6.4 Hz, 3H).

LCMS (ESI+, m/z): 490.8 (M+H)$^+$.

HPLC: 95.7% (210 nm).

90

Example-2n

Synthesis of (R)-3-methyl-6-(2-((5-methyl-2-(6-(trifluoromethyl)pyridin-3-yl)-1H-imidazol-1-yl)methyl)phenoxy)hexanoic acid (Compound 2n)

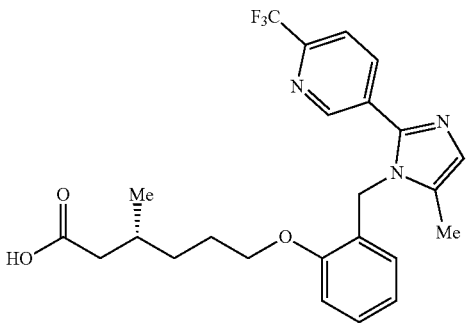

Scheme

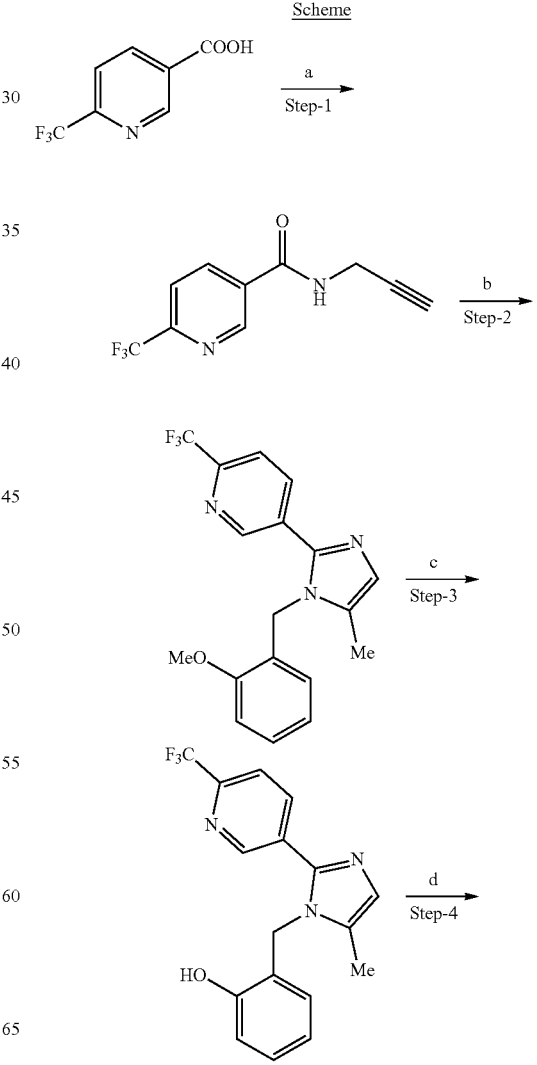

91
-continued

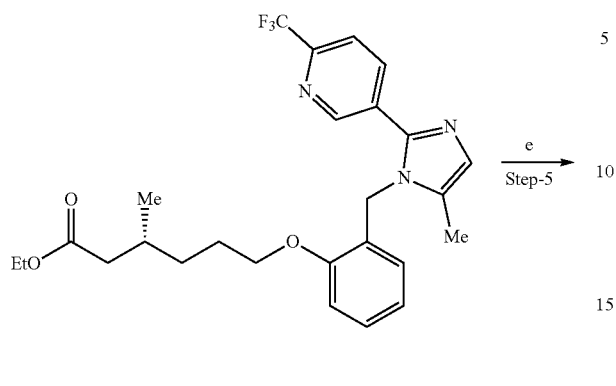

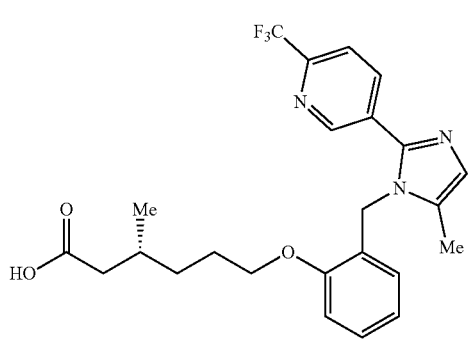

Step-1: Synthesis of N-(prop-2-yn-1-yl)-6-(trifluoromethyl)nicotinamide

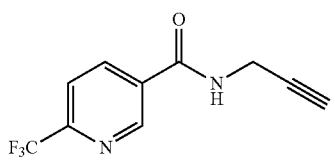 [SMILES: C#CCNC(=O)c1ccc(C(F)(F)F)nc1]

In a 100 mL round bottom flask, a stirred solution of 6-(trifluoromethyl)nicotinic acid (3 g, 15.70 mmol) and prop-2-yn-1-amine (1.05 g, 18.84 mmol) in DMF (50 mL) was treated with HATU (7.2 g, 18.84 mmol) and Et₃N (3.1 mL, 23.55 mmol) at RT under nitrogen atmosphere. The resulting reaction mixture was stirred at RT for 3 h. Upon completion of reaction (monitored by TLC), the reaction mixture was diluted with cold water and solid precipitated was filtered, washed with water and dried under reduced pressure to get the title compound (2.6 g, 72.6%).

¹H NMR (300 MHz, CDCl₃): δ 9.08 (d, J=2.1 Hz, 1H), 8.32 (dd, J=8.4, 2.4 Hz, 1H), 7.78 (d, J=7.8 Hz, 1H), 6.62 (brs, 1H), 4.30-4.28 (m, 2H), 2.33 (t, J=2.4 Hz, 1H).

LCMS (ESI+, m/z): 229.2 (M+H)⁺.

92

Step-2: Synthesis of 5-(1-(2-methoxybenzyl)-5-methyl-1H-imidazol-2-yl)-2-(trifluoromethyl) pyridine

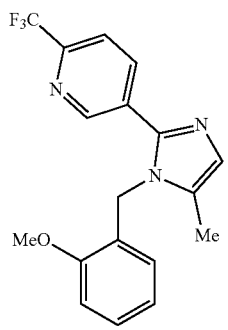 [SMILES: COc1ccccc1Cn1c(C)cnc1-c1ccc(C(F)(F)F)nc1]

The title compound was synthesized from N-(prop-2-yn-1-yl)-6-(trifluoromethyl)nicotinamide (1.0 g, 4.38 mmol) and 2-methoxyphenybenzyl amine (1.2 g, 8.77 mmol) following the experimental procedure described in step-8 of Example-2a.

Yield: 0.8 g (52.6%).

¹H NMR (400 MHz, CDCl₃): δ 8.79 (s, 1H), 8.07 (d, J=8.1 Hz, 1H), 7.68 (d, J=8.1 Hz, 1H), 7.31 (t, J=8.4 Hz, 1H), 7.09 (s, 1H), 6.94-6.87 (m, 2H), 6.56 (d, J=7.5 Hz, 1H), 5.16 (s, 2H), 3.87 (s, 3H).

LCMS (ESI+, m/z): 348.3 (M+H)⁺.

Step-3: Synthesis of 2-((5-methyl-2-(6-(trifluoromethyl)pyridin-3-yl)-1H-imidazol-1-yl) methyl)phenol

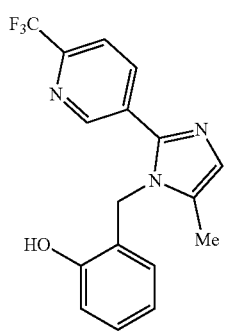 [SMILES: Cc1cnc(-c2ccc(C(F)(F)F)nc2)n1Cc1ccccc1O]

The title compound was synthesized from 5-(1-(2-methoxybenzyl)-5-methyl-1H-imidazol-2-yl)-2-(trifluoromethyl)pyridine (0.8 g, 2.31 mmol) following the experimental procedure described in step-9 of Example-2a.

Yield: 0.5 g (65.1%).

¹H NMR (400 MHz, DMSO-d₆): δ 9.92 (s, 1H), 8.83 (s, 1H), 8.12 (d, J=8.1 Hz, 1H), 7.94 (d, J=8.1 Hz, 1H), 7.12 (d, J=6.9 Hz, 1H), 7.02 (s, 1H), 6.87 (d, J=7.8 Hz 1H), 6.73 (t, J=7.2 Hz, 1H), 6.37 (d, J=7.2 Hz, 1H), 5.20 (s, 2H), 2.15 (s, 3H).

LCMS (ESI+, m/z): 334.3 (M+H)⁺.

Step-4: Synthesis of ethyl (R)-3-methyl-6-(2-((5-methyl-2-(6-(trifluoromethyl)pyridin-3-yl)-1H-imidazol-1-yl)methyl)phenoxy)hexanoate

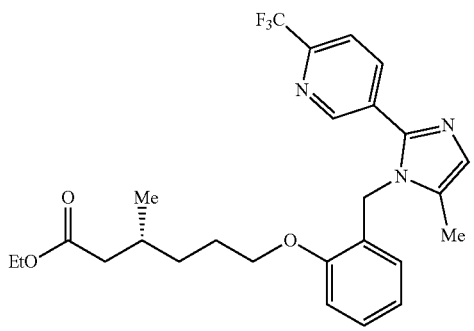 [SMILES: Cc1cnc(-c2ccc(C(F)(F)F)nc2)n1Cc1ccccc1OCCC[C@@H](C)CC(=O)O]

The title compound was synthesized from 2-((5-methyl-2-(6-(trifluoromethyl)pyridin-3-yl)-1H-imidazol-1-yl)methyl)phenol (0.5 g, 1.50 mmol) and ethyl (R)-6-bromo-3-methylhexanoate (0.710 g, 3.00 mmol) following the experimental procedure described in step-1 of Example-2c.

Yield: 0.45 g (61.3%).

LCMS (ESI+, m/z): 491.0 (M+H)$^+$.

Step-5: Synthesis of (R)-3-methyl-6-(2-((5-methyl-2-(6-(trifluoromethyl)pyridin-3-yl)-1H-imidazol-1-yl)methyl)phenoxy)hexanoic acid (Compound 2n)

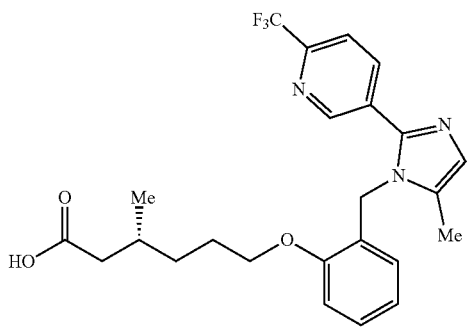

The title compound was synthesized from ethyl (R)-3-methyl-6-(2-((5-methyl-2-(6-(trifluoromethyl)pyridin-3-yl)-1H-imidazol-1-yl)methyl)phenoxy)hexanoate (0.45 g, 0.92 mmol) following the experimental procedure described in step-11 of Example-2a.

Yield: 0.166 g (39.2%).

$^1$H NMR (400 MHz, DMSO-d$_6$): δ11.96 (brs, 1H), 8.79 (s, 1H), 8.05 (d, J=8.0 Hz, 1H), 7.90 (d, J=8.0 Hz, 1H), 7.24 (t, J=7.6 Hz, 1H), 7.02 (d, J=8.4 Hz, 1H), 7.00 (s, 1H), 6.84 (t, J=7.6 Hz, 1H), 6.43 (d, J=7.2 Hz, 1H), 5.21 (s, 2H), 3.98 (t, J=6.0 Hz, 2H), 2.19-2.14 (m, 1H), 2.13 (s, 3H), 2.03-1.94 (m, 1H), 1.85-1.80 (m, 1H), 1.68-1.66 (m, 2H), 1.38-1.36 (m, 1H), 1.28-1.18 (m, 1H), 0.85 (d, J=6.4 Hz, 3H).

$^{19}$F NMR (400 MHz, DMSO-d$_6$): δ -66.46

LCMS (ESI+, m/z): 462.3 (M+H)$^+$.

HPLC: 95.11% (210 nm).

Preparation of Meglumine Salt of Compound 2n

Two separate methods were used to generate a meglumine salt of compound 2n.

Method 1

Compound 2n (102.7 mg) was combined with meglumine (43.7 mg) and 2 mL of 2-propanol in a 4 mL glass vial. The vial was sealed with a cap and the contents were subjected to sonication at 25° C. for 20 minutes followed by stirring at 50° C. for 60 minutes. The vial was then moved to a new stir plate and the slurry in the vial was stirred at 25° C.

Method 2

Compound 2n (102.2 mg) was combined with meglumine (43.2 mg) and 2 mL of acetonitrile in a 4 mL glass vial. The vial was sealed with a cap and the contents were subjected to sonication at 25° C. for 20 minutes followed by stirring at 50° C. for 60 minutes. The vial was then moved to a new stir plate and the slurry in the vial was stirred at 25° C.

For both method 1 and method 2, after 2 days of stirring at 25° C., both samples were centrifuged, supernatants discarded, and solids were air dried.

Preparation of Hydrate of Meglumine Salt of Compound 2n

In a 500 mL round bottom flask, a stirred solution of ((R)-3-methyl-6-(2-((5-methyl-2-(6-(trifluoromethyl) pyridin-3-yl)-1H-imidazol-1-yl)methyl)phenoxy)hexanoic acid (20 g, 43.33 mmol) in THF (100 mL) and water (100 mL) was treated meglumine (8.45 g, 43.33 mmol) at 0° C. The resulting reaction mixture was stirred at RT for 6 h. The reaction mixture was concentrated under reduced pressure and solid obtained was dried under reduced pressure (3 h) to afford the title compound as a white solid (28.5 g, 98.95%).

$^1$H NMR (400 MHz, CD$_3$OD): δ 8.75 (s, 1H), 8.02 (d, J=8.4 Hz, 1H), 7.82 (d, J=8.0 Hz 1H), 7.26 (t, J=8.4 Hz, 1H), 7.03 (s, 1H), 6.99 (d, J=8 Hz, 1H), 6.85 (t, J=7.6 Hz, 1H), 6.50 (d, J=7.6 Hz, 1H), 5.25 (s, 2H), 4.09-3.99 (m, 3H), 3.97-3.77 (m, 2H), 3.74-3.61 (m, 3H), 3.29-3.06 (m, 2H), 2.64 (s, 3H), 2.22 (s, 3H), 2.18-2.14 (m, 1H), 1.99-1.94 (m, 2H), 1.83-1.75 (m, 2H), 1.51-1.38 (m, 1H), 1.32-1.22 (m, 1H), 0.86 (d, J=6.0 Hz, 3H).

$^{19}$F NMR (400 MHz, CD$_3$OD): δ -69.39

Elemental Analysis: Calcd for C$_{31}$H$_{43}$F$_3$N$_4$O$_8$·H$_2$O: C, 55.18; H, 6.72; N, 8.30. Found: C, 54.95; H, 6.89; N, 8.07.

Moisture Content (Karl Fischer): 2.33%

Example-2o

Synthesis of (R)-6-(2-((2-(4-(difluoromethyl)phenyl)-5-methyl-1H-imidazol-1-yl)methyl) phenoxy)-3-methylhexanoic acid (Compound 2o)

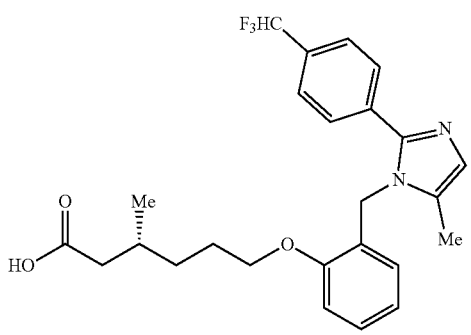 [SMILES: Cc1cnc(-c2ccc(C(F)F)cc2)n1Cc1ccccc1OCCC[C@@H](C)CC(=O)O]

Scheme

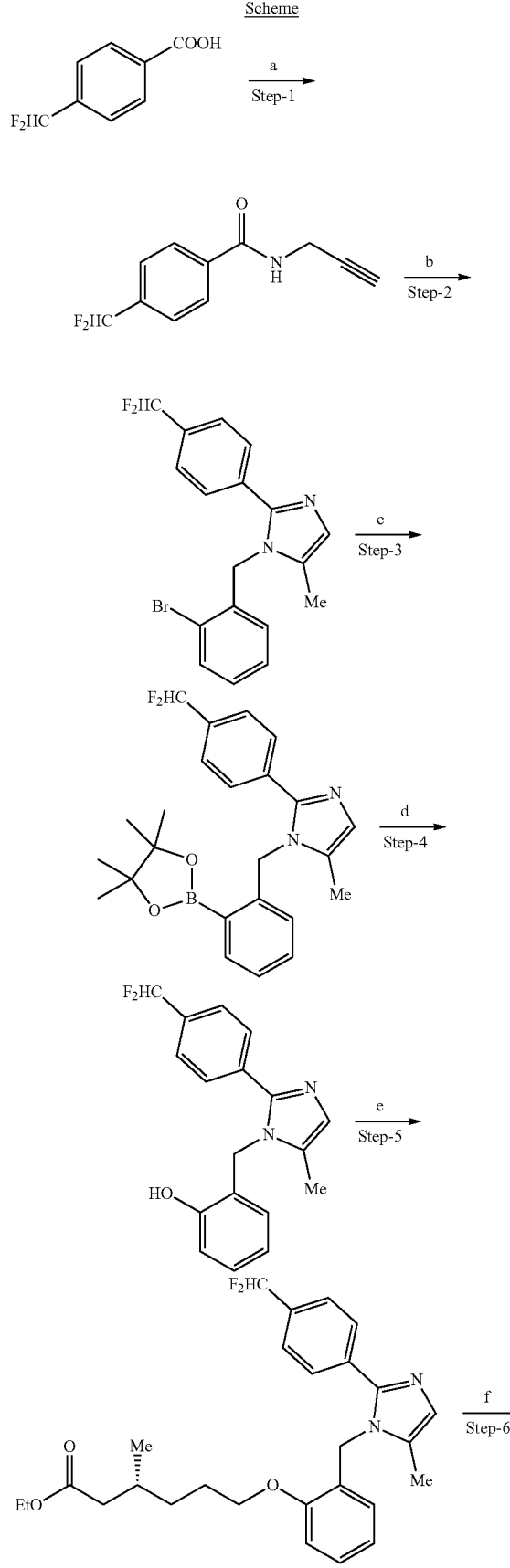

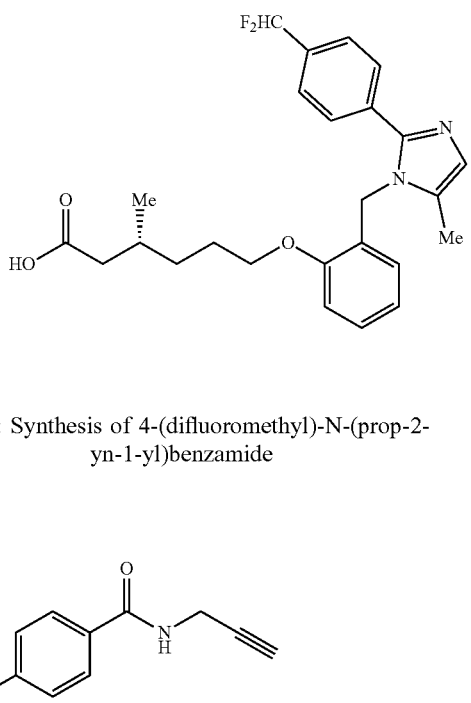

Step-1: Synthesis of 4-(difluoromethyl)-N-(prop-2-yn-1-yl)benzamide

The title compound was synthesized from 4-(difluoromethyl)benzoic acid (2.0 g, 11.61 mmol) and prop-2-yn-1-amine (0.77 g, 13.94 mmol) following the experimental procedure described in step-7 of Example-2a.

Yield: 1.5 g (62.5%).

$^1$H NMR (400 MHz, CDCl$_3$): δ 7.88 (d, J=8.0 Hz, 2H), 7.60 (d, J=8.0 Hz, 2H), 6.70 (t, J=56.0 Hz, 1H), 6.47 (brs, 1H), 4.29-4.27 (m, 2H), 2.31 (t, J=2.4 Hz, 1H).

Step-2: Synthesis of 1-(2-bromobenzyl)-2-(4-(difluoromethyl)phenyl)-5-methyl-1H-imidazole The title compound was synthesized from 4-(difluoromethyl)-N-(prop-2-yn-1-yl)benzamide (3.0 g, 14.44 mmol) and 2-bromobenzyl amine (5.4 g, 28.88 mmol) following the experimental procedure described in step-8 of Example-2a.

Yield: 2.3 g (43.3%).

$^1$H NMR (300 MHz, CDCl$_3$): δ 7.65 (dd, J=7.8, 1.2 Hz, 1H), 7.55-7.48 (m, 4H), 7.32-7.19 (m, 2H), 7.04 (m, 1H), 6.64 (t, J=56.0 Hz, 1H), 6.63-6.62 (m, 1H), 5.16 (s, 2H), 2.13 (s, 3H).

LCMS (ESI+, m/z): 376.8, 378.8 (M+H)+.

Step-3: Synthesis of 2-(4-(difluoromethyl)phenyl)-5-methyl-1-(2-(4,4,5,5-tetramethyl-1,3,2-dioxaborolan-2-yl)benzyl)-1H-imidazole

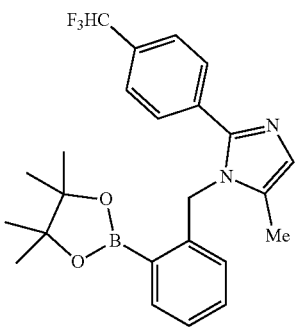

The title compound was synthesized from 1-(2-bromobenzyl)-2-(4-(difluoromethyl)phenyl)-5-methyl-1H-imidazole (0.5 g, 1.32 mmol) following the experimental procedure described in step-3 of Example-2l.

Yield: 0.18 g (32.2%).

¹H NMR (300 MHz, CDCl₃): δ 7.92 (dd, J=7.2, 1.5 Hz, 1H), 7.59 (d, J=8.4 Hz, 2H), 7.46 (d, J=8.1 Hz, 2H), 7.42-7.36 (m, 1H), 7.32-7.26 (m, 1H), 7.02 (bs, 1H), 6.75 (d, J=7.8 Hz, 1H), 6.62 (t, J=56.1 Hz, 1H), 5.48 (s, 2H), 2.11 (s, 3H), 1.31-1.23 (s, 12).

¹⁹F NMR (300 MHz, CDCl₃): δ −111.02

LCMS (ESI+, m/z): 424.0 (M+H)+.

Step-4: Synthesis of 2-((2-(4-(difluoromethyl)phenyl)-5-methyl-1H-imidazol-1-yl)methyl)phenol

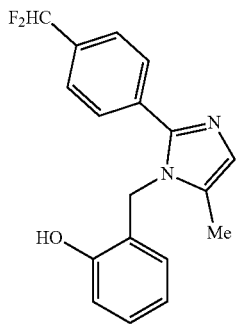

The title compound was synthesized from 2-(4-(difluoromethyl)phenyl)-5-methyl-1-(2-(4,4,5,5-tetramethyl-1,3,2-dioxaborolan-2-yl)benzyl)-1H-imidazole (0.18 g, 0.424 mmol) following the experimental procedure described in step-4 of Example-2l.

Yield: 0.12 g (44.4%).

LCMS (ESI+, m/z): 314.7 (M+H)+.

Step-5: Synthesis of ethyl (R)-6-(2-((2-(4-(difluoromethyl)phenyl)-5-methyl-1H-imidazol-1-yl)methyl)phenoxy)-3-methylhexanoate

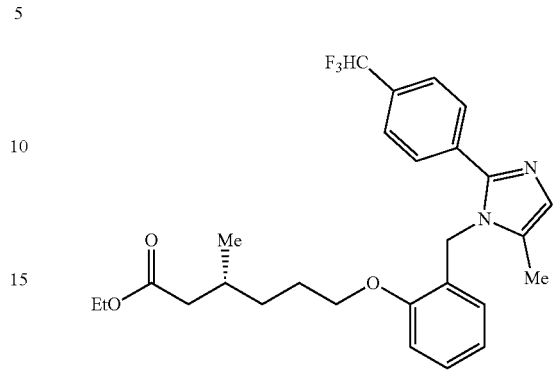

The title compound was synthesized from 2-((2-(4-(difluoromethyl)phenyl)-5-methyl-1H-imidazol-1-yl)methyl)phenol (0.11 g, 1.5 mmol) and ethyl (R)-6-bromo-3-methylhexanoate (0.25 g, 1.05 mmol) following the experimental procedure described in step-1 of Example-2c.

Yield: 0.13 g (crude).

LCMS (ESI+, m/z): 471.1 (M+H)+.

Step-6: Synthesis of (R)-6-(2-((2-(4-(difluoromethyl)phenyl)-5-methyl-1H-imidazol-1-yl)methyl)phenoxy)-3-methylhexanoic acid (Compound 2o)

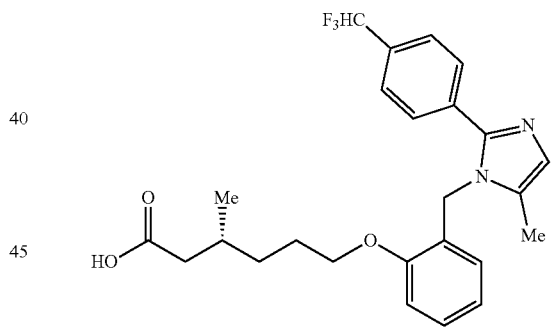

The title compound was synthesized from ethyl (R)-6-(2-((2-(4-(difluoromethyl)phenyl)-5-methyl-1H-imidazol-1-yl)methyl)phenoxy)-3-methylhexanoate (0.30 g, 0.638 mmol) following the experimental procedure described in step-11 of Example-2a.

Yield: 0.091 g (32.3%).

¹H NMR (400 MHz, DMSO-d₆): δ 12.03 (s, 1H), 7.57 (bs, 4H), 7.26-7.23 (m, 1H), 7.04-7.01 (m, 1H), 7.02 (t, J=56.0 Hz, 1H), 6.93 (s, 1H), 6.90-6.84 (m, 1H), 6.39-6.37 (m, 1H), 5.16 (s, 2H), 3.99 (t, J=6.4 Hz, 2H), 2.19-2.17 (m, 1H), 2.09 (s, 3H), 2.02-1.97 (m, 1H), 1.86-1.84 (m, 1H), 1.70-1.62 (m, 2H), 1.45-1.42 (m, 1H), 1.28-1.18 (m, 1H), 0.87 (d, J=6.4 Hz, 2H).

¹⁹F NMR (400 MHz, DMSO-d₆): δ −110.00

LCMS (ESI+, m/z): 443.0 (M+H)+.

HPLC: 95.65% (210 nm).

Example-2p

Synthesis of (R)-3-methyl-6-(2-((5-methyl-2-(4-(methylthio)phenyl)-1H-imidazol-1-yl)methyl)phenoxy)hexanoic acid (Compound 2p)

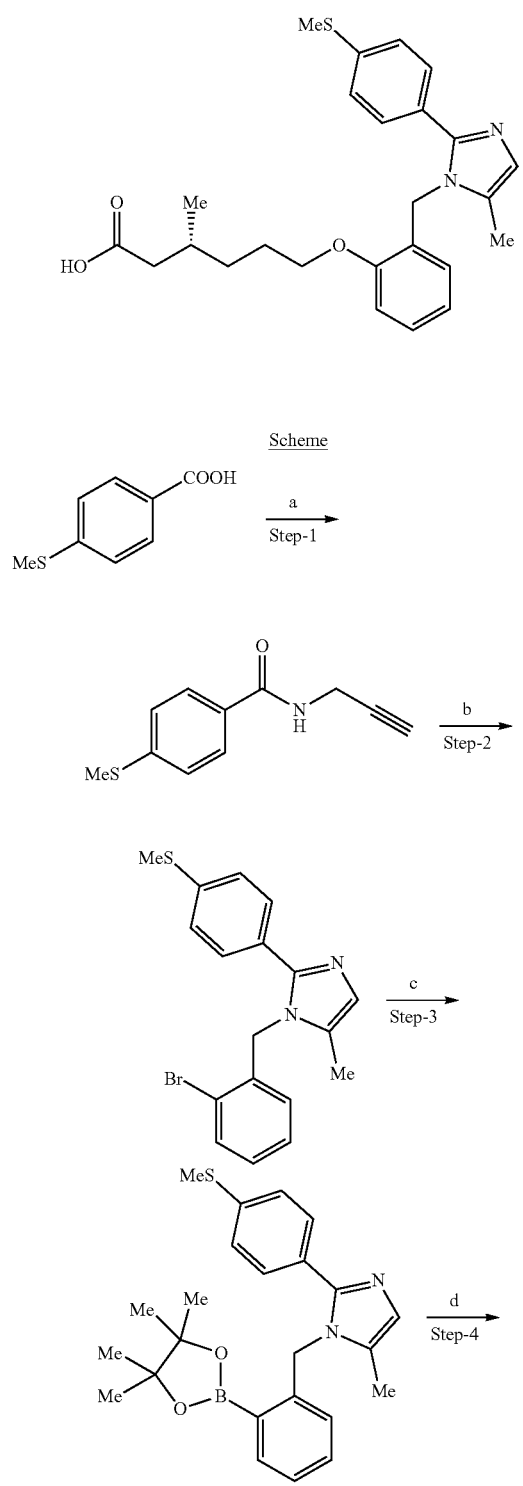

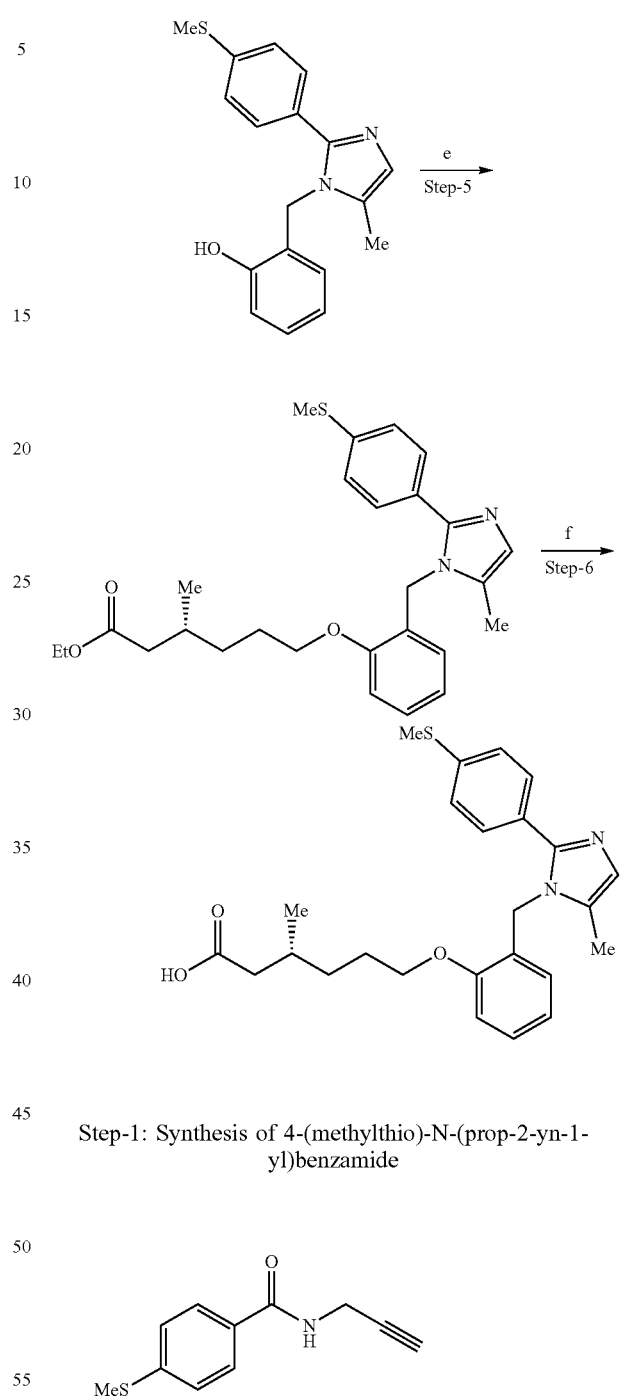

Step-1: Synthesis of 4-(methylthio)-N-(prop-2-yn-1-yl)benzamide

The title compound was synthesized from 4-(methylthio)benzoic acid (12.0 g, 58.53 mmol) and prop-2-yn-1-amine (5.89 g, 107.14 mmol) following the experimental procedure described in step-7 of Example-2a.

Yield: 13.81 g (94.5%).

$^1$H NMR (300 MHz, CDCl$_3$): δ 7.70 (d, J=8.4 Hz, 2H), 7.26 (d, J=8.4 Hz, 2H), 6.32 (brs, 1H), 4.26-4.24 (m, 2H), 2.51 (s, 3H), 2.29 (t, J=2.7 Hz, 1H).

LCMS (ESI+, m/z): 206.3 (M+H)$^+$.

Step-2: Synthesis of 1-(2-bromobenzyl)-5-methyl-2-(4-(methylthio)phenyl)-1H-imidazole

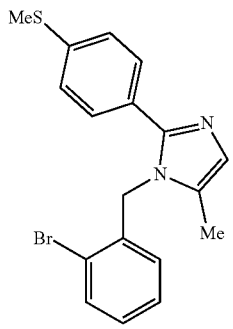

The title compound was synthesized from 4-(methylthio)-N-(prop-2-yn-1-yl)benzamide (3.0 g, 14.63 mmol) and 2-bromobenzyl amine, (4.0 g, 21.95 mmol) following the experimental procedure described in step-8 of Example-2a.

Yield: 4.38 g (80.3%).

LCMS (ESI+, m/z): 372.9, 374.9 (M+H)+.

Step-3: Synthesis of 5-methyl-2-(4-(methylthio)phenyl)-1-(2-(4,4,5,5-tetramethyl-1,3,2-dioxaborolan-2-yl)benzyl)-1H-imidazole

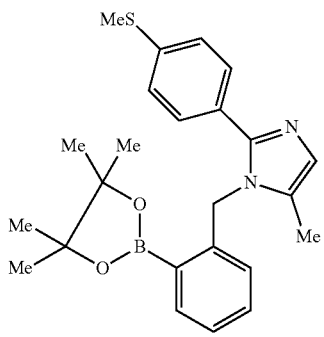 [SMILES: CSc1ccc(-c2ncc(C)n2Cc2ccccc2B2OC(C)(C)C(C)(C)O2)cc1]

The title compound was synthesized from 1-(2-bromobenzyl)-5-methyl-2-(4-(methylthio)phenyl)-1H-imidazole (1.5 g, 4.02 mmol) and 4,4,4',4',5,5,5',5'-octamethyl-2,2'-bi(1,3,2-dioxaborolane) (1.22 g, 4.82 mmol) following the experimental procedure described in step-3 of Example-2l.

Yield: 2.1 g

LCMS (ESI+, m/z): 421.2 (M+H)+

Step-4: Synthesis of 2-((5-methyl-2-(4-(methylthio)phenyl)-1H-imidazol-1-yl)methyl)phenol

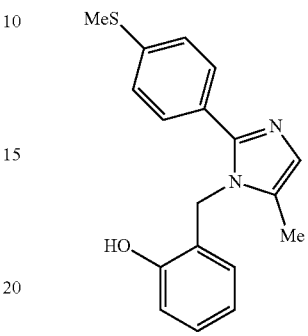

The title compound was synthesized from 5-methyl-2-(4-(methylthio)phenyl)-1-(2-(4,4,5,5-tetramethyl-1,3,2-dioxaborolan-2-yl)benzyl)-1H-imidazole (1.0 g, 2.38 mmol) following the experimental procedure described in step-4 of Example-2l.

Yield: 0.530 g.

LCMS (ESI+, m/z): 311.4 (M+H)+.

Step-5: Synthesis of ethyl (R)-3-methyl-6-(2-((5-methyl-2-(4-(methylthio)phenyl)-1H-imidazol-1-yl)methyl)phenoxy)hexanoate

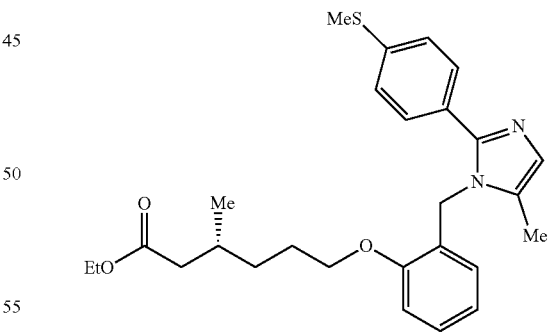

The title compound was synthesized from 2-((5-methyl-2-(4-(methylthio)phenyl)-1H-imidazol-1-yl)methyl)phenol (0.3 g, 0.96 mmol) and ethyl (R)-6-bromo-3-methylhexanoate (0.685 g, 2.90 mmol) following the experimental procedure described in step-1 of Example-2c.

Yield: 0.43 g

LCMS (ESI+, m/z): 467.3 (M+H)+.

Step-6: Synthesis of (R)-3-methyl-6-(2-((5-methyl-2-(4-(methylthio)phenyl)-1H-imidazol-1-yl)methyl)phenoxy)hexanoic acid (Compound 2p)

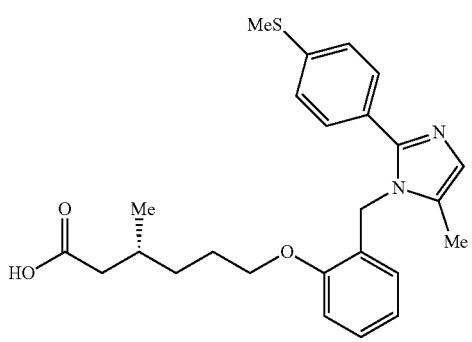 [SMILES: CSc1ccc(-c2ncc(C)n2Cc2ccccc2OCCC[C@@H](C)CC(=O)O)cc1]

The title compound was synthesized from ethyl (R)-3-methyl-6-(2-((5-methyl-2-(4-(methylthio)phenyl)-1H-imidazol-1-yl)methyl)phenoxy)hexanoate (0.310 g, 0.66 mmol) following the experimental procedure described in step-11 of Example-2a.

Yield: 0.075 g (25.7%).

$^1$H NMR (400 MHz, DMSO-d$_6$, 90° C.): δ 7.38 (d, J=8.4 Hz, 2H), 7.26-7.22 (m, 3H), 7.02 (d, J=8.4 Hz, 1H), 6.88-6.84 (m, 2H), 6.42 (d, J=7.6 Hz, 1H), 5.14 (s, 2H), 4.03 (t, J=6.4 Hz, 2H), 2.47 (s, 3H), 2.24-2.18 (m, 1H), 2.06 (s, 3H), 2.04-1.99 (m, 1H), 1.92-1.89 (m, 1H), 1.76-1.70 (m, 2H), 1.49-1.43 (m, 1H), 1.35-1.26 (m, 1H), 0.92 (d, J=6.8 Hz, 3H).

LCMS (ESI+, m/z): 439.0 (M+H)$^+$.

HPLC: 98.5% (210 nm).

Example-2q

Synthesis of 2,2-dimethyl-6-(2-((5-methyl-2-(4-(trifluoromethyl)phenyl)-1H-imidazol-1-yl)methyl)phenoxy)hexanoic acid (Compound 2q)

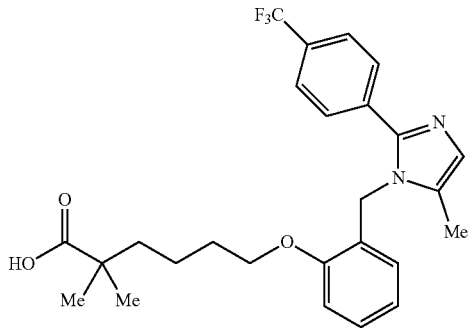 [SMILES: Cc1cnc(-c2ccc(C(F)(F)F)cc2)n1Cc1ccccc1OCCCCC(C)(C)C(=O)O]

Scheme

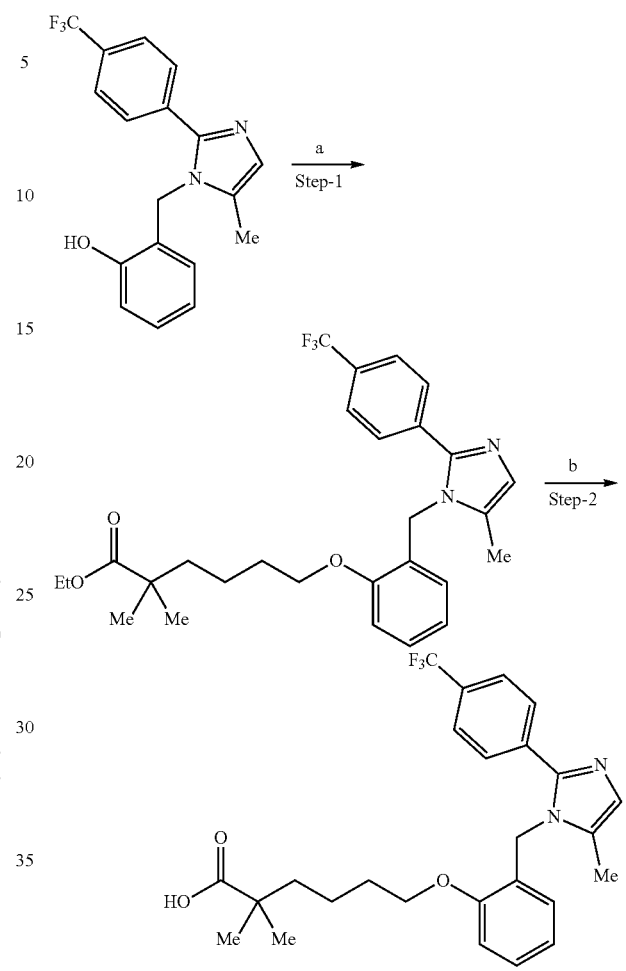

Step-1: Synthesis of ethyl 2,2-dimethyl-6-(2-((5-methyl-2-(4-(trifluoromethyl)phenyl)-1H-imidazol-1-yl)methyl)phenoxy)hexanoate

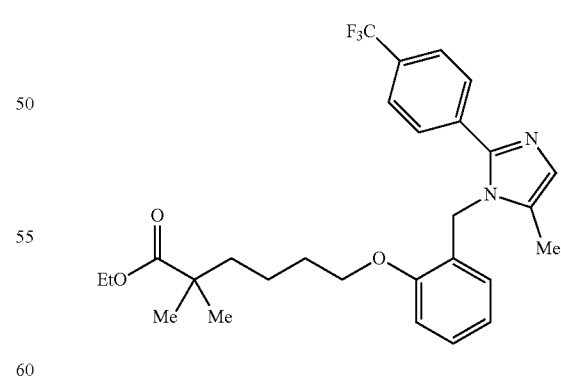

The title compound was synthesized from 2-((5-methyl-2-(4-(trifluoromethyl)phenyl)-1H-imidazol-1-yl)methyl)phenol (0.25 g, 0.75 mmol) and ethyl 6-bromo-2,2-dimethylhexanoate (0.6 g, 2.25 mmol) following the experimental procedure described in step-1 of example-2c.

Yield: 0.121 g.

LCMS (ESI+, m/z): 502.7 (M+H)$^+$.

105

Step-2: Synthesis of 2,2-dimethyl-6-(2-((5-methyl-2-(4-(trifluoromethyl)phenyl)-1H-imidazol-1-yl)methyl)phenoxy)hexanoic acid

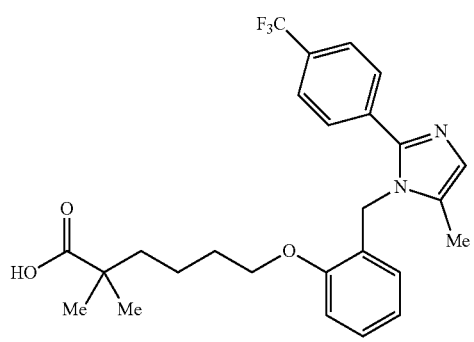 [SMILES: Cc1cnc(-c2ccc(C(F)(F)F)cc2)n1Cc1ccccc1OCCCCC(C)(C)C(=O)O]

The title compound was synthesized from ethyl 2,2-dimethyl-6-(2-((5-methyl-2-(4-(trifluoromethyl)phenyl)-1H-imidazol-1-yl)methyl)phenoxy)hexanoate (0.12 g, 0.24 mmol) following the experimental procedure described in step-11 of Example 2a.

Yield: 0.04 g (35.0%)

$^1$H NMR (400 MHz, DMSO-$d_6$): δ 7.71-7.66 (m, 4H), 7.26-7.22 (m, 1H), 7.02 (d, J=8.0 Hz, 1H), 6.94 (s, 1H), 6.86 (t, J=7.6 Hz, 1H), 6.45 (d, J=7.6 Hz, 1H), 5.20 (s, 2H), 4.03 (t, J=6.4 Hz, 2H), 2.12 (s, 3H), 1.71-1.54 (m, 2H), 1.52-1.49 (m, 2H), 1.41-1.34 (m, 2H), 1.07 (s, 6H).

$^{19}$F NMR (400 MHz, DMSO-$d_6$): δ −61.16

LCMS (ESI+, m/z): 474.8 (M+H)$^+$.

HPLC: 98.49% (210 nm).

Example 2r

Synthesis of (R)-3-methyl-6-(2-((5-(methyl-$d_3$)-2-(4-(trifluoromethyl)phenyl)-1H-imidazol-1-yl)methyl)phenoxy)hexanoic acid (Compound 2r)

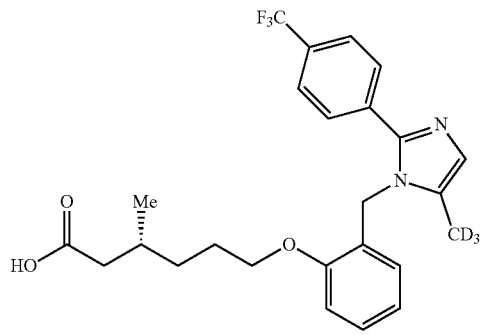 [SMILES: [2H]C([2H])([2H])c1cnc(-c2ccc(C(F)(F)F)cc2)n1Cc1ccccc1OCCC[C@@H](C)CC(=O)O]

Scheme 1

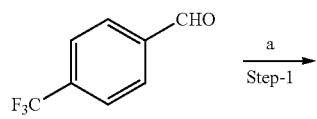

106

-continued

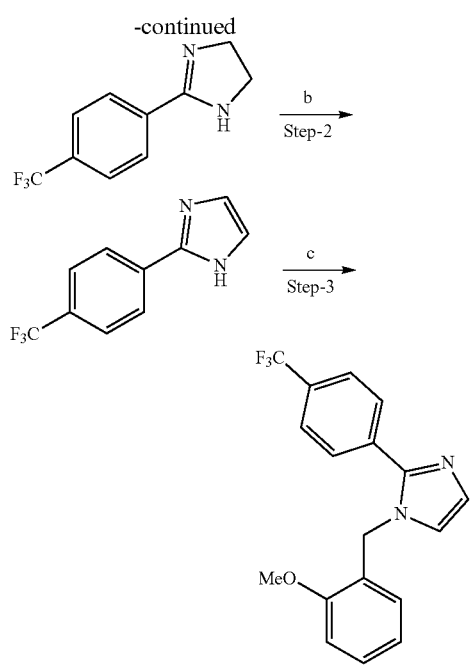

Scheme 2

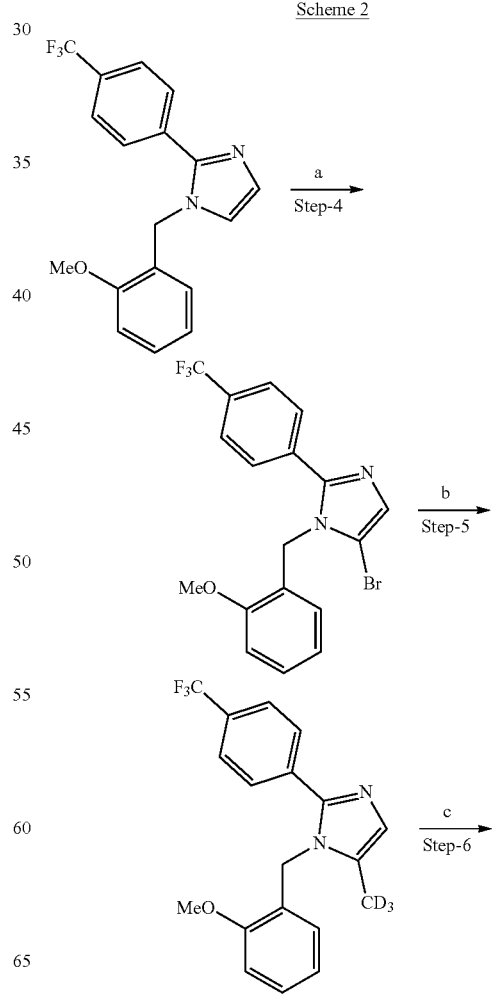

-continued

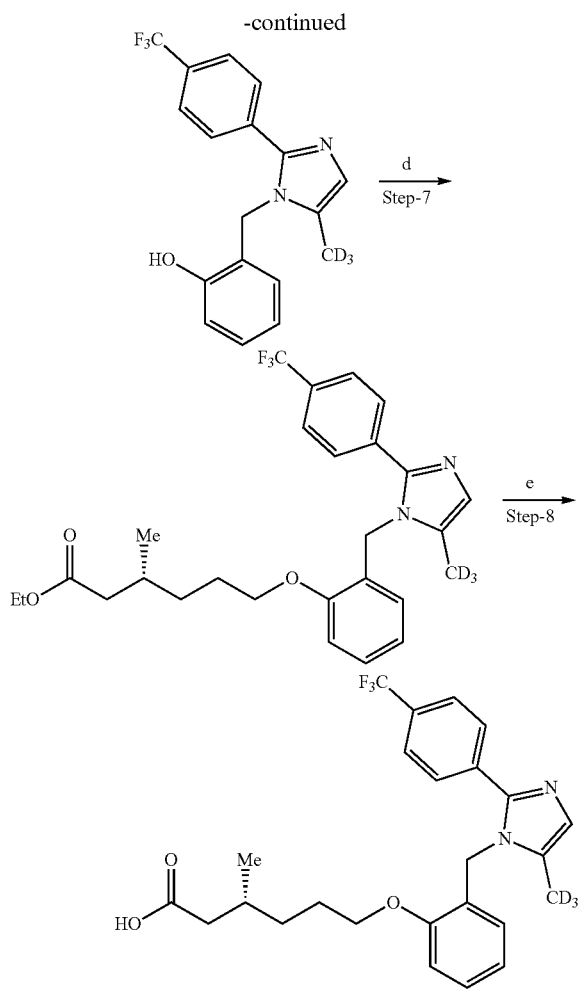

Step-1: Synthesis of 2-(4-(trifluoromethyl)phenyl)-4,5-dihydro-1H-imidazole

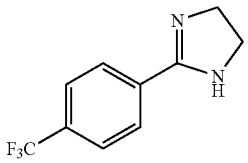

In a 250 mL round bottom flask, a stirred solution 4-(trifluoromethyl)benzaldehyde (5.0 g, 27.17 mmol) and ethane-1,2-diamine (1.80 g, 29.89 mmol) in ᵗBuOH (80 mL) was treated with iodine (8.60 g, 33.96 mmol) and K₂CO₃ (11.30 g, 81.51 mmol) at RT. The reaction mixture was heated at 85° C. for 3 h under nitrogen atmosphere. Upon completion of reaction (TLC), the reaction mixture was quenched with saturated Na₂S₂O₃ solution and extracted with ethyl acetate (100 mL×3). The combined organic extract was washed with brine, dried over anhydrous Na₂SO₄ and concentrated under reduced pressure to get desired product as a yellow solid, which was taken to next step without any purification (5.1 g, 83.1%).

¹H NMR (300 MHz, DMSO-d₆): δ 8.02 (d, J=8.1 Hz, 2H), 7.81 (d, J=8.1 Hz, 2H), 3.64 (s, 4H).

¹⁹F NMR (300 MHz, DMSO-d₆): δ −66.22
LCMS (ESI+, m/z): 215.2 (M+H)⁺.
HPLC (210 nm): 90.59%

Step-2: Synthesis of 2-(4-(trifluoromethyl)phenyl)-1H-imidazole

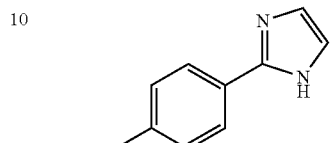

In a 250 mL round bottom flask, a stirred solution 2-(4-(trifluoromethyl)phenyl)-4,5-dihydro-1H-imidazole (5.0 g, 23.36 mmol) in DMSO (80 mL) was treated with K₂CO₃ (3.55 g, 25.7 mmol) and (diacetoxyiodo)benzene (8.30 g, 25.7 mmol) at RT under nitrogen atmosphere. The reaction mixture was stirred at RT for 12 h under nitrogen atmosphere. Upon completion of reaction (TLC), the reaction mixture was diluted with ice cold water and extracted with ethyl acetate (100 mL×3). The combined organic extract was washed with brine, dried over anhydrous Na₂SO₄. and concentrated under reduced pressure. The residue obtained was purified by silica gel column chromatography (elution, 40% EtOAc in hexanes) to afford the title compound as a yellow solid (2.70 g, 54.7%)

¹H NMR (400 MHz, DMSO-d₆): δ 12.81 (brs, 1H), 8.14 (d, J=8.8 Hz, 2H), 7.81 (d, J=8.8 Hz, 2H), 7.23 (s, 2H).

¹⁹F NMR (400 MHz, DMSO-d₆): δ −60.98
LCMS (ESI+, m/z): 213.0 (M+H)⁺.

Step-3: Synthesis of 1-(2-methoxybenzyl)-2-(4-(trifluoromethyl)phenyl)-1H-imidazole

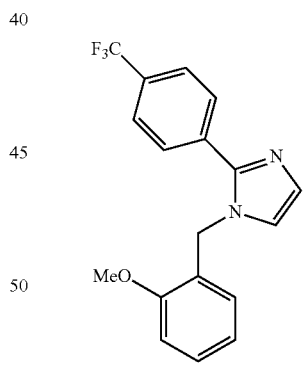

In a 250 mL round bottom flask, a stirred solution 2-(4-(trifluoromethyl)phenyl)-1H-imidazole (6.5 g, 30.66 mmol) in DMF (70 mL) was treated with NaH (60% dispersion, 1.41 g, 36.79 mmol) at 0° C. and stirred for 30 min at same temperature under nitrogen atmosphere. After 30 min, the mixture was treated with 2-methoxybenzyl bromide (7.40 g, 36.79 mmol) and reaction mixture was stirred at RT for 4 h under nitrogen atmosphere. Upon completion of reaction (TLC), the reaction mixture was quenched with saturated NH₄Cl solution and extracted with ethyl acetate (100 mL×3). The combined organic extract was washed with brine, dried over anhydrous Na₂SO₄ and concentrated under reduced pressure. The residue obtained was purified by silica gel column chromatography (elution, 20% EtOAc in hexanes) to afford the title compound as a colorless solid (8 g, 82.5%)

$^1$H NMR (300 MHz, DMSO-d$_6$): δ 7.80 (brs, 4H), 7.30-7.26 (m, 2H), 7.10 (s, 1H), 7.01 (d, J=8.1 Hz, 1H), 6.89 (t, J=6.9 Hz, 1H) 6.75 (dd, J=7.5, 1.8 Hz, 1H), 5.29 (s, 2H), 3.68 (s, 3H).

$^{19}$F NMR (300 MHz, DMSO-d$_6$): δ −61.10

LCMS (ESI+, m/z): 333.2 (M+H)$^+$.

Step-4: Synthesis of 5-bromo-1-(2-methoxybenzyl)-2-(4-(trifluoromethyl)phenyl)-1H-imidazole

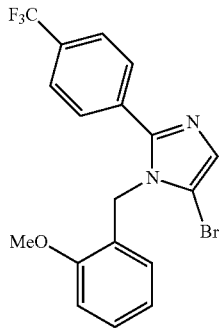 [SMILES: COc1ccccc1Cn1c(Br)cnc1-c1ccc(C(F)(F)F)cc1]

In a 50 mL round bottom flask, a stirred solution of 1-(2-methoxybenzyl)-2-(4-(trifluoromethyl)phenyl)-1H-imidazole (1 g, 3.01 mmol) in DMF (10 mL) was treated with a NBS (0.643 g, 3.61 mmol) at RT under nitrogen atmosphere. The reaction mixture was stirred at 45° C. for 3 h. The reaction mixture was quenched with ice water and extracted with ethyl acetate (30 mL×2). The combined organic extract was washed with brine, dried over anhydrous Na$_2$SO$_4$. and concentrated under reduced pressure. The residue obtained was purified by silica gel column chromatography (gradient elution, 5% EtOAc in hexanes) to afford the title compound as a white solid (0.4 g, 33.4%).

$^1$H NMR (400 MHz, CDCl$_3$): δ 7.59 (s, 4H), 7.33-7.29 (m, 1H), 7.27 (s, 1H), 6.93-6.90 (m, 2H), 6.62 (d, J=8.0 Hz, 1H), 5.24 (s, 2H), 3.85 (s, 3H).

LCMS (ESI+, m/z): 410.5 (M+H)$^+$.

Step-5: Synthesis of 1-(2-methoxybenzyl)-5-(methyl-d$_3$)-2-(4-(trifluoromethyl)phenyl)-1H-imidazole

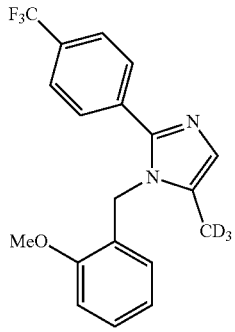 [SMILES: [2H]C([2H])([2H])c1cnc(-c2ccc(C(F)(F)F)cc2)n1Cc1ccccc1OC]

In a 20 mL re-sealable reaction tube, a solution of ZnCl$_2$ (0.5 M in THF, 820 mg, 12.0 mL, 6.0 mmol) in THF (5 mL) was treated with CD$_3$MgI (1 M in diethyl ether, 890 mg, 5.3 ml, 5.0 mmol) dropwise at RT under nitrogen atmosphere. The mixture was stirred at RT for 1 h and treated with 5-bromo-1-(2-methoxybenzyl)-2-(4-(trifluoromethyl)phenyl)-1H-imidazole (100 mg, 0.2 mmol) and Ni(PPh$_3$)$_2$Cl$_2$ (8 mg, 0.01 mmol) at same temperature under nitrogen atmosphere. The resulting reaction mixture was stirred at RT for 48 h under nitrogen atmosphere. Upon completion of reaction (monitored by TLC), the reaction mixture was quenched with ice cold water and extracted with EtOAc (10 mL×2). The combined organic extract was washed with brine, dried over anhydrous Na$_2$SO$_4$. and concentrated under reduced pressure. The residue obtained was purified by silica gel column chromatography (gradient elution, 50% EtOAc in hexanes) to afford the title compound (20 mg) contaminated with debrominated starting material LCMS (ESI+, m/z): 350.1 (M+H)$^+$.

Step-6: Synthesis of 2-((5-(methyl-d$_3$)-2-(4-(trifluoromethyl)phenyl)-1H-imidazol-1-yl)methyl)phenol

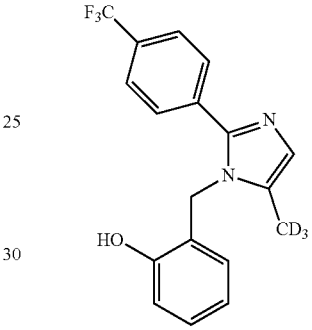

In a 10 mL round bottom flask, a solution of 1-(2-methoxybenzyl)-5-(methyl-d$_3$)-2-(4-(trifluoromethyl)phenyl)-1H-imidazole (20 mg) in DCM (2 mL) was treated with neat BBr$_3$ (0.1 mL) dropwise at −78° C. under nitrogen atmosphere. The reaction mixture was stirred at RT for 3 h. Upon completion of reaction (monitored by TLC), the reaction mixture was basified (pH~9) with aqueous NaHCO$_3$ and solid obtained was filtered and washed with n-hexane (3×5 mL). The solid product was dried under reduced pressure to afford the title compound (12 mg). The crude material was used in next step without further purification.

LCMS (ESI+, m/z): 336.3 (M+H)$^+$.

Step-7: Synthesis of ethyl (R)-3-methyl-6-(2-((5-(methyl-d$_3$)-2-(4-(trifluoromethyl)phenyl)-1H-imidazol-1-yl)methyl)phenoxy)hexanoate

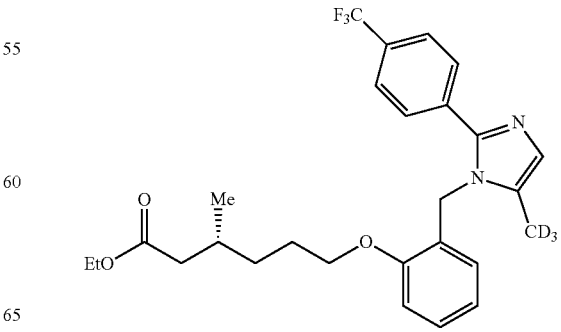

In a 25 mL round bottom flask, a stirred solution of 2-((5-(methyl-d$_3$)-2-(4-(trifluoromethyl)phenyl)-1H-imidazol-1-yl)methyl)phenol (150 mg, 0.44 mmol) in toluene (3 mL) was treated sequentially with DIAD (135 mg, 0.67 mmol) and PPh$_3$ (175 mg, 0.67 mmol) at RT under nitrogen atmosphere. The resulting mixture was stirred at RT for 15 min and treated with ethyl (R)-6-bromo-3-methylhexanoate (93 mg, 0.53 mmol) under nitrogen atmosphere. The reaction mixture was gradually warmed to 65° C. and stirred at same temperature for 12 h. Upon completion of the reaction (monitored by TLC), the reaction mixture was cooled to RT and quenched with ice cold water before extracting with n-hexane (50 mL). The organic extract was washed with brine, dried over anhydrous Na$_2$SO$_4$. and concentrated under reduced pressure. The residue obtained was filtered through by silica gel column (gradient elution, 5-10% EtOAc in hexanes) to afford the title compound (200 mg). The material was used in next step without further purification LCMS (ESI+, m/z): 492.4 (M+H)$^+$.

Step-8: Synthesis of (R)-3-methyl-6-(2-((5-(methyl-d$_3$)-2-(4-(trifluoromethyl)phenyl)-1H-imidazol-1-yl)methyl)phenoxy)hexanoic acid (Compound 2r)

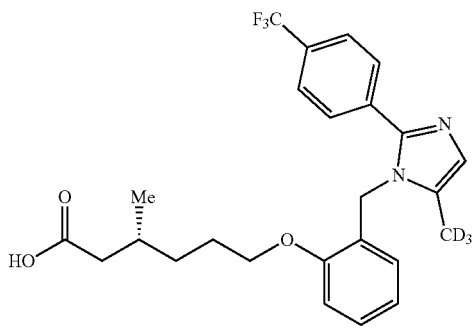 [SMILES: [2H]C([2H])([2H])c1cnc(-c2ccc(C(F)(F)F)cc2)n1Cc1ccccc1OCCC[C@@H](C)CC(=O)O]

In a 500 mL round bottom flask, a stirred solution of ethyl (R)-3-methyl-6-(2-((5-(methyl-d$_3$)-2-(4-(trifluoromethyl)phenyl)-1H-imidazol-1-yl)methyl)phenoxy)hexanoate (1.0 g, 2.03 mmol) in THF (10 mL), MeOH (10 mL) and water (10 mL), was treated with lithium hydroxide monohydrate (853 mg, 20.3 mmol) at RT. The reaction mixture was stirred at RT for 16 h. Upon completion of reaction (monitored by TLC), the reaction mixture was diluted with water and washed with diethyl ether. The aqueous layer was neutralized with 1N HCl and solid obtained was filtered to obtain residue (400 mg). The residue was purified twice using preparative HPLC [Column: WATERS X BRIDGE C18 (150 mm×21.20 mm, 5.00, flow: 15.0 mL/min, mobile phase: A=water, B=MeCN, T/% B=0/30, 3/40, 10/90] to yield the title compound (40 mg).

$^1$H NMR (300 MHz, DMSO-d$_6$): δ 12.00 (br s, 1H), 7.74 (d, J=8.4 Hz, 2H), 7.65 (d, J=8.4 Hz, 2H), 7.28-7.23 (m, 1H), 7.04 (d, J=8.1 Hz, 1H), 6.95 (s, 1H), 6.89-6.84 (m, 1H), 6.40 (d, J=7.5 Hz, 1H), 5.18 (s, 2H), 4.01 (t, J=6.6 Hz, 2H), 2.27-2.16 (m, 1H), 2.03-1.95 (m, 1H), 1.84-1.76 (m, 1H), 1.67-1.65 (m, 2H), 1.45-1.38 (m, 1H), 1.28-1.23 (m, 1H), 0.85 (d, J=6.6 Hz, 3H).

$^{19}$F NMR (300 MHz, DMSO-d$_6$): δ −61.11
$^2$D NMR (600 MHz, CD$_3$OD): δ 2.04
LCMS (ESI+, m/z): 464.4 (M+H)$^+$.
HPLC: 98.21% (210 nm).

Example 2s

Synthesis of (S)-3-methyl-6-(2-((5-methyl-2-(4-(trifluoromethyl)phenyl)-1H-imidazol-1-yl)methyl)phenoxy)hexanoic acid (Compound 2s)

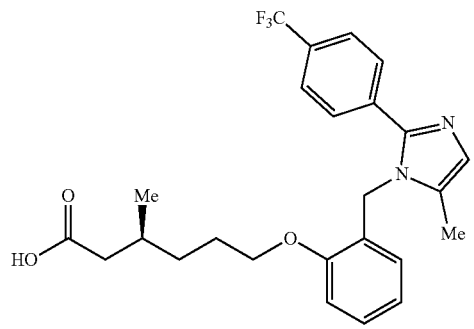

Scheme A

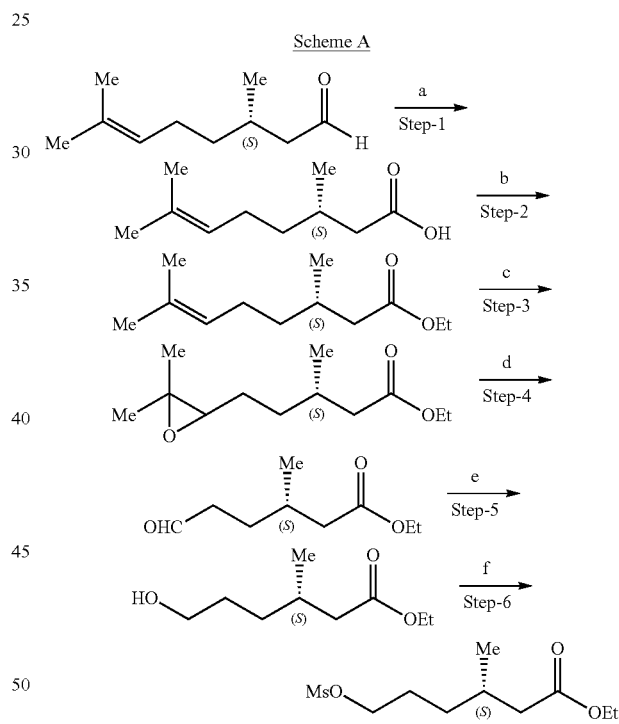

Scheme B

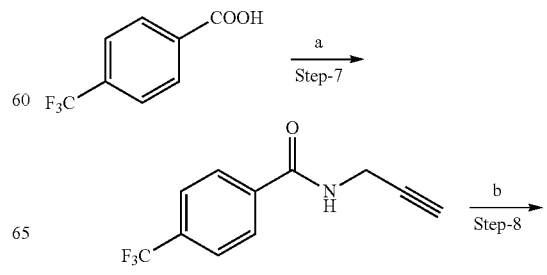

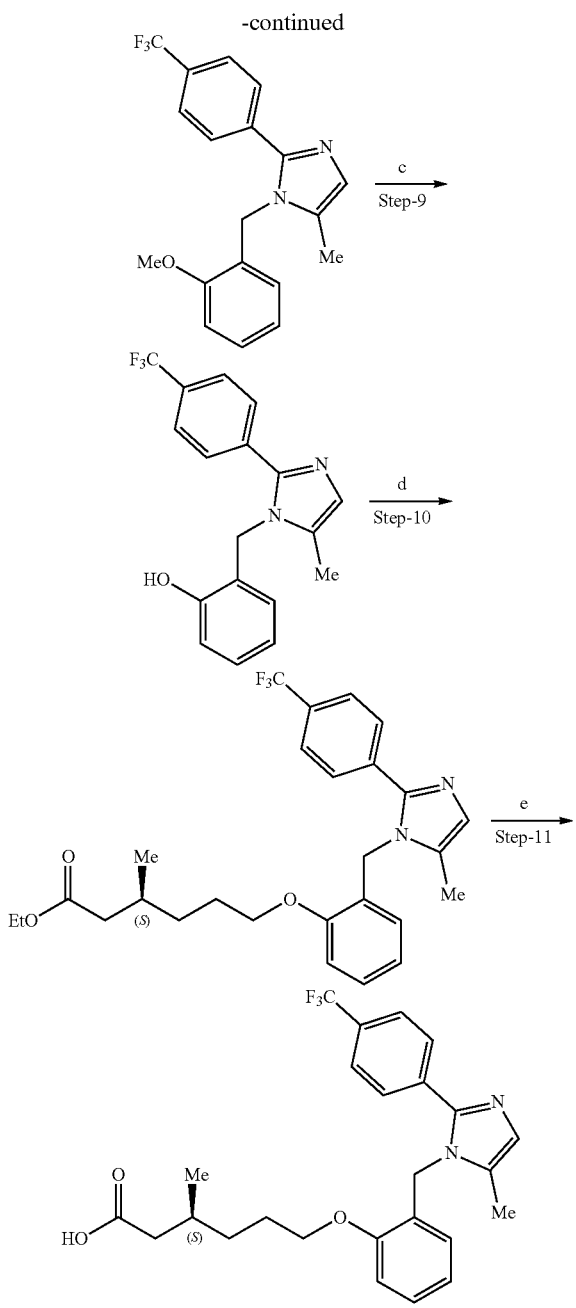

Step-1: Synthesis of (S)-3,7-dimethyloct-6-enoic acid

In a 500 mL of round bottom flask, a solution of NaOH (12.92 g, 325.0 mmol) in water (100 mL) was treated with AgNO$_3$ (25.2 g, 149.0 mmol) in water (100 mL) at 0° C. The reaction mixture was stirred in dark for 30 min and treated (3S)-3,7-dimethyloct-6-enal (10.0 g, 65.0 mmol) at 0° C. The reaction mixture was stirred at RT for 18 h. Upon completion of reaction (monitored by TLC), the reaction mixture was filtered through a Celite® pad and washed with hot water. The combined filtrate was acidified (pH 2) with concentrated HCl and extracted with diethyl ether. The organic extract was dried over anhydrous Na$_2$SO$_4$ and concentrated under reduced pressure. The residue obtained was used in the next step without further purification.

Yield: 10.0 g (90.9%)

$^1$H NMR (400 MHz, CDCl$_3$): δ 8.8 (brs, 1H), 5.09 (t, J=7.2 Hz, 1H), 2.39-2.34 (dd, J=15.0, 6.0 Hz, 1H), 2.17-2.12 (dd, J=15.0, 6.0 Hz, 1H), 2.03-1.94 (m, 3H), 1.67 (s, 3H), 1.59 (s, 3H), 1.36-1.17 (m, 2H), 0.97 (d, J=6.6 Hz, 3H).

Step-2: Synthesis of ethyl (S)-3,7-dimethyloct-6-enoate

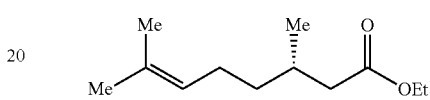

In a 500 mL round bottom flask, a suspension of (S)-3,7-dimethyloct-6-enoic acid (10.0 g, 58.0 mmol) and K$_2$CO$_3$ (20.29 g, 140.0 mmol) in DMF (100 mL) was treated with ethyl bromide (8.25 g, 76.0 mmol) at RT. The reaction mixture was stirred at RT for 16 h. Upon completion of reaction (monitored by TLC), the reaction mixture was diluted with water (1000 mL) and extracted with diethyl ether (100 mL×2). The combined organic extract was dried over anhydrous Na$_2$SO$_4$ and concentrated under reduced pressure to get the title compound (11.3 g, 96.5%).

$^1$H NMR (300 MHz, CDCl$_3$): δ 5.08 (t, J=6.9 Hz, 1H), 4.12 (q, J=7.2 Hz, 2H), 2.29 (dd, J=14.7, 6.0 Hz, 1H), 2.12-2.05 (m, 1H), 1.99-1.94 (m, 3H), 1.67 (s, 3H), 1.59 (s, 3H), 1.39-1.16 (m, 2H), 1.24 (t, J=6.9 Hz, 3H), 0.93 (d, J=6.6 Hz, 3H).

Step-3: Synthesis of ethyl (S)-5-(3,3-dimethyloxiran-2-yl)-3-methylpentanoate

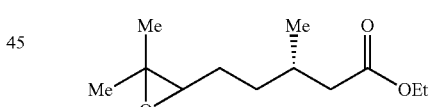

In a 5 L round bottom flask, a solution of ethyl (S)-3,7-dimethyloct-6-enoate (25.0 g, 126.0 mmol) in diethyl ether (200 mL) was treated with a solution of mCPBA (65%, 32.5 g, 189.0 mmol) in diethyl ether (300 mL) dropwise at −30° C. The resulting mixture was warmed to 0° C. and stirred at same temperature for 6 h, before allowing it to stand overnight (~14 h) at 0-3° C. Upon completion of reaction (monitored by TLC), the reaction mixture was diluted with diethyl ether (500 L) and washed with 1N NaOH (2×1 L), followed by water (1 L). The organic layer was washed with brine, dried over anhydrous Na$_2$SO$_4$ and concentrated under reduced pressure to afford the title compound (24.0 g, 88.8%)

$^1$H NMR (400 MHz, CDCl$_3$): δ 4.11 (q, J=7.2 Hz, 2H), 2.69 (t, J=5.4 Hz, 1H), 2.30 (dd, J=8.7, 1.5 Hz, 1H), 2.17-2.09 (m, 1H), 2.04-1.98 (m, 1H), 1.55-1.42 (m, 4H), 1.30 (s, 3H), 1.27 (s, 3H), 1.25 (t, J=7.2 Hz, 3H), 0.96 (d, J=6.6 Hz, 3H).

Step-4: Synthesis of ethyl (S)-3-methyl-6-oxohexanoate

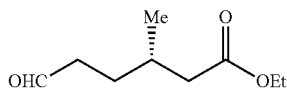

In a 500 mL round bottom flask, a solution of ethyl (S)-5-(3,3-dimethyloxiran-2-yl)-3-methylpentanoate (24.0 g, 11.00 mmol) in 1,4-dioxane (240 L) was treated with a solution of NaIO$_4$ (71.6 g, 33.0 mol) in water (240 mL) at RT. The reaction mixture was stirred at same temperature for 16 h. Upon completion of reaction (monitored by TLC), the inorganic salts were filtered through Celite® pad and filtrate was extracted with EtOAc (3×500 mL). The combined organic extract was washed with water, brine and dried over anhydrous Na$_2$SO$_4$. The solution was concentrated under reduced pressure to afford the title compound (20 g).

$^1$H NMR (300 MHz, CDCl$_3$): δ 9.79 (s, 1H), 4.16-4.07 (m, 2H), 2.48-2.43 (m, 2H), 2.27 (dd, J=15, 6.6 Hz, 1H), 2.17-2.10 (m, 1H), 2.02-1.96 (m, 1H), 1.72-1.66 (m, 1H), 1.54-1.50 (m, 1H), 1.25 (t, J=7.2 Hz, 3H), 0.95 (d, J=6.6 Hz, 3H).

Step 5: Synthesis of ethyl (S)-6-hydroxy-3-methylhexanoate

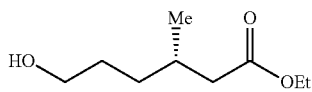

In a 1 L round bottom flask, a solution of ethyl (S)-3-methyl-6-oxohexanoate (20.0 g, 116.0 mmol) in methanol (100 mL) was treated with NaBH$_4$ (7.0 g, 186.0 mmol) at RT. The reaction mixture was stirred at RT for 4 h. Upon completion of reaction (monitored by TLC), the reaction mixture was diluted with water (500 mL) and extracted with EtOAc The combined organic extract was dried over anhydrous Na$_2$SO$_4$ and concentrated under reduced pressure to get the title compound (20.0 g, 99.0%).

$^1$H NMR (300 MHz, CDCl$_3$): δ 4.15-4.07 (m, 2H), 3.65 (t, J=6.3 Hz, 2H), 2.30 (dd, J=14.7, 6.6 Hz, 1H), 2.17-2.09 (m, 1H), 2.02-1.96 (m, 1H), 1.67-1.56 (m, 5H), 1.26 (t, J=7.2 Hz, 3H), 0.93 (d, J=6.6 Hz, 3H).

Step-6: Synthesis of ethyl (S)-3-methyl-6-((methylsulfonyl)oxy)hexanoate

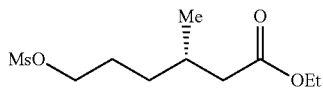

In a 100 mL round bottom flask, a solution of ethyl (S)-6-hydroxy-3-methylhexanoate (2.5 g, 14.3 mmol) in DCM (25 mL) was treated Et$_3$N (4.35 g, 43.0 mmol) and MsCl (2.45 g, 21.5 mmol) at 0° C. The reaction mixture was stirred at RT for 3 h. Upon completion of reaction (monitored by TLC), the reaction mixture was diluted with water (50 mL) and extracted with DCM (50 mL×3). The combined organic extract was dried over anhydrous Na$_2$SO$_4$ and concentrated under reduced pressure to get desired product (2.5 g, 69.5%).

$^1$H NMR (300 MHz, CDCl$_3$): δ 4.23-4.09 (m, 4H), 3.00 (s, 3H), 2.32-2.11 (m, 2H), 2.02-1.96 (m, 1H), 1.78-1.72 (m, 2H), 1.46-1.41 (m, 2H), 1.26 (t, J=7.2 Hz, 3H), 0.96 (d, J=6.6 Hz, 3H).

Step-7: Synthesis of N-(prop-2-yn-1-yl)-4-(trifluoromethyl)benzamide

In a 2 L round bottom flask, a stirred solution of 4-(trifluoromethyl)benzoic acid (100 g, 5.26 mol) and prop-2-yn-1-amine (34.73 g, 6.31 mol) in DMF (1000 mL) was treated sequentially with EDCI.HCl (200.8 g, 1.05 mol), HOBt (142 g, 1.052 mol) and Et$_3$N (53.12 g, 1.578 mol) at RT under nitrogen atmosphere. The reaction mixture was stirred at RT for 12 h under nitrogen atmosphere. Upon completion of reaction (monitored by TLC), the reaction mixture was diluted with ice cold water and solid precipitated out. The solid was filtered and dried under reduced pressure to afford the title compound (111 g, 93.2%).

$^1$H NMR (300 MHz, CDCl$_3$): δ 7.90 (d, J=8.1 Hz, 2H), 7.71 (d, J=8.8 Hz, 2H), 6.47 (brs, 1H), 4.28-4.62 (m, 2H), 3.12 (t, J=2.4 Hz, 1H).

LCMS (ESI+, m/z): 228.2 (M+H)$^+$.

Step-8: Synthesis of 1-(2-methoxybenzyl)-5-methyl-2-(4-(trifluoromethyl)phenyl)-1H-imidazole

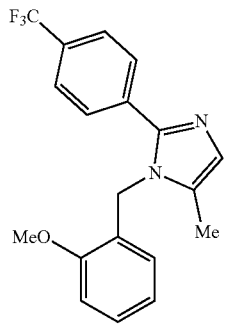

In a 500 mL re-sealable reaction tube, a solution of N-(prop-2-yn-1-yl)-4-(trifluoromethyl)benzamide (30 g, 132.15 mmol) and 2-methoxybenzyl amine (27.31 g, 198.23 mmol) in toluene (300 mL) was treated with Zn(OTf)$_2$ (15.06 g, 39.6 mmol) at RT under nitrogen atmosphere. The reaction mixture was stirred at 100° C. for 16 h. Upon completion of reaction (monitored by TLC), the reaction mixture was diluted with water and extracted with EtOAc (30 mL). The organic extract was washed with saturated NaHCO$_3$, brine and dried over anhydrous Na$_2$SO$_4$. The solution was concentrated under reduced pressure and residue obtained was purified by silica gel column chromatography (elution, 25% EtOAc in hexanes) to yield the title compound (30.4 g, 66.6%).

$^1$H NMR (400 MHz, CDCl$_3$): δ 7.59-7.54 (m, 4H), 7.30-7.23 (m, 1H), 7.00 (s, 1H), 6.91-6.86 (m, 2H), 6.57 (d, J=7.2 Hz, 1H), 5.11 (s, 2H), 3.84 (s, 3H), 2.11 (s, 3H), LCMS (ESI+, m/z): 347.3 (M+H)$^+$.

Step-9: Synthesis of 2-((5-methyl-2-(4-(trifluoromethyl)phenyl)-1H-imidazol-1-yl)methyl)phenol

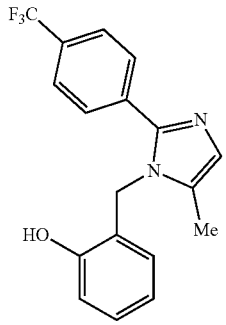 [SMILES: Cc1cnc(-c2ccc(C(F)(F)F)cc2)n1Cc1ccccc1O]

In a 1000 mL round bottom flask, a solution of 1-(2-methoxybenzyl)-5-methyl-2-(4-(trifluoromethyl)phenyl)-1H-imidazole (60 g, 173.4 mmol) in dichloromethane (600 mL) was treated with BBr$_3$ (60 mL) dropwise at −78° C. The reaction mixture was stirred at RT for 3 h. Upon completion of reaction (monitored by TLC), the reaction mixture was basified with aqueous NaHCO$_3$. The solid obtained was filtered, washed with n-hexane (500 mL×3) and dried under reduced pressure to afford the title compound (53.1 g, 92.3%).

$^1$H NMR (400 MHz, DMSO-d$_6$): δ 9.99 (s, 1H), 7.88 (d, J=8.4 Hz, 2H), 7.77 (d, J=8.4 Hz, 2H), 7.33 (s, 1H), 7.14-7.10 (m, 1H), 6.83 (d, J=8.0 Hz, 1H), 6.74-6.70 (m, 1H), 6.55 (d, J=6.8 Hz, 1H), 5.21 (s, 2H), 2.16 (s, 3H).

LCMS (ESI+, m/z): 333.3 (M+H)$^+$.

Step-10: Synthesis of ethyl (S)-3-methyl-6-(2-((5-methyl-2-(4-(trifluoromethyl)phenyl)-1H-imidazol-1-yl)methyl)phenoxy)hexanoate

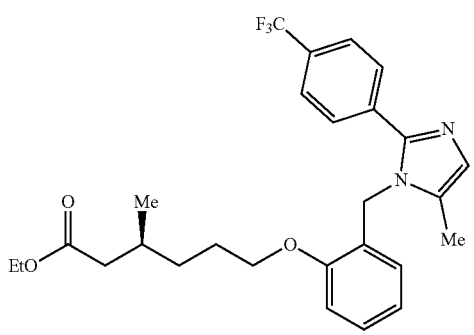 [SMILES: Cc1cnc(-c2ccc(C(F)(F)F)cc2)n1Cc1ccccc1OCCC[C@H](C)CC(=O)O]

In a 100 mL round bottom flask, a stirred solution of 2-((5-methyl-2-(4-(trifluoromethyl)phenyl)-1H-imidazol-1-yl)methyl)phenol (1.0 g, 3.0 mmol) in DMF (15 mL) was treated with K$_2$CO$_3$ (1.24 g, 9.0 mmol) and ethyl (S)-3-methyl-6-((methyl sulfonyl)oxy)hexanoate (1.13 g, 4.5 mmol) at RT under nitrogen atmosphere. The resulting reaction mixture was stirred at 80° C. for 16 h. Upon completion of the reaction (monitored by TLC), the reaction mixture was cooled to RT; solid was filtered and washed with ethyl acetate. The combined filtrate was concentrated under reduced pressure and residue obtained was diluted with cold water (50 mL), before extracting with ethyl acetate (50 mL). The combined organic extract was washed with brine, dried over anhydrous Na$_2$SO$_4$ and concentrated under reduced pressure. The residue obtained was purified by silica gel column chromatography (gradient elution, 15-30% EtOAc in hexanes) to afford the title compound (0.8 g, 57.1%).

$^1$H NMR (300 MHz, CDCl$_3$): δ 7.59 (d, J=1.5 Hz, 4H), 7.33 (s, 1H), 7.02 (d, J=0.9 Hz, 1H), 6.91 (s, 1H), 6.89 (s, 1H), 6.60 (d, J=6.8 Hz, 1H), 5.12 (s, 2H), 4.15-4.01 (m, 4H), 2.19-2.14 (m, 1H), 2.10-1.95 (m, 1H), 2.04 (s, 3H), 1.85-1.76 (m, 2H), 1.55-1.45 (m, 1H), 1.40-1.30 (m, 1H), 1.28-1.18 (m, 4H), 0.83 (d, J=6.4 Hz, 3H).

LCMS (ESI+, m/z): 488.5 (M+H)$^+$.

Step-11: Synthesis of (S)-3-methyl-6-(2-((5-methyl-2-(4-(trifluoromethyl)phenyl)-1H-imidazol-1-yl)methyl)phenoxy)hexanoic acid (Compound 2s)

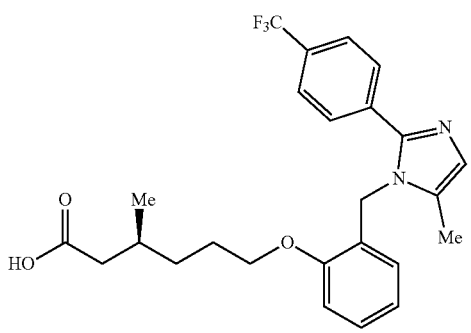

In a 50 mL round bottom flask, a stirred solution of ethyl (S)-3-methyl-6-(2-((5-methyl-2-(4-(trifluoromethyl)phenyl)-1H-imidazol-1-yl)methyl)phenoxy)hexanoate (0.4 g, 0.81 mmol) in THF (40 mL) and water (10 mL), was treated with lithium hydroxide monohydrate (60 mg, 2.4 mmol) at RT. The reaction mixture was stirred at RT for 12 h. Upon completion of reaction (monitored by TLC), the reaction mixture was diluted with water and washed with diethyl ether. The aqueous layer was neutralized with 1N HCl and solid obtained was filtered. The solid compound was washed with 50% diethyl ether-pentane to afford the title compound as a white solid (180 mg, 48.6%).

$^1$H NMR (400 MHz, DMSO-d$_6$): δ 12.00 (br s, 1H), 7.74 (d, J=8.4 Hz, 2H), 7.65 (d, J=8.4 Hz, 2H), 7.26 (t, J=8.4 Hz, 1H), 7.04 (d, J=8.0 Hz, 1H), 6.95 (s, 1H), 6.87 (t, J=7.6 Hz, 1H), 6.40 (d, J=7.6 Hz, 1H), 5.18 (s, 2H), 3.99 (t, J=6.0 Hz, 2H), 2.19-2.14 (m, 1H), 2.10 (s, 3H), 1.99-1.93 (m, 1H), 1.84-1.76 (m, 1H), 1.67-1.65 (m, 2H), 1.45-1.38 (m, 1H), 1.28-1.23 (m, 1H), 0.84 (d, J=6.4 Hz, 3H).

$^{19}$F NMR (400 MHz, DMSO-d$_6$): δ −61.61

LCMS (ESI+, m/z): 460.7 (M+H)$^+$.

HPLC: 98.65% (210 nm).

Example 2t

Synthesis of (S)-3-methyl-6-(2-((5-methyl-2-(6-(trifluoromethyl)pyridin-3-yl)-1H-imidazol-1-yl)methyl)phenoxy)hexanoic acid (Compound 2t)

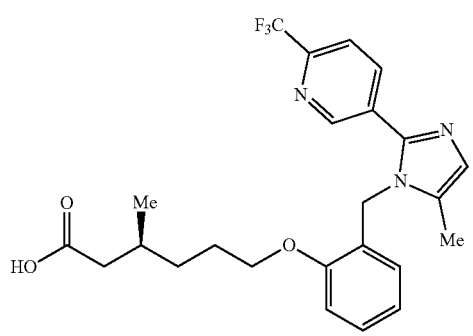

Scheme

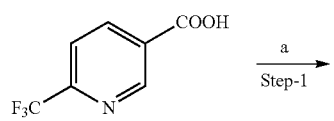

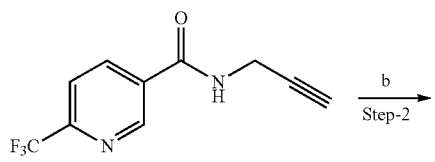

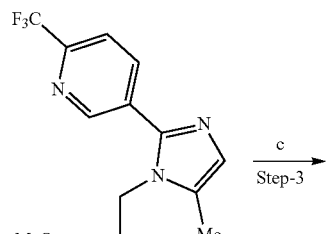

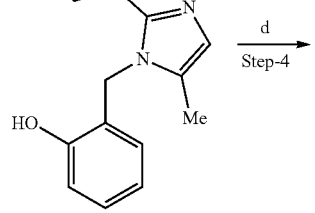

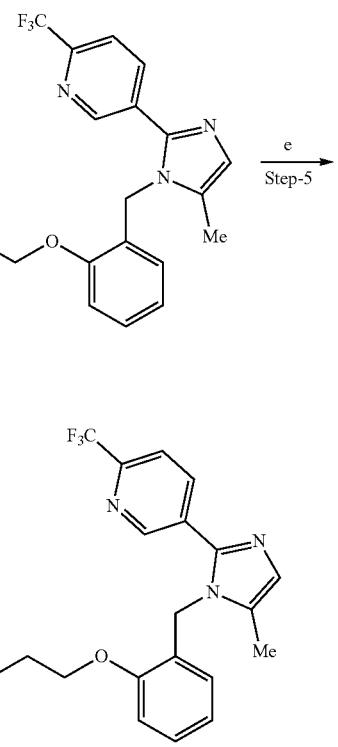

Step-1: Synthesis of N-(prop-2-yn-1-yl)-6-(trifluoromethyl)nicotinamide

In a 3 L round bottom flask, a stirred solution of 6-(trifluoromethyl)nicotinic acid (150 g, 785.34 mmol) and prop-2-yn-1-amine (51.83 g, 942.40 mmol) in DMF (1.5 L) was treated with HATU (447 g, 1177.50 mmol) and Et$_3$N (120 g, 1177.5 mmol) at RT under nitrogen atmosphere. The reaction mixture was stirred at RT for 3 h. Upon completion of reaction (monitored by TLC), the reaction mixture was diluted with ice water and precipitate obtained was filtered, washed with water and 50% ethyl acetate in hexane. The solid compound was dried under reduced pressure to get the title compound (137 g, 76.5%).

$^1$H NMR (400 MHz, DMSO-d$_6$): δ 9.39 (t, J=5.6 Hz, 1H), 9.14 (s, 1H), 8.46 (d, J=8.4 Hz, 1H), 8.05 (d, J=7.6 Hz, 1H), 4.12-4.10 (m, 2H), 3.20 (t, J=0.4 Hz, 1H).
$^{19}$F NMR (400 MHz, DMSO-d$_6$): δ −66.70.
LCMS (ESI+, m/z): 229.2 (M+H)$^+$.

Step-2: Synthesis of 5-(1-(2-methoxybenzyl)-5-methyl-1H-imidazol-2-yl)-2-(trifluoromethyl)pyridine

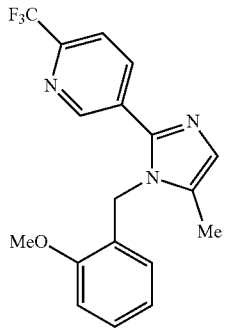 [SMILES: COc1ccccc1Cn1c(C)cnc1-c1ccc(C(F)(F)F)nc1]

In a 500 mL re-sealable reaction tube, a solution of N-(prop-2-yn-1-yl)-6-(trifluoromethyl)nicotinamide (50 g, 219.29 mmol) and 2-methoxybenzyl amine (39.0 g, 285.08 mmol) in toluene (300 mL) was treated with Zn(OTf)$_2$ (23.8 g, 65.78 mmol) at RT under nitrogen atmosphere. The reaction mixture was stirred at 110° C. for 16 h. Upon completion of reaction (monitored by TLC), the reaction mixture was diluted with water and extracted with EtOAc (30 mL). The organic extract was washed with saturated NaHCO$_3$, brine and dried over anhydrous Na$_2$SO$_4$. The solution was concentrated under reduced pressure and residue obtained was purified by washed with diethyl ether to yield the title compound (46 g, 60.65%).

$^1$H NMR (400 MHz, DMSO-d$_6$): δ 8.83 (s, 1H), 8.08 (d, J=8.4 Hz, 1H), 7.94 (d, J=7.6 Hz, 1H), 7.29 (t, J=9.2 Hz, 1H), 7.05 (d, J=7.6 Hz, 1H), 7.01 (s, 1H), 6.88 (t, J=8.4 Hz, 1H), 6.42 (d, J=7.2 Hz, 1H), 5.23 (s, 2H), 3.78 (s, 3H), 2.13 (s, 3H).
$^{19}$F NMR (400 MHz, DMSO-d$_6$): δ −66.43.

Step-3: Synthesis of 2-((5-methyl-2-(6-(trifluoromethyl)pyridin-3-yl)-1H-imidazol-1-yl)methyl)phenol

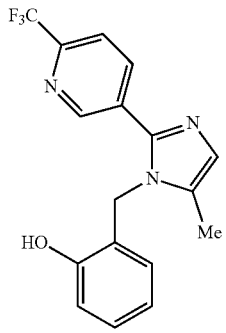 [SMILES: Cc1cnc(-c2ccc(C(F)(F)F)nc2)n1Cc1ccccc1O]

In a 1000 mL round bottom flask, a solution of 5-(1-(2-methoxybenzyl)-5-methyl-1H-imidazol-2-yl)-2-(trifluoromethyl)pyridine (80 g, 230.54 mmol) in dichloromethane (800 mL) was treated with BBr$_3$ (80 mL) dropwise at −78° C. The reaction mixture was stirred at RT for 3 h. Upon completion of reaction (monitored by TLC), the reaction mixture was basified with aqueous NaHCO$_3$. The solid obtained was filtered, washed with n-hexane (500 mL×3) and dried under reduced pressure to afford the title compound (65.0 g, 84.66%).

$^1$H NMR (400 MHz, DMSO-d$_6$): δ 9.94 (s, 1H), 8.83 (s, 1H), 8.12 (d, J=8.0 Hz, 1H), 7.93 (d, J=8.4 Hz, 1H), 7.11 (t, J=8.0 Hz, 1H), 7.01 (s, 1H), 6.86 (d, J=8.0 Hz 1H), 6.72 (d, J=8.8 Hz, 1H), 6.36 (d, J=7.6 Hz, 1H), 5.20 (s, 2H), 2.14 (s, 3H).
$^{19}$F NMR (400 MHz, DMSO-d$_6$): δ −66.44.
LCMS (ESI+, m/z): 334.3 (M+H)$^+$.
HPLC: 99.23% (210 nm).

Step-4: Synthesis of ethyl (S)-3-methyl-6-(2-((5-methyl-2-(6-(trifluoromethyl)pyridin-3-yl)-1H-imidazol-1-yl)methyl)phenoxy)hexanoate

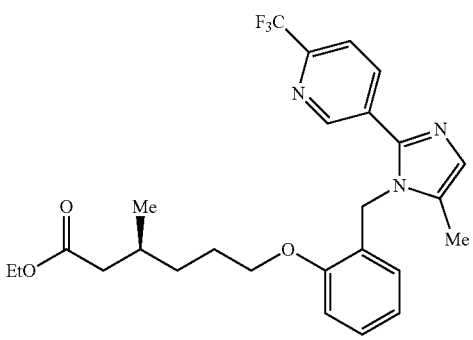 [SMILES: Cc1cnc(-c2ccc(C(F)(F)F)nc2)n1Cc1ccccc1OCCC[C@H](C)CC(=O)O]

In a 100 mL round bottom flask, a stirred solution of 2-((5-methyl-2-(6-(trifluoromethyl)pyridin-3-yl)-1H-imidazol-1-yl)methyl)phenol (1.0 g, 3.0 mmol) in DMF (15 mL) was treated with K$_2$CO$_3$ (1.13 g, 4.5 mmol) and ethyl (S)-3-methyl-6-((methylsulfonyl)oxy)hexanoate (1.24 g, 9.0 mmol) at RT under nitrogen atmosphere. The resulting reaction mixture was stirred at 80° C. for 16 h. Upon completion of the reaction (monitored by TLC), the reaction mixture was cooled to RT; solid was filtered and washed with ethyl acetate. The combined filtrate was concentrated under reduced pressure and residue obtained was diluted with cold water (50 mL), before extracting with ethyl acetate (50 mL). The combined organic extract was washed with brine, dried over anhydrous Na$_2$SO$_4$ and concentrated under reduced pressure. The residue obtained was purified by silica gel column chromatography (gradient elution, 15-30% EtOAc in hexanes) to afford the title compound (0.7 g, crude).
LCMS (ESI+, m/z): 490.2 (M+H)$^+$.

Step-5: Synthesis of (S)-3-methyl-6-(2-((5-methyl-2-(6-(trifluoromethyl)pyridin-3-yl)-1H-imidazol-1-yl)methyl)phenoxy)hexanoic acid (Compound 2t)

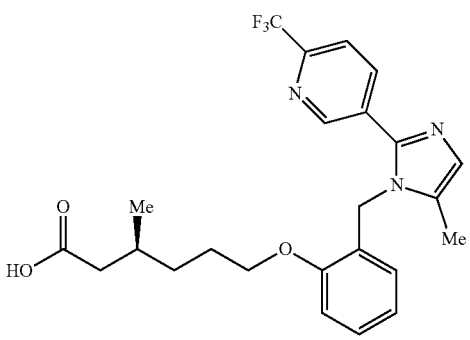

In a 50 mL round bottom flask, a stirred solution of ethyl (S)-3-methyl-6-(2-((5-methyl-2-(6-(trifluoromethyl)pyridin-3-yl)-1H-imidazol-1-yl)methyl)phenoxy)hexanoate (0.4 g, 0.81 mmol) in THF (40 mL) and water (10 mL), was treated with lithium hydroxide monohydrate (60 mg, 2.4 mmol) at RT. The reaction mixture was stirred at RT for 12 h. Upon completion of reaction (monitored by TLC), the reaction mixture was diluted with water and washed with diethyl ether. The aqueous layer was neutralized with 1N HCl and solid obtained was filtered. The solid compound was washed with 50% diethyl ether-pentane to afford the title compound as a white solid (200 mg, 53.0%).

$^1$H NMR (400 MHz, DMSO-d$_6$): δ 12.01 (brs, 1H), 8.81 (s, 1H), 8.06 (d, J=8.4 Hz, 1H), 7.91 (d, J=8.4 Hz, 1H), 7.26 (t, J=7.6 Hz, 1H), 7.05-7.02 (m, 2H), 6.86 (t, J=7.6 Hz, 1H), 6.43 (d, J=6.8 Hz, 1H), 5.22 (s, 2H), 3.99 (t, J=6.4 Hz, 2H), 2.22-2.14 (m, 1H), 2.14 (s, 3H), 2.01-1.86 (m, 1H), 1.86-1.81 (m, 1H), 1.72-1.66 (m, 2H), 1.43-1.37 (m, 1H), 1.28-1.22 (m, 1H), 0.86 (d, J=6.8 Hz, 3H).

$^{19}$F NMR (400 MHz, DMSO-d$_6$): δ −66.77.

LCMS (ESI+, m/z): 463.1 (M+H)$^+$.

HPLC: 97.23% (210 nm).

Example 2u

Synthesis of (R)-3-methyl-6-(2-((5-(methyl-d$_3$)-2-(6-(trifluoromethyl)pyridin-3-yl)-1H-imidazol-1-yl)methyl)phenoxy)hexanoic acid (Compound 2u)

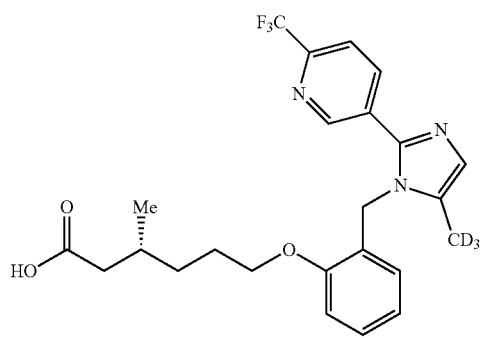 [SMILES: [2H]C([2H])([2H])c1cnc(-c2ccc(C(F)(F)F)nc2)n1Cc1ccccc1OCCC[C@@H](C)CC(=O)O]

Scheme

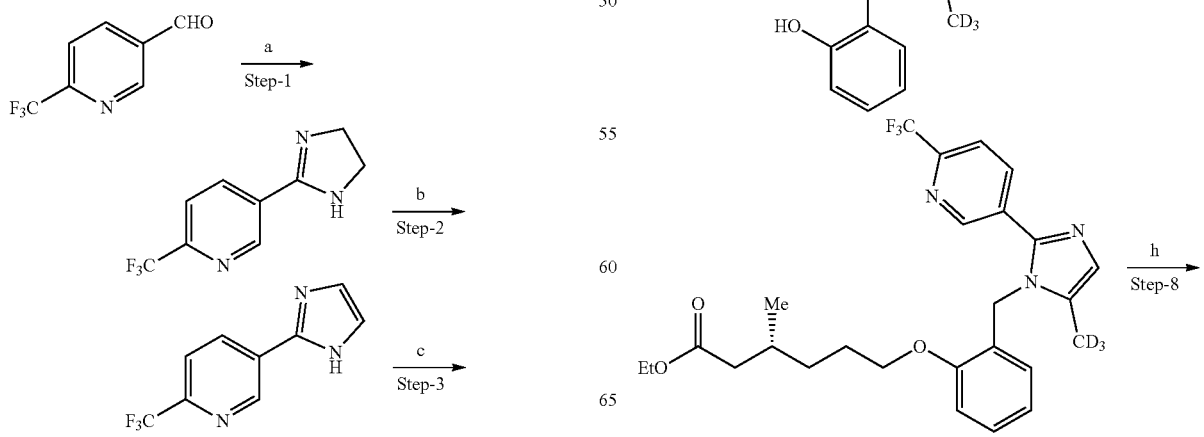

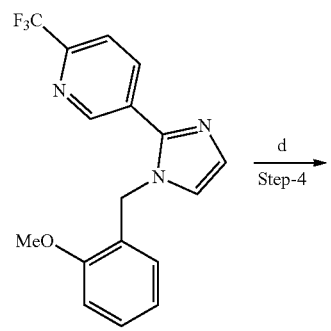

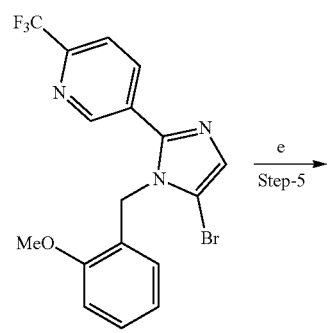

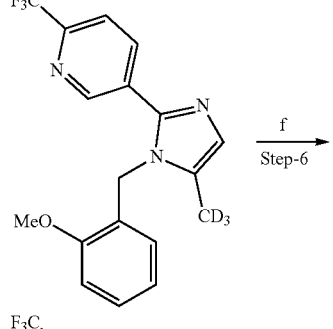

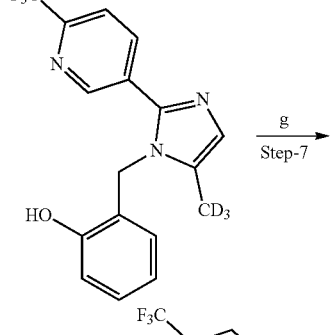

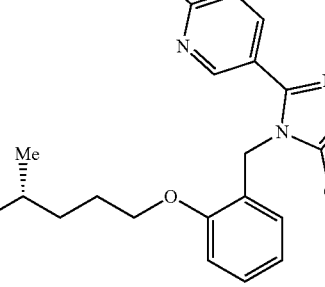

-continued

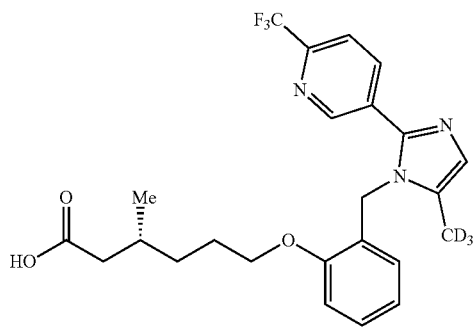

Step-1: Synthesis of 5-(4,5-dihydro-1H-imidazol-2-yl)-2-(trifluoromethyl)pyridine

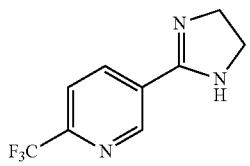

In a 500 mL round bottom flask, a stirred solution 6-(trifluoromethyl)nicotinaldehyde (15.0 g, 85.71 mmol) and ethane-1,2-diamine (5.14 g, 85.71 mmol) in $^t$BuOH (150 mL) was stirred for 45 min at RT under nitrogen atmosphere. Iodine (25.8 g, 102.85 mmol) and $K_2CO_3$ (35.48 g, 257.13 mmol) was added and reaction mixture was heated at 85° C. for 12 h under nitrogen atmosphere. Upon completion of reaction (monitored by TLC), the reaction mixture was quenched with saturated $Na_2S_2O_3$ solution and extracted with ethyl acetate (100 mL×3). The combined organic extract was washed with brine, dried over anhydrous $Na_2SO_4$. and concentrated under reduced pressure to give desired product as a yellow solid, which was taken to next step without any purification (13.1 g, 71.1%).

$^1$H NMR (300 MHz, CDCl$_3$): δ 9.05 (s, 1H), 8.28 (d, J=8.1 Hz, 1H), 7.74 (d, J=8.1 Hz, 1H), 4.10-3.50 (bs, 4H). (note: NH proton not observed in NMR)
$^{19}$F NMR (300 MHz, CDCl$_3$): δ −68.07
LCMS (ESI$^+$, m/z): 216.2 (M+H)$^+$.

Step-2: Synthesis of 5-(1H-imidazol-2-yl)-2-(trifluoromethyl)pyridine

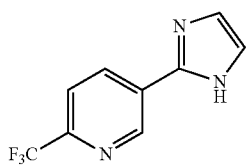 [SMILES: FC(F)(F)c1ccc(-c2ncc[nH]2)cn1]

In a 250 mL round bottom flask, a stirred solution 5-(4,5-dihydro-1H-imidazol-2-yl)-2-(trifluoromethyl)pyridine (6.0 g, 27.9 mmol) in DMSO (50 mL) was treated with $K_2CO_3$ (4.62 g, 33.4 mmol) and (diacetoxyiodo)benzene (10.78 g, 33.4 mmol) at RT. The reaction mixture was stirred at RT for 18 h under nitrogen atmosphere. Upon completion of reaction (monitored by TLC), the reaction mixture was diluted with ice cold water and solid obtained was filtered. The solid was washed with water and n-hexane and dried under reduced pressure to get desired product as a yellow solid (4.0 g, 67.7%).

$^1$H NMR (400 MHz, CDCl$_3$): δ 13.0 (s, 1H), 9.30 (s, 1H), 8.51 (d, J=8.4 Hz, 1H), 7.99 (d, J=8.1 Hz, 1H), 7.43 (s, 1H), 7.16 (s, 1H).
LCMS (ESI$^+$, m/z): 214.2 (M+H)$^+$.

Step-3: Synthesis of 5-(1-(2-methoxybenzyl)-1H-imidazol-2-yl)-2-(trifluoromethyl) pyridine

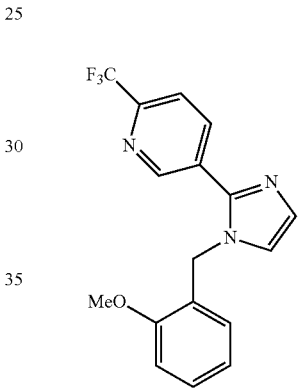

In a 100 mL round bottom flask, a stirred solution 5-(1H-imidazol-2-yl)-2-(trifluoromethyl)pyridine (3 g, 14.0 mmol) in DMF (30 mL) was treated with NaH (60% dispersion in oil, 1.12 g, 28.1 mmol) at 0° C. and stirred for 30 min at same temperature under nitrogen atmosphere. 2-Methoxybenzyl bromide (3.68 g, 18.3 mmol) was added to the above mixture under nitrogen atmosphere. The reaction mixture was stirred for 12 h at RT under nitrogen atmosphere. Upon completion of reaction (monitored by TLC), the reaction mixture was quenched with saturated NH$_4$Cl solution and extracted with ethyl acetate (200 mL×3). The combined organic extract was washed with brine, dried over anhydrous Na$_2$SO$_4$. and concentrated under reduced pressure. The residue obtained was washed with n-hexane to afford the title compound as a white solid (3.5 g, 76.1%)

$^1$H NMR (300 MHz, DMSO-d$_6$): δ 8.96 (s, 1H), 8.25 (d, J=8.4 Hz, 1H), 7.98 (d, J=8.1 Hz 1H), 7.39 (s, 1H), 7.28 (t, J=8.1 Hz, 1H), 7.14 (s, 1H), 6.98 (d, J=8.1 Hz, 1H), 6.88 (t, J=7.2 Hz, 1H), 6.81 (d, J=7.5 Hz, 1H), 5.32 (s, 2H), 3.67 (s, 3H)
$^{19}$F NMR (300 MHz, CDCl$_3$): δ −66.43
LCMS (ESI$^+$, m/z): 334.2 (M+H)$^+$.

Step-4: Synthesis of 5-(5-bromo-1-(2-methoxybenzyl)-1H-imidazol-2-yl)-2-(trifluoromethyl)pyridine

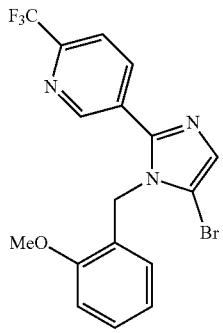 [SMILES: COc1ccccc1Cn1c(Br)cnc1-c1ccc(C(F)(F)F)nc1]

In a 50 mL round bottom flask, a stirred solution of 5-(1-(2-methoxybenzyl)-1H-imidazol-2-yl)-2-(trifluoromethyl)pyridine (3 g, 9.00 mmol) in DMF (30 mL) was treated with a NBS (1.6 g, 9.00 mmol) at RT under nitrogen atmosphere. The reaction mixture was stirred at RT for 3 h. Upon completion of reaction (monitored by TLC), the reaction mixture was quenched with ice water and extracted with ethyl acetate (30 mL×2). The combined organic extract was washed with brine, dried over anhydrous $Na_2SO_4$. and concentrated under reduced pressure. The residue obtained was purified by silica gel column chromatography (elution 5% EtOAc in hexanes) to afford the title compound as a white solid (0.9 g, 24.3%) and mixture (2 g) of 5-(4-bromo-1-(2-methoxybenzyl)-1H-imidazol-2-yl)-2-(trifluoromethyl) pyridine and 5-(4,5-dibromo-1-(2-methoxybenzyl)-1H-imidazol-2-yl)-2-(trifluoromethyl) pyridine.

$^1$H NMR (400 MHz, DMSO-$d_6$): δ 8.87 (s, 1H), 8.15 (d, J=8.4 Hz, 1H), 7.98 (d, J=8.4 Hz 1H), 7.39 (s, 1H), 7.28 (t, J=8.0 Hz, 1H), 7.02 (d, J=8.0 Hz, 1H), 6.87 (t, J=7.2 Hz, 1H), 6.47 (d, J=6.0 Hz, 1H), 5.30 (s, 2H), 3.74 (s, 3H).
$^{19}$F NMR (300 MHz, $CDCl_3$): δ −66.55
LCMS (ESI$^+$, m/z): 412.2, 414.2 (M+H)$^+$.

Step-5: Synthesis of 5-(1-(2-methoxybenzyl)-5-(methyl-$d_3$)-1H-imidazol-2-yl)-2-(trifluoromethyl)pyridine

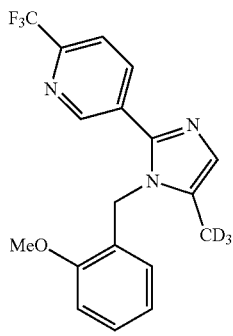 [SMILES: [2H]C([2H])([2H])c1cnc(-c2ccc(C(F)(F)F)nc2)n1Cc1ccccc1OC]

In a 100 mL re-sealable reaction tube, a solution of $ZnCl_2$ (0.5 M in THF, 20.0 mL, 40.0 mmol) was treated with $CD_3MgI$ (1 M in diethyl ether, 12 mL, 12.0 mmol) dropwise at RT under nitrogen atmosphere. The mixture was stirred at RT for 1 h and treated with 5-(5-bromo-1-(2-methoxybenzyl)-1H-imidazol-2-yl)-2-(trifluoromethyl)pyridine (200 mg, 0.486 mmol) and $Ni(PPh_3)_2Cl_2$ (26 mg, 0.0486 mmol) at same temperature under nitrogen atmosphere. The resulting reaction mixture was stirred at RT for 48 h under nitrogen atmosphere. Upon completion of reaction (monitored by TLC), the reaction mixture was quenched with ice cold water and extracted with EtOAc (10 mL×2). The combined organic extract was washed with brine, dried over anhydrous $Na_2SO_4$. and concentrated under reduced pressure. The residue obtained was purified by silica gel column chromatography (elution 50% EtOAc in hexanes) to afford the title compound (50 mg) contaminated with debrominated side product, 5-(1-(2-methoxybenzyl)-1H-imidazol-2-yl)-2-(trifluoromethyl) pyridine (as indicated by NMR (~1:1))
LCMS (ESI$^+$, m/z): 351.1 (M+H)$^+$.

Step-6: Synthesis of 2-((5-(methyl-$d_3$)-2-(6-(trifluoromethyl) pyridin-3-yl)-1H-imidazol-1-yl) methyl) phenol

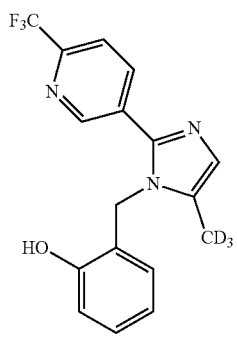 [SMILES: [2H]C([2H])([2H])c1cnc(-c2ccc(C(F)(F)F)nc2)n1Cc1ccccc1O]

In a 100 mL round bottom flask, a solution of 5-(1-(2-methoxybenzyl)-5-(methyl-$d_3$)-1H-imidazol-2-yl)-2-(trifluoromethyl)pyridine (200 mg, 0.571 mmol) in DCM (5 mL) was treated with neat $BBr_3$ (0.2 mL) dropwise at −78° C. under nitrogen atmosphere. The reaction mixture was gradually warmed to RT and stirred at RT for 3 h. Upon completion of reaction (monitored by TLC), the reaction mixture was basified (pH~9) with aqueous $NaHCO_3$ and solid obtained was filtered and washed with n-hexane (3×5 mL). The solid product was dried under reduced pressure to afford the title compound (180 mg), which was used in next step without further purification.
LCMS (ESI$^+$, m/z): 337.1 (M+H)$^+$.

Step-7: Synthesis of ethyl (R)-3-methyl-6-(2-((5-(methyl-$d_3$)-2-(6-(trifluoromethyl) pyridin-3-yl)-1H-imidazol-1-yl) methyl)phenoxy)hexanoate

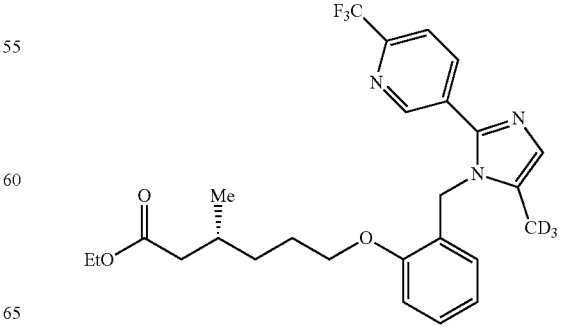

In a 50 mL round bottom flask, a stirred solution of 2-((5-(methyl-d₃)-2-(6-(trifluoromethyl)pyridin-3-yl)-1H-imidazol-1-yl)methyl)phenol (180 mg, 0.365 mmol) in DMF (5 mL) was treated with K$_2$CO$_3$ (151 mg, 1.09 mmol) and ethyl (R)-3-methyl-6-((methylsulfonyl)oxy)hexanoate (138 mg, 0.548 mmol) at RT under nitrogen atmosphere. The resulting reaction mixture was stirred at 80° C. for 16 h under nitrogen atmosphere. Upon completion of reaction (monitored by TLC), the reaction mixture was diluted with water (50 mL) and extracted with ethyl acetate (3×20 mL). The combined organic extract was washed with brine and dried over anhydrous Na$_2$SO$_4$. The solution was concentrated under reduced pressure. The residue obtained was flash purified by silica gel column chromatography (gradient elution, 15-30% EtOAc in hexanes) to afford the title compound (258 mg), contaminated with side product, ethyl (R)-3-methyl-6-(2-((2-(6-(trifluoromethyl)pyridin-3-yl)-1H-imidazol-1-yl)methyl)phenoxy)hexanoate.

LCMS (ESI⁺, m/z): 493.6 (M+H)⁺.

Step-8: Synthesis of (R)-3-methyl-6-(2-((5-(methyl-d₃)-2-(6-(trifluoromethyl) pyridin-3-yl)-1H-imidazol-1-yl)methyl)phenoxy)hexanoic acid (Compound 2u)

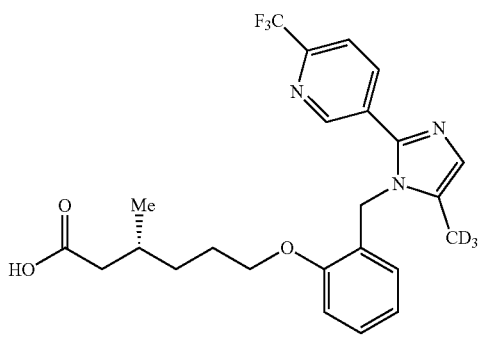 [SMILES: [2H]C([2H])([2H])c1cnc(-c2ccc(C(F)(F)F)nc2)n1Cc1ccccc1OCCC[C@@H](C)CC(=O)O]

In a 50 mL round bottom flask, a stirred solution of ethyl (R)-3-methyl-6-(2-((5-(methyl-d₃)-2-(6-(trifluoromethyl) pyridin-3-yl)-1H-imidazol-1-yl)methyl)phenoxy) hexanoate (250 mg, 0.508 mmol) in THF (5 mL), EtOH (1 mL) and water (5 mL), was treated with lithium hydroxide monohydrate (213 mg, 5.08 mmol) at RT. The reaction mixture was stirred at RT for 16 h. Upon completion of reaction (monitored by TLC), the reaction mixture was diluted with water and washed with diethyl ether. The aqueous layer was neutralized with 1N HCl and solid obtained was filtered. The solid residue obtained was further purified by preparative HPLC [Kinetex C18, (21.2 mm×150 mm) 5.0µ; Flow: 15.0 mL/min; mobile phase: A=: 0.1% TFA, B=MeCN, T/% B=0/25, 2/35, 8/65]. The HPLC fractions were concentrated under reduced pressure and residue obtained was diluted with water, before extracting with ethyl acetate (2×15 mL). The organic extract was washed with brine, dried over anhydrous Na$_2$SO$_4$ and concentrated under reduced pressure to afford the title compound (30.5 mg, 12.9%).

$^1$H NMR (400 MHz, DMSO-d$_6$): δ 12.00 (br s, 1H), 8.81 (s, 1H), 8.07 (d, J=7.2 Hz, 1H), 7.92 (d, J=8.4 Hz 1H), 7.26 (t, J=7.2 Hz, 1H), 7.04 (d, J=7.2 Hz, 1H), 7.03 (s, 1H), 6.86 (t, J=7.6 Hz, 1H), 6.46 (d, J=7.2 Hz, 1H), 5.23 (s, 2H), 3.99 (t, J=6.0 Hz, 2H), 2.28-2.17 (m, 1H), 2.02-1.96 (m, 1H), 1.84-1.76 (m, 1H), 1.70-1.65 (m, 2H), 1.45-1.38 (m, 1H), 1.28-1.22 (m, 1H), 0.86 (d, J=6.8 Hz, 3H).

$^{19}$F NMR (400 MHz, DMSO-d$_6$): δ −66.45
$^2$D NMR (600 MHz, CH$_3$OH): δ 2.10 (s, 3D)
LCMS (ESI⁺, m/z): 465.2 (M+H)⁺.
HPLC: 95.27% (210 nm).

Example 3

Improving Mitochondrial Biogenesis and Function in Duchenne Muscular Dystrophy (DMD) Muscle Cells Rationale: Mitochondrial defects are observed in model systems of Duchenne Muscular Dystrophy including, but not limited to, fatty acid metabolism and biogenesis. See Rybalka, E., et al., *Defects in mitochondrial ATP synthesis in dystrophin-deficient mdx skeletal muscles may be caused by complex I insufficiency*. PLoS One, 2014. 9(12): p. e115763. In this example, myoblast cells from a commercially available Duchenne Muscular Dystrophy patient were treated with Compound 2d and tested for improvements in fatty acid oxidation and mitochondrial biogenesis.

Cell culture and treatment: DMD human skeletal muscle cells were plated into Seahorse XF plates (Agilent Technologies) and allowed to differentiate for 7 days. Differentiated cells were treated with vehicle or compound 2d for 24 hours prior to assay in DMEM media without Pyruvate, Glucose, Glutamine supplemented with galactose and 500 µM carnitine.

Fatty acid oxidation assay: Mitochondria stress test components were loaded in Krebs-Henseleit Buffer at final concentrations 2.5 µM Oligomycin A (Sigma 75351); 7 µM FCCP (Sigma C2920); 1 µM both Rotenone (Sigma R8875) and Antimycin A (Sigma A8674). Following calibration, 200 µL KHB mixed with control BSA (final 0.037 mM; from) or BSA-palmitate (final 0.037 mM BSA 500 µM palmitate) was added to the appropriate wells. Next the cell culture plate was placed into the Seahorse XFe96 Analyzer (Agilent Technologies) and the assay was initiated.

The data was analyzed as follows: The non-mitochondrial respiration (Rot/AA) was subtracted from all oxygen consumption rate (OCR) values. Values of the individual well measurements for all three FCCP OCR from BSA/PAL were divided by the average of the wells for each FCCP OCR value from BSA. This ratio served as the amount of respiration that was the result of palmitate oxidation. These numbers were then normalized to the vehicle average FCCP OCR value to generate the reported fold change in palmitate oxidation.

Mitochondrial biogenesis: DMD human skeletal muscle cells were plated into 96 well plates. Media was changed to Differentiation Medium and cells were allowed to differentiate for 7 days. On Day 4 of differentiation, cells were either treated with vehicle, compound 2d, or infected with PGC-1α adenovirus or LacZ adenovirus at a modality of infection of 200. Three days later cells were labeled with bromodeoxyuridine (BrdU) in culture media for 2 hours. Following the incubation, cells were washed, and then incubated with anti-BrdU antibody overnight at 4° C. The next day, samples were washed incubated with anti-mouse IgG HRP for 45 min at 37° C., and then washed. Optical density was measured at 450 nM wavelength on a SpectraMax M5 (Molecular Devices).

Statistical Analysis: Data was analyzed in Graph Pad Prism. Normality of distribution was determined by D'Agostino-Pearson omnibus normality test. If the samples were normally distributed, they were analyzed by One-Way ANOVA followed by a post hoc Dunnett's test vs DMSO control cells or unpaired two tailed T-test. If the samples were not normally distributed, then a Kruskal-Wallis test was used to determine significance. Results of statistical testing is demonstrated as follows: *p<0.05, p<0.01, *p<0.001, ****p<0.0001.

Results: Palmitate oxidation increased in a dose-dependent manner with compound 2d (FIG. 1).

Figure 2:
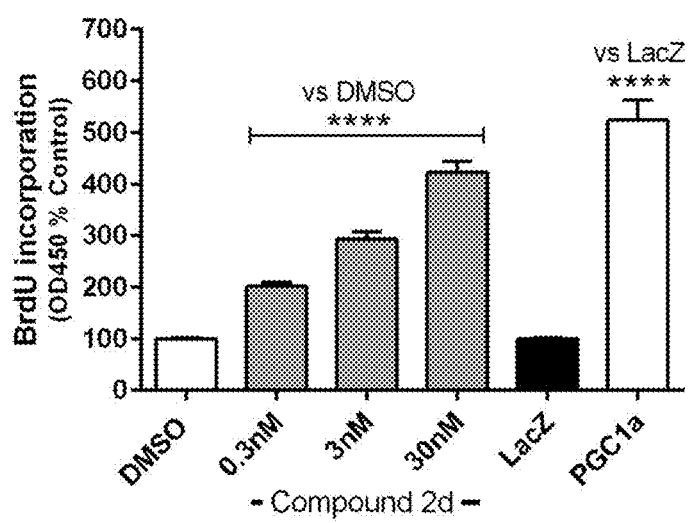
FIG. 2 is a graph showing mitochondrial biogenesis increases with Compound 2d treatment in DMD patient cells.

Mitochondrial biogenesis increased in a dose-dependent manner with Compound 2d treatment (FIG. 2). Overexpression of the transcription factor PGC1a served as a positive control for the assay.

Example 4

Increasing Capacity for Endurance Exercise in Mouse Model of Duchenne Muscular Dystrophy Rationale: PPARδ is activated in response to exercise where it will elicit an increase in fatty acid utilization. Duchenne Muscular Dystrophy is a progressive, early-onset degenerative muscle disease with associated muscle function deficits resulting from the loss of the protein dystrophin. Fatty acid metabolism and altered mitochondrial function are reported to be an aspect of the disease. In this demonstration, the mdx mouse model of Duchenne Muscular Dystrophy was treated daily for 5 weeks with oral-administration of Compound 2d and tested for endurance exercise capacity by treadmill.

Animals and dosing: C57BL/10ScSn-Dmdmdx/J and C57BL/10ScSnJ mice ~5-7 weeks of age were received and housed singly in polycarbonate cages. Animals were fed standard chow and had access to feed and water at all times ad libitum. Compound 2d was formulated fresh each day for this protocol in the vehicle, 5% Ethanol+5% Solutol in purified water and tested at 10 or 30 mg per kg (mpk). Vehicle was dosed for control groups. All the animals were dosed by oral gavage (PO) for 34-35 days. The mice were dosed at 8 AM on the last in-life study day with the necropsy started 2 hours after the final dose.

Endurance running assay: Mice were acclimated to a moving belt treadmill in a series of acclimation runs before evaluation for overall endurance at a set maximal speed. Each mouse was run in a separate lane that contained an electric stimulating grid. The number of visits to the electric stimulating grid and the number of shocks each animal received were recorded by the instrument and a technician evaluated the animal during the run to determine the time and distance to exhaustion. The maximum speed for all the three endurance runs was capped at 20 m/min. The mice were considered exhausted if they stayed on the stimulation grid with no limbs on the treadmill belt for more than 10 consecutive seconds.

Statistical analysis: Values were tested for normality in all groups via a D'Agostino-Pearson omnibus normality test and a Shapiro-Wilk normality test and tested by Kruskal-Wallis 1-Way ANOVA (non-parametric) followed by post hoc Dunn's multiple comparison testing versus the mdx vehicle group. Results of statistical testing is demonstrated as follows: *p<0.05, p<0.01, *p<0.001, ****p<0.0001.

Figure 3:
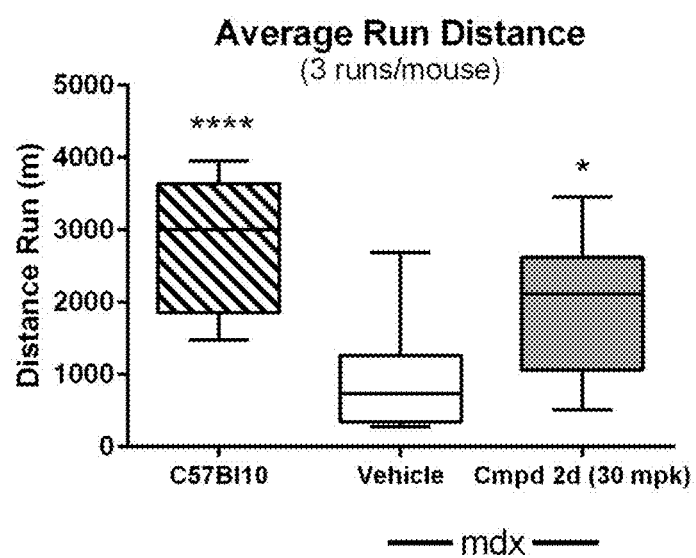
FIG. 3 is a graph showing treadmill running distance of DMD model mouse (mdx) increases with Compound 2d.

Results: Dystrophic mdx mice consistently were outperformed by C57BL10 mice in all three endurance runs. Compound 2d treated mdx mice consistently demonstrated increased distance over mdx vehicle treated group mice both in terms of total distance per run and when evaluating average performance of the three runs (FIG. 3).

Example 5

Reducing Dystrophic Muscle Phenotype in Mouse Model of Duchenne Muscular Dystrophy Rationale: Similar to the muscle pathology in Duchenne Muscular Dystrophy, mdx mice have dystrophic pathologies in skeletal muscle that is apparent soon after birth. Key aspects of this phenotype evident by pathology are the loss of myofibers through apoptosis/necrosis, evidence of regenerating muscle fibers, infiltrating immune cells, and increased muscle fibrosis. In this demonstration, mdx mice were administered Compound 2d orally and assessed for muscle pathology.

Animals and dosing: Animals and dosing were as previously described. See Example 4.

Histology Pathology Assessment: Quadriceps, gastrocnemius and tibialis anterior muscles were harvested at necropsy, and fixed by immersion in 10% neutral buffered formalin and embedded in paraffin. Tissues were sectioned at 5 μm from each block and slides were evaluated by a board certified veterinary pathologist. Histopathologic evaluation included qualitative and semi-quantitative evaluation for myofiber necrosis, inflammation, myofiber regeneration and interstitial fibrosis, as outlined in Tables 1, 2, and 3, respectively.

TABLE 1

Scoring criteria for myofiber necrosis/active regeneration

| Score | Description |
|---|---|
| 0 | None |
| 0.5 | Scant: scattered individual or very small clusters of myofiber necrosis/regeneration, involving <3% of the section |
| 1 | Minimal: scattered individual or small clusters of myofiber necrosis/regeneration, involving 3-10% of the section |
| 2 | Mild: more noticeable, multifocal clusters of myofiber necrosis/regeneration, involving 11-30% of the section |
| 3 | Moderate: larger, coalescing foci of myofiber necrosis/regeneration, involving 31-50% of the section |
| 4 | Marked: extensive foci of myofiber necrosis/regeneration, involving 51-70% of the section |
| 5 | Severe: diffuse myofiber necrosis/regeneration, involving >70% of the section |

TABLE 2

Scoring criteria for inflammation

| Score | Description |
|---|---|
| 0 | None |
| 0.5 | Scant: scattered inflammatory infiltrates, involving <3% of the section |
| 1 | Minimal: scattered inflammatory infiltrates, involving 3-10% of the section |
| 2 | Mild: more noticeable, multifocal clusters of inflammatory infiltrates, involving 11-30% of the section |
| 3 | Moderate: larger, coalescing foci of inflammatory infiltrates, involving 31-50% of the section |
| 4 | Marked: extensive inflammatory cell infiltration, involving 51-70% of the section |
| 5 | Severe: diffuse inflammatory cell infiltration, involving >70% of the section |

TABLE 3

Scoring criteria for interstitial fibrosis

| Score | Description |
|---|---|
| 0 | None |
| 0.5 | Scant: scattered interstitial fibrosis, involving <3% of the section |
| 1 | Minimal: scattered interstitial fibrosis, involving 3-10% of the section |
| 2 | Mild: more noticeable, multifocal areas of interstitial fibrosis, involving 11-30% of the section |
| 3 | Moderate: larger, coalescing foci of interstitial fibrosis, involving 31-50% of the section |
| 4 | Marked: extensive interstitial fibrosis, involving 51-70% of the section |
| 5 | Severe: diffuse interstitial fibrosis, involving >70% of the section |

Immunofluorescent Assessment of Muscle Necrosis: Pre-cut paraffin section slides were deparaffinized and incubated with AlexaFluor 488 conjugated wheat germ agglutinin followed by an incubation with Alexa 568 conjugated anti-mouse IgM (abcam, Product #ab175702). Slides were washed and mounted with coverslips using ProLong Diamond Antifade Mountant with DAPI. Imaging was performed on a Nikon fluorescent microscope using a 40× objective and composite images were stitched together using NIS Elements Software, V4.4 (Nikon, Tokyo, Japan). Analysis was completed using Image J 1.50b, Java 1.8.0_60 (64 bit).

Diaphragm Fibrosis: Diaphragm samples were harvested carefully and the central tendon was cut away to ensure hydroxyproline signal was derived from muscle and not collagen-rich tendon. Hydroxyproline assay was performed according to the manufacturers' instructions (Sigma-Aldrich Hydroxyproline Assay Kit). Final values were calculated as follows:

$$\frac{ug \text{ hydroxyproline}}{mg \text{ wet muscle } wt} = \frac{\left(ug \text{ HPL determined by standard curve} \times \frac{uL \text{ acid muscle was dissolved in}}{uL \text{ supernatant assayed}}\right)}{mg \text{ of dissected muscle}}$$

Statistical analysis: Diaphragm weights, histology scores and immunofluorescence data were tested using a parametric test if normality was confirmed by Shapiro-Wilk normality test (unpaired t-test for 2 groups or One way ANOVA followed by post hoc Dunn's multiple comparison testing versus the mdx vehicle group for 3 groups) and a Mann-Whitney test (2 groups) or Kruskal-Wallis One-Way ANOVA (non-parametric) followed by post hoc Dunn's multiple comparison testing versus the mdx vehicle group (3 groups) if the data were not normally distributed. Results of statistical testing is demonstrated as follows: $*p<0.05$, $p<0.01$, $*p<0.001$, $****p<0.0001$.

Figure 4:
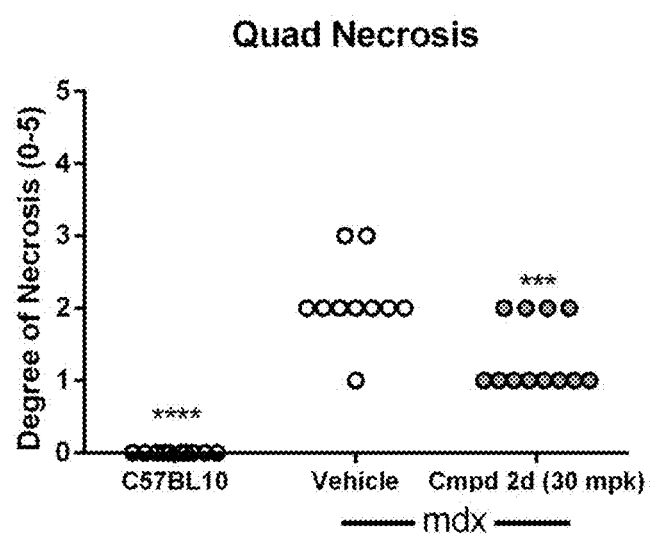
FIG. 4 is a plot showing pathology scored necrosis is reduced in mdx quadriceps with Compound 2d treatment.

Results: Total muscle damage was measured through qualitative histological examination and quantitatively by immunofluorescent labeling. Decreased necrosis was observed in the quadriceps muscle of Compound 2d treated mdx mice (FIG. 4).

Figure 5:
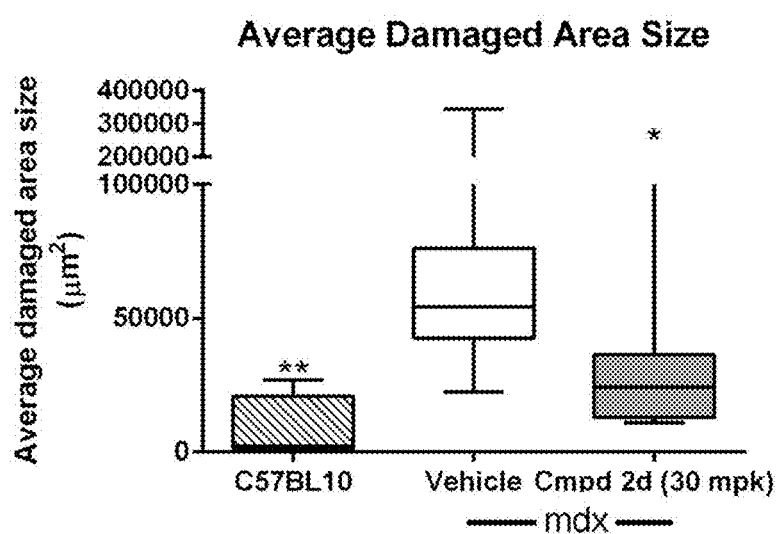
FIG. 5 is a graph showing necrotic region size is decreased with Compound 2d administration in mdx mice.

Quadriceps muscle sections were labeled fluorescently to detect IgM antibody accumulation within damaged myofibers, an indication of loss of myofiber integrity and active necrosis. Each muscle section was imaged in its entirety and the number and size of necrotic regions was measured. Imaging was performed on a Nikon fluorescent microscope using a 40× objective and composite images were stitched together using NIS Elements Software, V4.4 (Nikon, Tokyo, Japan). Analysis was completed using Image J 1.50b, Java 1.8.0_60 (64 bit). The average size of the necrotic regions was significantly reduced (FIG. 5).

Figure 6:
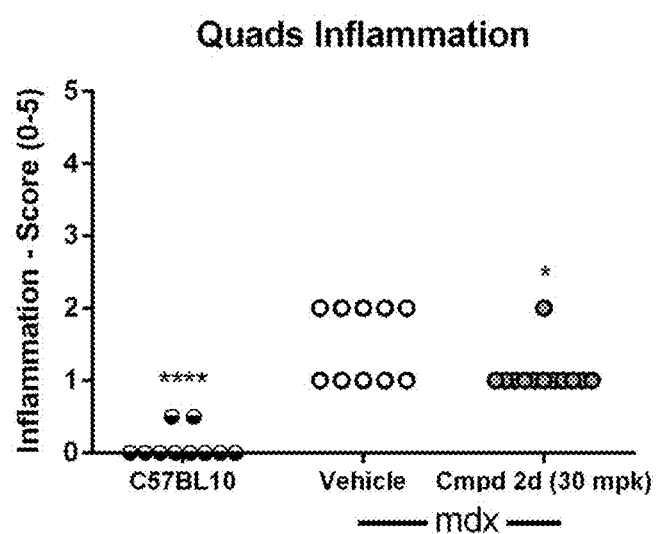
FIG. 6 is a plot showing inflammation is reduced in mdx quadriceps muscle with Compound 2d administration.

Decreased inflammation was also observed, an indication of reduced muscle damage, in Compound 2d treated mdx muscle (FIG. 6).

Figure 7:
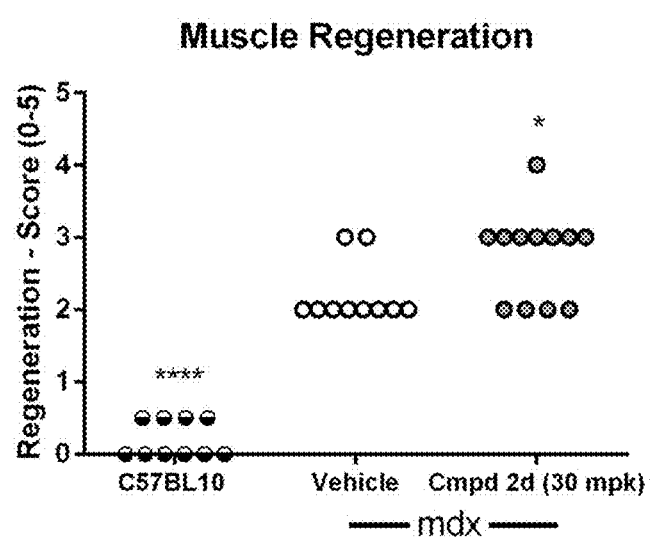
FIG. 7 is a plot showing quadriceps muscle regeneration is increased with Compound 2d administration in mdx mice.

While the amount of muscle damage is decreased in Compound 2d treated mdx mice, beneficial muscle regeneration increases with Compound 2d (FIG. 7).

Figure 8:
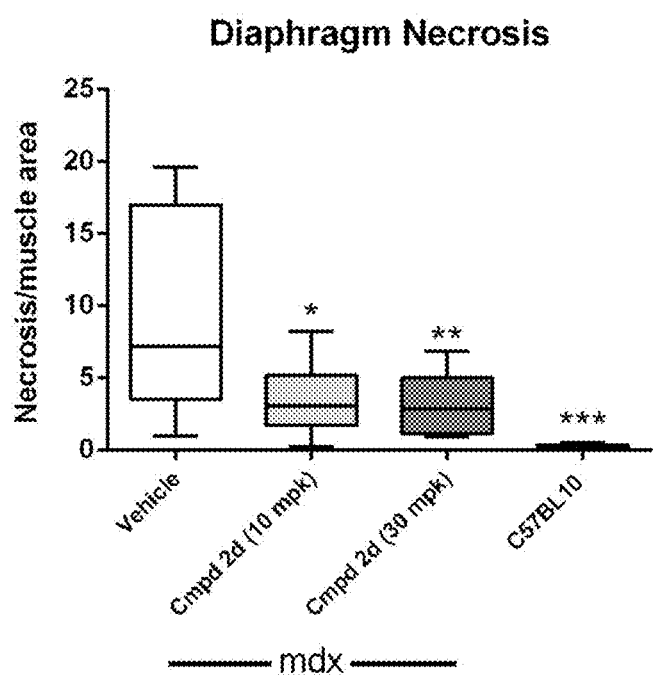
FIG. 8 is a graph showing diaphragm muscle necrosis is reduced with Compound 2d administration in mdx mice.

DMD patients and the mdx model of DMD have impaired respiratory function due, in part, to fibrosis of the diaphragm. See Huang, P., et al., *Impaired respiratory function in mdx and mdx/utrn(+/−) mice*. Muscle Nerve, 2011. 43(2): p. 263-7. Fibrosis, replacement of muscle with fibrotic extracellular matrix, is a component of muscular dystrophy that contributes to overall muscle weakness and poor muscle regeneration. Repeated cycles of muscle degeneration and regeneration can contribute to the development of fibrosis. Compound 2d treatment reduced diaphragm necrosis (FIG. 8), suggesting that fibrosis would also be reduced.

Figure 9:
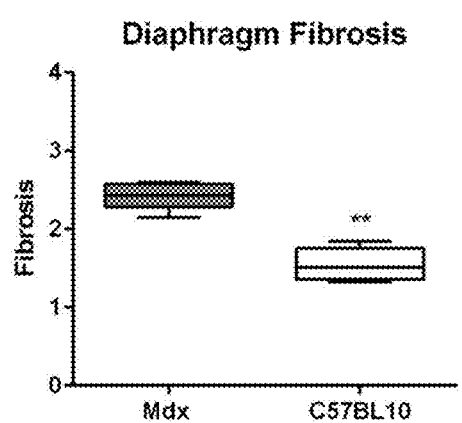
FIG. 9 is a graph showing mdx diaphragm muscles are more fibrotic than healthy, non-dystropic control mouse diaphragms.

Diaphragms were evaluated for fibrosis by measuring hydroxyproline, an amino acid unique to collagen, in digested muscle. Mdx mice were confirmed to have increased fibrosis versus non-dystrophic control mice (FIG. 9).

Figure 10:
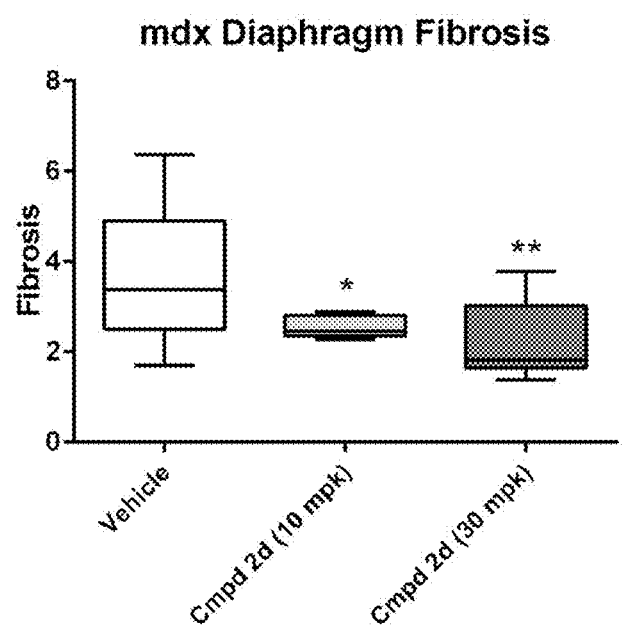
FIG. 10 is a graph showing Compound 2d administration reduces mdx mouse diaphragm fibrosis.

Compound 2d administration reduced fibrosis in mdx diaphragms (FIG. 10).

Example 6

PPARδ Modulation after Ischemia Reperfusion Reduces Kidney Injury

Animals, surgery and dosing: Sprague-Dawley male rats approximately 280-300 g, with ad libitum access to standard feed and water were used in these experiments. Rats were anesthetized with isoflurane and placed ventrally on a temperature controlled heated surgical platform. A skin incision was made on the dorsal surface, exposing both kidneys through flank incisions. Vascular clips were applied to both renal pedicles and occlusion lasted 45 minutes. After 45 min, the clips were removed, kidneys were monitored for successful reperfusion, and surgical sites were sutured. The sham group was subjected to similar surgical procedures, except that the occluding clamps were not applied. Four independent studies, testing each compound were performed. Compounds were formulated as a fresh daily suspension in 0.25% sodium carboxymethyl-cellulose, 0.25% Tween-80 in purified water. Compounds were dosed orally at 30 mg/kg 4 hours after animals awoke from surgery and sham surgery and IRI control animals were similarly dosed with vehicle.

Blood collection and plasma creatinine measurement: Twenty-four (24) hours after reperfusion, blood was collected in K2 EDTA tubes by retro-orbital bleeding from all groups under mild isoflurane anesthesia. Plasma was separated by centrifugation at 3000 rpm for 10 minutes at 4° C. Plasma creatinine was analyzed using a fully automated clinical biochemistry analyzer (Siemens Dimension® Xpand® Plus Integrated Chemistry System)

Data Analysis and Statistical Analysis:

GraphPad Prism software, Version 6.05 was used for graphing and statistical testing. Creatinine was tested for normal distribution in all groups via a D'Agostino-Pearson omnibus normality test and a Shapiro-Wilk normality test. Normally distributed data was subjected to an unpaired, two-tailed t test. Non-normally distributed data was subjected to a Mann-Whitney test (non-parametric). Statistical significance is determined by p<0.05 of IRI-vehicle compared to compound treated groups.

Figure 11A:
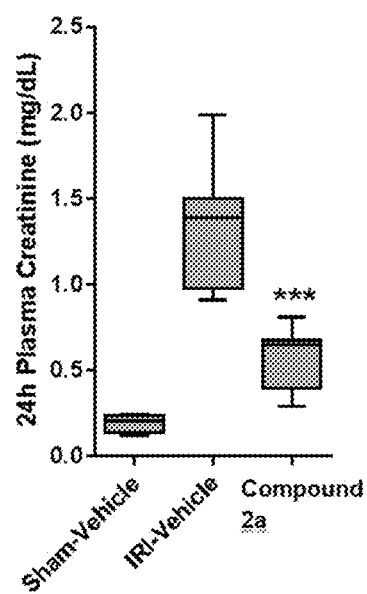
FIG. 11A is a graph showing the therapeutic effect of oral administration of Compound 2a in a rat model of acute kidney injury.
Figure 11B:
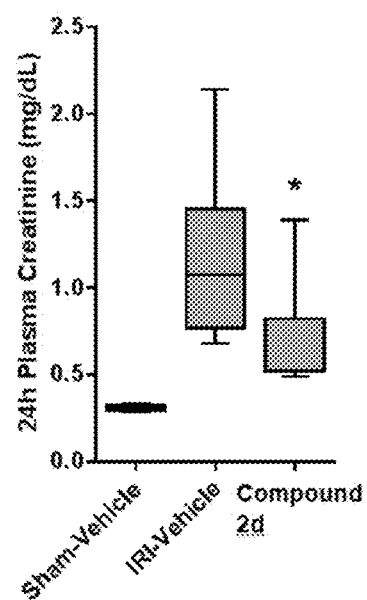
FIG. 11B is a graph showing the therapeutic effect of oral administration of Compound 2d in a rat model of acute kidney injury.
Figure 11C:
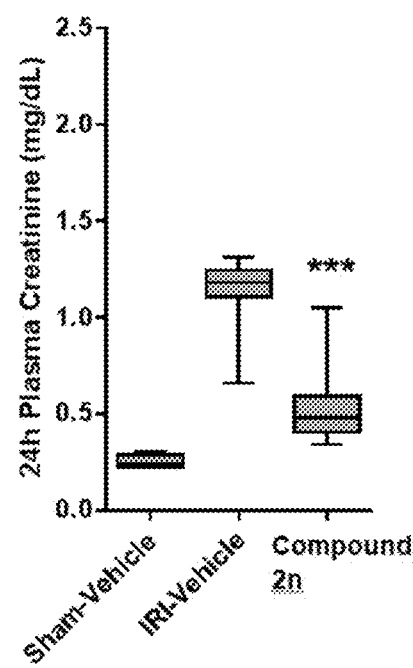
FIG. 11C is a graph showing the therapeutic effect of oral administration of Compound 2n in a rat model of acute kidney injury.

Results: PPARδ agonists, dosed 4 hours after ischemia, reduce kidney injury. Compound 2a (FIG. 11A), Compound 2d (FIG. 11B), and Compound 2n (FIG. 11C) reduce plasma creatinine when administered orally. The graph shows the plasma creatine levels in mg/dL in rats 24 hours after kidney injury reduce plasma creatinine when administered orally. The bars from left to right represent plasma creatine levels in rats with sham surgery dosed with 30 mpk vehicle; rats with acute kidney injury dosed with 30 mpk vehicle; and rats with acute kidney injury dosed with 30 mpk of Compound 2a (FIG. 11A), Compound 2d (FIG. 11B), and Compound 2n (FIG. 11C).

We claim:

1. A compound of Formula (I):

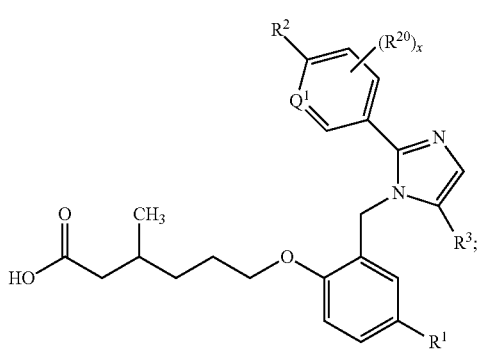

(I)

or a pharmaceutically acceptable salt thereof,
wherein:
$R^1$ is hydrogen, halogen, —$C_1$-$C_4$-alkyl, —$C_1$-$C_4$-haloalkyl, —CN, —$C_1$-$C_4$-alkoxy, —$C_1$-$C_4$-haloalkoxy, or —$C_3$-$C_6$-cycloalkyl;
$Q^1$ is CH;
$R^2$ is hydrogen, halogen, —CN, —$C_1$-$C_4$-alkyl, —$C_3$-$C_6$-cycloalkyl, —$C_1$-$C_4$-alkoxy, —S($C_1$-$C_4$-alkyl), —$SO_2$($C_1$-$C_4$-alkyl), 5- or 6-membered heterocycle, aryl, 5-membered heteroaryl, —≡—$R^{2A}$, —O($CH_2$)$_m$$R^{2B}$, —NH($C_1$-$C_4$-alkyl), —N($C_1$-$C_4$-alkyl)$_2$, or —C(O)($C_1$-$C_4$-alkyl), wherein aryl and heteroaryl are optionally substituted with halogen, —OH, —CN, $C_1$-$C_4$-alkyl, formyl, acetyl, acetoxy, or carboxy, and wherein m is an integer having value of 1, 2, or 3;
x is an integer having a value of 1 or 2;
$R^{2A}$ is —$C_1$-$C_4$-alkyl, —$C_1$-$C_4$-haloalkyl, or —$C_3$-$C_6$-cycloalkyl;
$R^{2B}$ is —$C_1$-$C_4$-alkyl or —$C_3$-$C_6$-cycloalkyl;
each $R^{20}$ is independently hydrogen, halogen, —$C_1$-$C_4$-alkyl, —CN, or —$C_1$-$C_4$-alkoxy; and
$R^3$ is —$CH_3$ or –$CD_3$.

2. The compound of claim 1, having the structure of Formula (Ia):

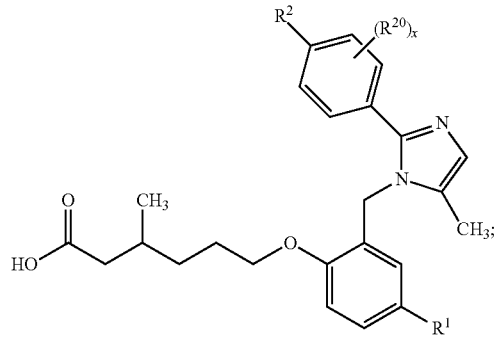

(Ia)

or a pharmaceutically acceptable salt thereof.

3. The compound of claim 2, wherein $R^2$ is halogen, —$C_1$-$C_4$-alkyl, —S($C_1$-$C_4$-alkyl), or furanyl, wherein the furanyl can be optionally substituted with —$C_1$-$C_4$-alkyl, or a pharmaceutically acceptable salt thereof.

4. The compound of claim 2, wherein $R^2$ is halogen, —$CH_3$, —$SCH_3$, or furanyl, wherein the furanyl can be optionally substituted with $CH_3$, or a pharmaceutically acceptable salt thereof.

5. The compound of claim 4, wherein $R^1$ is hydrogen or halogen, or a pharmaceutically acceptable salt thereof.

6. The compound of claim 5, wherein each $R^{20}$ is independently hydrogen or halogen, or a pharmaceutically acceptable salt thereof.

7. The compound of claim 6, wherein $R^2$ is chloro, unsubstituted furanyl, —$CH_3$, or —$SCH_3$, or a pharmaceutically acceptable salt thereof.

8. The compound of claim 6, wherein $R^1$ is hydrogen or fluoro, or a pharmaceutically acceptable salt thereof.

9. The compound of claim 8, wherein $R^{20}$ is hydrogen or fluoro, or a pharmaceutically acceptable salt thereof.

10. A pharmaceutical composition comprising a pharmaceutically acceptable carrier or excipient and the compound of claim 1, or a pharmaceutically acceptable salt thereof.

11. A method of treating a PPARδ related disease or condition in a subject, comprising administering to the subject in need thereof a therapeutically effective amount of one or more compounds of claim 1, or a pharmaceutically acceptable salt thereof.

12. The method of claim 11, wherein the PPARδ related disease is a muscle structure disorder, a neuronal activation disorder, a muscle fatigue disorder, a muscle mass disorder, a mitochondrial disease, a beta oxidation disease, a metabolic disease, a cancer, a vascular disease, an ocular vascular disease, a muscular eye disease, or a renal disease.

13. The method of claim 12, wherein:
the muscle structure disorder is selected from Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, or stress urinary incontinence; the neuronal activation disorder is selected from amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, or toxic myoneural disorder;

the muscle fatigue disorder is selected from chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, or thyrotoxic myopathy; the muscle mass disorder is cachexia, cartilage degeneration, cerebral palsy, compartment syndrome, critical illness myopathy, inclusion body myositis, muscular atrophy (disuse), sarcopenia, steroid myopathy, or systemic lupus erythematosus;

the mitochondrial disease is selected from Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, or Pearson Syndrome;

the beta oxidation disease is selected from systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency or riboflavin-responsive disorders of β-oxidation (RR-MADD);

the metabolic disease is selected from hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, Non-alcoholic fatty liver disease (NAFLD), Nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, or pancreatitis;

the cancer is a cancer of the colon, large intestine, skin, breast, prostate, ovary, or lung;

the vascular disease is selected from peripheral vascular insufficiency, peripheral vascular disease, intermittent claudication, peripheral vascular disease (PVD), peripheral artery disease (PAD), peripheral artery occlusive disease (PAOD), or peripheral obliterative arteriopathy;

the ocular vascular disease is selected from age-related macular degeneration (AMD), stargardt disease, hypertensive retinopathy, diabetic retinopathy, retinopathy, macular degeneration, retinal haemorrhage, or glaucoma;

the muscular eye disease is selected from strabismus, progressive external ophthalmoplegia, esotropia, exotropia, a disorder of refraction and accommodation, hypermetropia, myopia, astigmatism, anisometropia, presbyopia, a disorders of accommodation, or internal ophthalmoplegia; and the renal disease is selected from glomerulonephritis, glomerulosclerosis, nephrotic syndrome, hypertensive nephrosclerosis, acute nephritis, recurrent hematuria, persistent hematuria, chronic nephritis, rapidly progressive nephritis, acute renal failure, chronic renal failure, diabetic nephropathy, or Bartter's syndrome.

14. A method of treating a disease or condition in a subject, comprising administering to the subject in need thereof a therapeutically effective amount of a compound of claim 1, or a pharmaceutically acceptable salt thereof, wherein the disease or condition is Alpers Disease, chronic progressive external ophthalmoplegia (CPEO), Kearns-Sayre Syndrome (KSS), Leber Hereditary Optic Neuropathy (LHON), MELAS-mitochondrial myopathy, encephalomyopathy, lactic acidosis, and stroke-like episodes, myoclonic epilepsy with ragged-red fiber disease (MERRF), neurogenic muscle weakness-ataxia-retinitis pigmentosa (NARP), or Pearson Syndrome.

15. A method of treating Duchenne Muscular Dystrophy in a subject, comprising administering to the subject in need thereof a therapeutically effective amount of a compound of claim 1, or a pharmaceutically acceptable salt thereof.

16. A method of treating chronic fatigue syndrome in a subject, comprising administering to the subject in need thereof a therapeutically effective amount of one or more compounds of claim 1, or a pharmaceutically acceptable salt thereof.

* * * * *